(12) United States Patent
Wu et al.

(10) Patent No.: US 10,718,031 B1
(45) Date of Patent: Jul. 21, 2020

(54) METHOD AND SYSTEM FOR MATCHING ENTITIES IN AN AUCTION

(71) Applicants: Wai Wu, Massapequa, NY (US); Steven M. Hoffberg, West Harrison, NY (US)

(72) Inventors: Wai Wu, Massapequa, NY (US); Steven M. Hoffberg, West Harrison, NY (US)

(\*) Notice: Subject to any disclaimer, the term of this patent is extended or adjusted under 35 U.S.C. 154(b) by 0 days.

(21) Appl. No.: 16/356,852

(22) Filed: Mar. 18, 2019

Related U.S. Application Data

(63) Continuation of application No. 15/836,729, filed on Dec. 8, 2017.

(51) Int. Cl.
*H04M 3/00* (2006.01)
*H04M 5/00* (2006.01)
(Continued)

(52) U.S. Cl.
CPC ........ *C12Q 1/6886* (2013.01); *C07K 16/2878* (2013.01); *G01N 33/57484* (2013.01);
(Continued)

(58) Field of Classification Search
CPC .. G10L 15/00; G06Q 10/06; G06Q 10/06316; G06Q 30/016; H04L 51/02; H04L 51/046; H04L 51/24; H04M 3/323; H04M 3/36; H04M 3/4217; H04M 3/4285; H04M 3/42195; H04M 3/493; H04M 3/4931; H04M 3/4933; H04M 3/4935; H04M 3/4936; H04M 3/4938; H04M 3/42221; H04M 3/51; H04M 3/5158; H04M 3/5166; H04M 3/5175; H04M 3/5183; H04M 3/5191; H04M 3/523; H04M 3/5231; H04M 3/5232; H04M 3/5233; H04M 3/5235; H04M 3/5237; H04M 3/5238; H04M 3/54; H04M 2203/40; H04M 2203/401; H04M 2203/2011; H04M 2203/2061; H04M 2242/00; H04M 2242/08; H04M 2242/12
USPC ............ 379/210.01, 265.01, 265.02, 265.03, 379/265.04, 265.05, 265.06, 265.07, 379/265.08, 265.09, 265.1, 265.11, 379/265.12, 265.13, 265.14, 266.01, 379/266.02, 266.03, 266.04, 266.05,
(Continued)

(56) References Cited

U.S. PATENT DOCUMENTS 4,048,452 A 9/1977 Oehring et al.
4,286,118 A 8/1981 Mehaffey et al.
(Continued)

*Primary Examiner* — Khai N. Nguyen
(74) *Attorney, Agent, or Firm* — Hoffberg & Associates; Steven M. Hoffberg

(57) ABSTRACT

A method for matching a first entity with at least one second entity selected from a plurality of second entities, comprising defining a plurality of multivalued scalar data representing inferential targeting parameters for the first entity and a plurality of multivalued scalar data of each of the plurality of second entities, representing respective characteristic parameters for each respective second entity; and performing an automated optimization with respect to an economic surplus of a respective match of the first entity with the at least one of the plurality of second entities, and an opportunity cost of the unavailability of the at least one of the plurality of second entities for matching with an alternate first entity.

20 Claims, 7 Drawing Sheets

(51) Int. Cl.
*C12Q 1/6886* (2018.01)
*C07K 16/28* (2006.01)
*G01N 33/574* (2006.01)
*H04M 3/51* (2006.01)
*H04M 3/523* (2006.01)

(52) U.S. Cl.
CPC ........... *H04M 3/51* (2013.01); *C07K 2317/24* (2013.01); *C07K 2317/75* (2013.01); *C12Q 2600/106* (2013.01); *C12Q 2600/158* (2013.01); *G01N 2800/52* (2013.01); *H04M 3/5238* (2013.01); *H04M 2203/402* (2013.01)

(58) Field of Classification Search
USPC ............ 379/266.06, 266.07, 266.08, 266.09, 379/266.1
See application file for complete search history.

(56) References Cited

U.S. PATENT DOCUMENTS

| | | | |
|---|---|---|---|
| 4,677,663 A | 6/1987 | Szlam | |
| 4,737,983 A | 4/1988 | Frauenthal et al. | |
| 4,757,529 A | 7/1988 | Glapa et al. | |
| 4,768,221 A | 8/1988 | Green et al. | |
| 4,797,911 A | 1/1989 | Szlam et al. | |
| 4,807,279 A | 2/1989 | McClure et al. | |
| 4,852,149 A | 7/1989 | Zwick et al. | |
| 4,866,754 A | 9/1989 | Hashimoto | |
| 4,878,243 A | 10/1989 | Hashimoto | |
| 4,893,301 A | 1/1990 | Andrews et al. | |
| 4,894,857 A | 1/1990 | Szlam et al. | |
| 4,924,501 A | 5/1990 | Cheeseman et al. | |
| 4,930,150 A | 5/1990 | Katz | |
| 4,933,964 A | 6/1990 | Girgis | |
| 4,935,956 A | 6/1990 | Hellwarth et al. | |
| 4,941,168 A | 7/1990 | Kelly, Jr. | |
| 4,953,204 A | 8/1990 | Cuschleg, Jr. et al. | |
| 4,958,371 A | 9/1990 | Damoci et al. | |
| 4,975,841 A | 12/1990 | Kehnemuyi et al. | |
| 4,977,595 A | 12/1990 | Ohta et al. | |
| 4,979,171 A | 12/1990 | Ashley | |
| 4,987,587 A | 1/1991 | Jolissaint | |
| 4,998,272 A | 3/1991 | Hawkins, Jr. et al. | |
| 5,006,983 A * | 4/1991 | Wayne | G06Q 10/06 705/7.13 |
| 5,007,000 A | 4/1991 | Baldi | |
| 5,007,078 A | 4/1991 | Masson et al. | |
| 5,014,298 A | 5/1991 | Katz | |
| 5,016,270 A | 5/1991 | Katz | |
| 5,020,095 A | 5/1991 | Morganstein et al. | |
| 5,020,097 A | 5/1991 | Tanaka et al. | |
| 5,036,535 A | 7/1991 | Gechter et al. | |
| 5,040,208 A | 8/1991 | Jolissaint | |
| 5,048,075 A | 9/1991 | Katz | |
| 5,063,522 A | 11/1991 | Winters | |
| 5,070,525 A | 12/1991 | Szlam et al. | |
| 5,070,526 A | 12/1991 | Richmond et al. | |
| 5,073,890 A | 12/1991 | Danielsen | |
| 5,073,929 A | 12/1991 | Katz | |
| 5,077,789 A | 12/1991 | Clark, Jr. et al. | |
| 5,081,711 A | 1/1992 | Rickman, Jr. | |
| 5,097,528 A | 3/1992 | Gursahaney et al. | |
| 5,103,449 A | 4/1992 | Jolissaint | |
| 5,121,422 A | 6/1992 | Kudo | |
| 5,128,984 A | 7/1992 | Katz | |
| 5,161,181 A | 11/1992 | Zwick | |
| 5,163,083 A | 11/1992 | Dowden et al. | |
| 5,163,087 A | 11/1992 | Kaplan | |
| 5,164,981 A | 11/1992 | Mitchell et al. | |
| 5,166,974 A | 11/1992 | Morganstein et al. | |
| 5,168,517 A | 12/1992 | Waldman | |
| 5,185,786 A | 2/1993 | Zwick | |
| 5,193,110 A | 3/1993 | Jones et al. | |
| 5,206,903 A | 4/1993 | Kohler et al. | |
| 5,214,688 A | 5/1993 | Szlam et al. | |
| 5,218,635 A | 6/1993 | Bonvallet et al. | |
| 5,224,153 A | 6/1993 | Katz | |
| 5,224,162 A | 6/1993 | Okamoto et al. | |
| 5,237,159 A | 8/1993 | Stephens et al. | |
| 5,239,574 A | 8/1993 | Brandman et al. | |
| 5,247,569 A * | 9/1993 | Cave | H04M 3/36 379/112.01 |
| 5,251,252 A | 10/1993 | Katz | |
| 5,253,289 A | 10/1993 | Tanaka | |
| 5,255,349 A | 10/1993 | Thakoor et al. | |
| 5,274,700 A * | 12/1993 | Gechter | H04M 3/5125 379/211.01 |
| 5,276,732 A | 1/1994 | Stent et al. | |
| 5,278,898 A | 1/1994 | Cambray et al. | |
| 5,283,818 A | 2/1994 | Klausner et al. | |
| 5,289,530 A | 2/1994 | Reese | |
| 5,291,550 A | 3/1994 | Levy et al. | |
| 5,297,146 A | 3/1994 | Ogawa | |
| 5,297,195 A | 3/1994 | Thorne et al. | |
| 5,309,504 A | 5/1994 | Morganstein | |
| 5,309,505 A | 5/1994 | Szlam et al. | |
| 5,309,513 A | 5/1994 | Rose | |
| 5,311,574 A | 5/1994 | Livanos | |
| 5,311,577 A | 5/1994 | Madrid et al. | |
| 5,313,516 A | 5/1994 | Afshar et al. | |
| 5,319,703 A | 6/1994 | Drory | |
| 5,321,745 A | 6/1994 | Drory et al. | |
| 5,325,292 A | 6/1994 | Crockett | |
| 5,327,490 A * | 7/1994 | Cave | H04M 3/36 379/265.08 |
| 5,329,579 A | 7/1994 | Brunson | |
| 5,333,190 A | 7/1994 | Eyster | |
| 5,341,412 A | 8/1994 | Ramot et al. | |
| 5,341,414 A | 8/1994 | Popke | |
| 5,351,285 A | 9/1994 | Katz | |
| 5,359,645 A | 10/1994 | Katz | |
| 5,365,575 A | 11/1994 | Katz | |
| 5,369,695 A | 11/1994 | Chakravarti et al. | |
| 5,381,470 A | 1/1995 | Cambray et al. | |
| 5,390,236 A | 2/1995 | Klausner et al. | |
| 5,392,353 A | 2/1995 | Morales | |
| 5,400,393 A | 3/1995 | Knuth et al. | |
| 5,402,474 A | 3/1995 | Miller et al. | |
| 5,420,852 A | 5/1995 | Anderson et al. | |
| 5,420,919 A | 5/1995 | Arnaud et al. | |
| 5,425,093 A | 6/1995 | Trefzger | |
| 5,430,792 A | 7/1995 | Jesurum et al. | |
| 5,432,835 A | 7/1995 | Hashimoto | |
| 5,434,906 A | 7/1995 | Robinson et al. | |
| 5,436,967 A | 7/1995 | Hanson | |
| 5,442,693 A | 8/1995 | Hays et al. | |
| 5,448,624 A | 9/1995 | Hardy et al. | |
| 5,448,631 A | 9/1995 | Cain | |
| 5,459,781 A | 10/1995 | Kaplan et al. | |
| 5,465,286 A | 11/1995 | Clare et al. | |
| 5,467,391 A | 11/1995 | Donaghue, Jr. et al. | |
| 5,479,487 A | 12/1995 | Hammond | |
| 5,479,501 A | 12/1995 | Lai | |
| 5,481,596 A | 1/1996 | Comerford | |
| 5,485,506 A | 1/1996 | Recht et al. | |
| 5,493,690 A | 2/1996 | Shimazaki | |
| 5,495,523 A | 2/1996 | Stent et al. | |
| 5,495,528 A | 2/1996 | Dunn et al. | |
| 5,502,762 A | 3/1996 | Andrew et al. | |
| 5,506,898 A | 4/1996 | Costantini et al. | |
| 5,511,112 A | 4/1996 | Szlam | |
| 5,511,117 A | 4/1996 | Zazzera | |
| 5,511,121 A | 4/1996 | Yacobi | |
| 5,515,421 A | 5/1996 | Sikand et al. | |
| 5,517,566 A | 5/1996 | Smith et al. | |
| 5,519,773 A | 5/1996 | Dumas et al. | |
| 5,524,140 A | 6/1996 | Klausner et al. | |
| 5,524,147 A | 6/1996 | Bean | |
| 5,526,417 A | 6/1996 | Dezonno | |
| 5,528,666 A | 6/1996 | Weigand et al. | |
| 5,530,931 A | 6/1996 | Cook-Hellberg et al. | |
| 5,533,103 A | 7/1996 | Peavey et al. | |
| 5,533,107 A | 7/1996 | Irwin et al. | |

(56) References Cited

U.S. PATENT DOCUMENTS

| | | |
|---|---|---|
| 5,533,109 A | 7/1996 | Baker |
| 5,535,257 A | 7/1996 | Goldberg et al. |
| 5,537,470 A | 7/1996 | Lee |
| 5,544,220 A | 8/1996 | Trefzger |
| 5,544,232 A | 8/1996 | Baker et al. |
| 5,546,452 A | 8/1996 | Andrews et al. |
| 5,546,456 A | 8/1996 | Vilsoet et al. |
| 5,555,290 A | 9/1996 | McLeod et al. |
| 5,555,295 A | 9/1996 | Bhusri |
| 5,557,668 A | 9/1996 | Brady |
| 5,559,867 A | 9/1996 | Langsenkamp et al. |
| 5,559,878 A | 9/1996 | Keys et al. |
| 5,560,011 A | 9/1996 | Uyama |
| 5,561,711 A | 10/1996 | Muller |
| 5,568,540 A | 10/1996 | Greco et al. |
| 5,570,419 A | 10/1996 | Cave et al. |
| 5,572,576 A | 11/1996 | Klausner et al. |
| 5,572,586 A | 11/1996 | Ouchi |
| 5,574,782 A * | 11/1996 | Baird .................. H04M 3/523 379/221.09 |
| 5,574,784 A | 11/1996 | LaPadula et al. |
| 5,577,112 A | 11/1996 | Cambray et al. |
| 5,579,377 A | 11/1996 | Rogers |
| 5,579,383 A | 11/1996 | Bales et al. |
| 5,581,602 A | 12/1996 | Szlam et al. |
| 5,581,604 A | 12/1996 | Robinson et al. |
| 5,581,607 A | 12/1996 | Richardson, Jr. et al. |
| 5,586,179 A | 12/1996 | Stent et al. |
| 5,588,049 A | 12/1996 | Detering et al. |
| 5,590,171 A | 12/1996 | Howe et al. |
| 5,590,188 A | 12/1996 | Crockett |
| 5,592,543 A | 1/1997 | Smith et al. |
| 5,594,790 A | 1/1997 | Curreri et al. |
| 5,594,791 A | 1/1997 | Szlam et al. |
| 5,600,710 A | 2/1997 | Weisser, Jr. et al. |
| 5,610,774 A | 3/1997 | Hayashi et al. |
| 5,610,978 A | 3/1997 | Purits |
| 5,619,557 A | 4/1997 | Van Berkum |
| 5,621,201 A | 4/1997 | Langhans et al. |
| 5,623,547 A | 4/1997 | Jones et al. |
| 5,625,676 A | 4/1997 | Greco et al. |
| 5,625,682 A | 4/1997 | Gray et al. |
| 5,633,917 A | 5/1997 | Rogers |
| 5,633,922 A | 5/1997 | August et al. |
| 5,633,924 A | 5/1997 | Kaish et al. |
| 5,636,267 A | 6/1997 | Utsumi et al. |
| 5,636,268 A | 6/1997 | Dijkstra et al. |
| 5,638,436 A | 6/1997 | Hamilton et al. |
| 5,646,986 A | 7/1997 | Sahni et al. |
| 5,646,988 A | 7/1997 | Hikawa |
| 5,652,788 A | 7/1997 | Hara |
| 5,655,013 A | 8/1997 | Gainsboro |
| 5,655,014 A | 8/1997 | Walsh et al. |
| 5,657,074 A | 8/1997 | Ishibe et al. |
| 5,661,283 A | 8/1997 | Gallacher et al. |
| 5,666,416 A | 9/1997 | Micali |
| 5,666,523 A | 9/1997 | DSouza |
| 5,675,637 A | 10/1997 | Szlam et al. |
| 5,677,955 A | 10/1997 | Doggett et al. |
| 5,679,940 A | 10/1997 | Templeton et al. |
| 5,684,863 A | 11/1997 | Katz |
| 5,687,225 A | 11/1997 | Jorgensen |
| 5,692,033 A | 11/1997 | Farris |
| 5,692,034 A | 11/1997 | Richardson, Jr. et al. |
| 5,696,809 A | 12/1997 | Voit |
| 5,696,818 A | 12/1997 | Doremus et al. |
| 5,696,908 A | 12/1997 | Muehlberger et al. |
| 5,699,418 A | 12/1997 | Jones |
| 5,701,295 A | 12/1997 | Bales et al. |
| 5,703,935 A | 12/1997 | Raissyan et al. |
| 5,715,307 A | 2/1998 | Zazzera |
| 5,717,741 A | 2/1998 | Yue et al. |
| 5,717,757 A | 2/1998 | Micali |
| RE35,758 E | 3/1998 | Winter et al. |
| 5,724,418 A | 3/1998 | Brady |
| 5,727,154 A | 3/1998 | Fry et al. |
| 5,729,600 A | 3/1998 | Blaha et al. |
| 5,740,233 A | 4/1998 | Cave et al. |
| 5,740,240 A | 4/1998 | Jolissaint |
| 5,742,675 A | 4/1998 | Kilander et al. |
| 5,748,711 A | 5/1998 | Scherer |
| 5,754,939 A | 5/1998 | Herz et al. |
| 5,761,285 A | 6/1998 | Stent |
| 5,768,355 A | 6/1998 | Salibrici et al. |
| 5,768,360 A | 6/1998 | Reynolds et al. |
| 5,768,385 A | 6/1998 | Simon |
| 5,774,357 A | 6/1998 | Hoffberg et al. |
| 5,774,537 A | 6/1998 | Kim |
| 5,787,156 A | 7/1998 | Katz |
| 5,787,159 A | 7/1998 | Hamilton et al. |
| 5,790,935 A | 8/1998 | Payton |
| 5,793,846 A | 8/1998 | Katz |
| 5,793,868 A | 8/1998 | Micali |
| 5,796,791 A | 8/1998 | Polcyn |
| 5,796,816 A | 8/1998 | Utsumi |
| 5,799,077 A | 8/1998 | Yoshii |
| 5,799,087 A | 8/1998 | Rosen |
| 5,802,502 A | 9/1998 | Gell et al. |
| 5,806,071 A | 9/1998 | Balderrama et al. |
| 5,812,642 A | 9/1998 | Leroy |
| 5,812,668 A | 9/1998 | Weber |
| 5,815,551 A | 9/1998 | Katz |
| 5,815,554 A | 9/1998 | Burgess et al. |
| 5,815,566 A | 9/1998 | Ramot et al. |
| 5,815,657 A | 9/1998 | Williams et al. |
| 5,822,400 A | 10/1998 | Smith |
| 5,822,401 A | 10/1998 | Cave et al. |
| 5,822,410 A | 10/1998 | McCausland et al. |
| 5,825,869 A | 10/1998 | Brooks et al. |
| 5,828,731 A | 10/1998 | Szlam et al. |
| 5,828,734 A | 10/1998 | Katz |
| 5,828,840 A | 10/1998 | Cowan et al. |
| 5,832,089 A | 11/1998 | Kravitz et al. |
| 5,835,572 A | 11/1998 | Richardson, Jr. et al. |
| 5,835,896 A | 11/1998 | Fisher et al. |
| 5,838,772 A | 11/1998 | Wilson et al. |
| 5,838,779 A | 11/1998 | Fuller et al. |
| 5,839,119 A | 11/1998 | Krsul et al. |
| 5,841,852 A | 11/1998 | He |
| 5,848,143 A | 12/1998 | Andrews et al. |
| 5,850,428 A | 12/1998 | Day |
| 5,850,446 A | 12/1998 | Berger et al. |
| 5,854,832 A | 12/1998 | Dezonno |
| 5,857,013 A | 1/1999 | Yue et al. |
| 5,857,023 A | 1/1999 | Demers et al. |
| 5,867,386 A | 2/1999 | Hoffberg et al. |
| 5,867,559 A | 2/1999 | Jorgensen et al. |
| 5,867,564 A | 2/1999 | Bhusri |
| 5,867,572 A | 2/1999 | MacDonald et al. |
| 5,867,799 A | 2/1999 | Lang et al. |
| 5,870,464 A | 2/1999 | Brewster et al. |
| 5,872,833 A | 2/1999 | Scherer |
| 5,873,071 A | 2/1999 | Ferstenberg et al. |
| 5,875,108 A | 2/1999 | Hoffberg et al. |
| 5,878,126 A | 3/1999 | Velamuri et al. |
| 5,878,130 A | 3/1999 | Andrews et al. |
| 5,884,277 A | 3/1999 | Khosla |
| 5,889,862 A | 3/1999 | Ohta et al. |
| 5,889,863 A | 3/1999 | Weber |
| 5,890,138 A | 3/1999 | Godin et al. |
| 5,893,902 A | 4/1999 | Transue et al. |
| 5,894,505 A | 4/1999 | Koyama |
| 5,896,446 A | 4/1999 | Sagady et al. |
| 5,898,154 A | 4/1999 | Rosen |
| 5,898,759 A | 4/1999 | Huang |
| 5,898,762 A | 4/1999 | Katz |
| 5,901,209 A | 5/1999 | Tannenbaum et al. |
| 5,901,214 A | 5/1999 | Shaffer et al. |
| 5,901,229 A | 5/1999 | Fujisaki et al. |
| 5,901,246 A | 5/1999 | Hoffberg et al. |
| 5,903,454 A | 5/1999 | Hoffberg et al. |
| 5,903,641 A * | 5/1999 | Tonisson .......... H04M 3/5233 379/265.12 |
| 5,903,651 A | 5/1999 | Kocher |

(56) References Cited

U.S. PATENT DOCUMENTS

| | | |
|---|---|---|
| 5,903,880 A | 5/1999 | Biffar |
| 5,905,792 A | 5/1999 | Miloslavsky |
| 5,905,975 A | 5/1999 | Ausubel |
| 5,905,979 A | 5/1999 | Barrows |
| 5,907,601 A | 5/1999 | David et al. |
| 5,907,608 A | 5/1999 | Shaffer et al. |
| 5,910,982 A | 6/1999 | Shaffer et al. |
| 5,912,947 A | 6/1999 | Langsenkamp et al. |
| 5,913,195 A | 6/1999 | Weeren et al. |
| 5,914,951 A | 6/1999 | Bentley et al. |
| 5,915,011 A | 6/1999 | Miloslavsky |
| 5,915,093 A | 6/1999 | Berlin et al. |
| 5,917,893 A | 6/1999 | Katz |
| 5,917,903 A | 6/1999 | Jolissaint |
| 5,918,213 A | 6/1999 | Bernard et al. |
| 5,920,477 A | 7/1999 | Hoffberg et al. |
| 5,920,629 A | 7/1999 | Rosen |
| 5,923,745 A | 7/1999 | Hurd |
| 5,923,746 A | 7/1999 | Baker et al. |
| 5,924,016 A | 7/1999 | Fuller et al. |
| 5,926,528 A | 7/1999 | David |
| 5,926,539 A | 7/1999 | Shtivelman |
| 5,926,548 A | 7/1999 | Okamoto |
| 5,930,339 A | 7/1999 | Nepustil |
| 5,930,777 A | 7/1999 | Barber |
| 5,933,480 A | 8/1999 | Felger |
| 5,933,492 A | 8/1999 | Turovski |
| 5,933,498 A | 8/1999 | Schneck et al. |
| 5,937,055 A | 8/1999 | Kaplan |
| 5,937,390 A | 8/1999 | Hyodo |
| 5,937,394 A | 8/1999 | Wong et al. |
| 5,940,493 A | 8/1999 | Desai et al. |
| 5,940,496 A | 8/1999 | Gisby et al. |
| 5,940,497 A | 8/1999 | Miloslavsky |
| 5,940,813 A | 8/1999 | Hutchings |
| 5,940,947 A | 8/1999 | Takeuchi et al. |
| 5,941,813 A | 8/1999 | Sievers et al. |
| 5,943,403 A | 8/1999 | Richardson, Jr. et al. |
| 5,943,424 A | 8/1999 | Berger et al. |
| 5,946,387 A | 8/1999 | Miloslavsky |
| 5,946,388 A | 8/1999 | Walker et al. |
| 5,946,394 A | 8/1999 | Gambuzza |
| 5,946,669 A | 8/1999 | Polk |
| 5,949,045 A | 9/1999 | Ezawa et al. |
| 5,949,852 A | 9/1999 | Duncan |
| 5,949,854 A | 9/1999 | Sato |
| 5,949,863 A | 9/1999 | Tansky |
| 5,952,638 A | 9/1999 | Demers et al. |
| 5,953,332 A | 9/1999 | Miloslavsky |
| 5,953,405 A | 9/1999 | Miloslavsky |
| 5,956,392 A | 9/1999 | Tanigawa et al. |
| 5,956,397 A | 9/1999 | Shaffer et al. |
| 5,960,073 A | 9/1999 | Kikinis et al. |
| 5,960,083 A | 9/1999 | Micali |
| 5,963,632 A | 10/1999 | Miloslavsky |
| 5,963,635 A | 10/1999 | Szlam et al. |
| 5,963,648 A | 10/1999 | Rosen |
| 5,963,924 A | 10/1999 | Williams et al. |
| 5,966,429 A | 10/1999 | Scherer |
| RE36,416 E | 11/1999 | Szlam et al. |
| RE37,001 E | 12/2000 | Morganstein et al. |
| 6,163,607 A * | 12/2000 | Bogart ............ H04M 3/5233 379/265.02 |
| 6,333,980 B1 * | 12/2001 | Hollatz ............ H04M 3/5233 379/265.12 |
| 6,389,400 B1 * | 5/2002 | Bushey ........ G06Q 10/063112 705/7.14 |
| 6,570,980 B1 * | 5/2003 | Baruch ............ H04M 3/523 379/265.12 |
| 6,639,982 B1 * | 10/2003 | Stuart ............ H04M 3/51 379/265.01 |
| 6,654,459 B1 * | 11/2003 | Bala ............ H04L 63/08 379/265.04 |
| 6,683,945 B1 * | 1/2004 | Enzmann ............ H04L 45/00 379/114.02 |
| 6,711,253 B1 * | 3/2004 | Prabhaker ............ H04M 3/36 379/265.01 |
| 6,804,345 B1 * | 10/2004 | Bala ............ H04M 3/382 379/265.04 |
| 6,842,515 B2 * | 1/2005 | Mengshoel ......... H04M 3/5237 379/265.02 |
| 6,868,525 B1 * | 3/2005 | Szabo ............ G06Q 30/02 715/738 |
| 6,978,252 B2 * | 12/2005 | Shuster ............ G06Q 20/10 705/21 |
| 7,023,979 B1 * | 4/2006 | Wu ............ H04M 3/5233 379/265.11 |
| 7,110,525 B1 * | 9/2006 | Heller ............ H04M 3/523 379/265.11 |
| 7,184,540 B2 * | 2/2007 | Dezonno ............ H04M 3/523 379/265.02 |
| 7,200,219 B1 * | 4/2007 | Edwards ............ H04M 3/5237 379/265.01 |
| 7,269,253 B1 * | 9/2007 | Wu ............ H04M 3/5233 379/265.11 |
| 7,372,952 B1 | 5/2008 | Wu et al. |
| 7,373,310 B1 | 5/2008 | Homsi |
| 7,415,432 B1 | 8/2008 | Gianakouros et al. |
| 7,424,617 B2 | 9/2008 | Boyd et al. |
| 7,451,005 B2 | 11/2008 | Hoffberg et al. |
| 7,472,080 B2 | 12/2008 | Goel |
| 7,475,054 B2 | 1/2009 | Hearing et al. |
| 7,590,589 B2 | 9/2009 | Hoffberg |
| 7,603,304 B2 | 10/2009 | Asthana et al. |
| 7,640,166 B2 | 12/2009 | Wiederin et al. |
| 7,644,144 B1 * | 1/2010 | Horvitz ............ G06Q 10/10 709/203 |
| 7,650,319 B2 | 1/2010 | Hoffberg et al. |
| 7,676,034 B1 * | 3/2010 | Wu ............ H04M 3/5233 379/265.01 |
| 7,716,532 B2 | 5/2010 | Horvitz |
| 7,773,749 B1 | 8/2010 | Durst et al. |
| 7,813,822 B1 | 10/2010 | Hoffberg |
| 7,817,796 B1 | 10/2010 | Clippinger et al. |
| 7,869,591 B1 | 1/2011 | Nagel et al. |
| 7,870,240 B1 | 1/2011 | Horvitz |
| 7,877,304 B1 | 1/2011 | Coulter |
| 7,894,595 B1 | 2/2011 | Wu et al. |
| 7,904,187 B2 | 3/2011 | Hoffberg et al. |
| 7,916,858 B1 | 3/2011 | Heller et al. |
| 7,945,464 B2 | 5/2011 | El Homsi |
| 7,949,121 B1 | 5/2011 | Flockhart et al. |
| 7,953,219 B2 * | 5/2011 | Freedman ............ G06Q 30/02 379/265.06 |
| 7,966,078 B2 | 6/2011 | Hoffberg et al. |
| 7,974,714 B2 | 7/2011 | Hoffberg |
| 7,987,003 B2 | 7/2011 | Hoffberg et al. |
| 8,015,073 B2 | 9/2011 | Ilechko et al. |
| 8,031,060 B2 | 10/2011 | Hoffberg et al. |
| 8,032,477 B1 | 10/2011 | Hoffberg et al. |
| 8,046,313 B2 | 10/2011 | Hoffberg et al. |
| 8,054,965 B1 | 11/2011 | Wu et al. |
| 8,073,731 B1 | 12/2011 | Rajasenan |
| 8,144,619 B2 | 3/2012 | Hoffberg |
| 8,165,916 B2 | 4/2012 | Hoffberg et al. |
| 8,233,918 B2 | 7/2012 | Roin et al. |
| 8,270,603 B1 | 9/2012 | Durst et al. |
| 8,300,798 B1 * | 10/2012 | Wu ............ H04M 3/5233 379/265.11 |
| 8,316,237 B1 | 11/2012 | Felsher et al. |
| 8,352,400 B2 | 1/2013 | Hoffberg et al. |
| 8,364,136 B2 | 1/2013 | Hoffberg et al. |
| 8,369,967 B2 | 2/2013 | Hoffberg et al. |
| 8,373,582 B2 | 2/2013 | Hoffberg |
| 8,402,490 B2 | 3/2013 | Hoffberg-Borghesani et al. |
| 8,411,842 B1 | 4/2013 | Wu et al. |
| 8,516,266 B2 | 8/2013 | Hoffberg et al. |
| 8,566,247 B1 | 10/2013 | Nagel et al. |
| 8,582,753 B1 | 11/2013 | Heller et al. |
| 8,583,263 B2 | 11/2013 | Hoffberg et al. |
| 8,600,830 B2 | 12/2013 | Hoffberg |

(56) References Cited

U.S. PATENT DOCUMENTS

| | | |
|---|---|---|
| 8,629,789 B2 | 1/2014 | Hoffberg |
| 8,682,726 B2 | 3/2014 | Hoffberg |
| 8,831,205 B1 | 9/2014 | Wu et al. |
| 8,874,477 B2 | 10/2014 | Hoffberg |
| 8,892,495 B2 | 11/2014 | Hoffberg et al. |
| 8,904,181 B1 | 12/2014 | Felsher et al. |
| 8,971,519 B1 | 3/2015 | Hoffberg |
| 9,132,352 B1 | 9/2015 | Rabin et al. |
| 9,151,633 B2 | 10/2015 | Hoffberg |
| 9,215,322 B1 | 12/2015 | Wu et al. |
| 9,239,951 B2 | 1/2016 | Hoffberg et al. |
| 9,311,670 B2 | 4/2016 | Hoffberg |
| 9,419,951 B1 | 8/2016 | Felsher et al. |
| 9,456,086 B1 * | 9/2016 | Wu .................... H04M 3/5233 |
| 9,860,391 B1 * | 1/2018 | Wu .................... H04M 3/5233 |
| 10,237,420 B1 * | 3/2019 | Wu .................... H04M 3/5233 |
| 10,491,748 B1 * | 11/2019 | Wu .................... H04M 3/5233 |
| 2001/0000458 A1 | 4/2001 | Shtivelman et al. |
| 2001/0011228 A1 | 8/2001 | Shenkman |
| 2001/0024497 A1 | 9/2001 | Campbell et al. |
| 2001/0034578 A1 | 10/2001 | Ugajin |
| 2001/0043586 A1 | 11/2001 | Miloslavsky |
| 2002/0006191 A1 | 1/2002 | Weiss et al. |
| 2002/0009190 A1 | 1/2002 | McIllwaine et al. |
| 2002/0018554 A1 * | 2/2002 | Jensen ................ H04M 3/5233 |
| | | 379/265.01 |
| 2002/0019846 A1 | 2/2002 | Miloslavsky et al. |
| 2002/0021693 A1 * | 2/2002 | Bruno .................... H04M 3/51 |
| | | 370/386 |
| 2002/0047859 A1 | 4/2002 | Szlam et al. |
| 2002/0114278 A1 | 8/2002 | Coussement |
| 2002/0116239 A1 | 8/2002 | Reinsma et al. |
| 2002/0131399 A1 | 9/2002 | Philonenko |
| 2002/0174344 A1 * | 11/2002 | Ting ........................ G06F 21/32 |
| | | 713/185 |
| 2003/0002646 A1 | 1/2003 | Gutta et al. |
| 2003/0055895 A1 * | 3/2003 | Peters .................... G06Q 10/10 |
| | | 709/205 |
| 2003/0086554 A1 * | 5/2003 | Krimstock .......... H04M 3/5237 |
| | | 379/265.02 |
| 2003/0095652 A1 * | 5/2003 | Mengshoel ......... H04M 3/5233 |
| | | 379/265.06 |
| 2003/0115088 A1 | 6/2003 | Thompson |
| 2004/0049479 A1 | 3/2004 | Dorne et al. |
| 2004/0081183 A1 | 4/2004 | Monza et al. |
| 2004/0083195 A1 | 4/2004 | McCord et al. |
| 2004/0101127 A1 * | 5/2004 | Dezonno ............... H04M 3/523 |
| | | 379/265.02 |
| 2004/0111310 A1 | 6/2004 | Szlam et al. |
| 2004/0138958 A1 | 7/2004 | Watarai et al. |
| 2004/0141508 A1 | 7/2004 | Schoeneberger et al. |
| 2004/0213400 A1 | 10/2004 | Golitsin et al. |
| 2004/0264677 A1 | 12/2004 | Horvitz et al. |
| 2005/0065837 A1 | 3/2005 | Kosiba et al. |
| 2005/0102221 A1 | 5/2005 | Sulkowski et al. |
| 2005/0129217 A1 | 6/2005 | McPartlan et al. |
| 2005/0195960 A1 | 9/2005 | Shaffer et al. |
| 2005/0251434 A1 | 11/2005 | Ouimet |
| 2006/0062376 A1 | 3/2006 | Pickford |
| 2006/0153356 A1 | 7/2006 | Sisselman et al. |
| 2007/0038498 A1 | 2/2007 | Powell et al. |
| 2007/0064912 A1 | 3/2007 | Kagan et al. |
| 2007/0071222 A1 | 3/2007 | Flockhart et al. |
| 2008/0205501 A1 | 8/2008 | Cioffi et al. |
| 2008/0262893 A1 | 10/2008 | Hoffberg |

\* cited by examiner programmable processor 702

Communications control system 701 computer readable medium 703 a multithreaded operating system, providing support for applications and for passing messages between concurrently executing applications
704 a communications control server application executing under said multithreaded operating system, for controlling concurrent real time communications
705 dynamically linkable application, communicating with the communications control server application to receive call characteristic data and perform a multifactorial optimization with respect to a plurality of target characteristics for each of a plurality of available communications targets, to resolve a an optimal communications target and transmit a resolved communications target, said communications control server application controlling a plurality of concurrent real time communications in dependence on the transmitted resolved communications target
706

Fig. 5

METHOD AND SYSTEM FOR MATCHING ENTITIES IN AN AUCTION

CROSS REFERENCE TO RELATED APPLICATIONS

The present application is a Continuation of U.S. patent application Ser. No. 15/856,729, filed Dec. 28, 2017, now U.S. Pat. No. 10,237,420, issued Mar. 19, 2019, which is a Continuation of U.S. patent application Ser. No. 15/274,744, field Sep. 23, 2016, now U.S. Pat. No. 9,860,391, issued Jan. 2, 2018, which is a Division of U.S. patent application Ser. No. 12/719,827, filed Mar. 8, 2010, now U.S. Pat. No. 9,456,086, issued Sep. 27, 2016, which is a Continuation of U.S. patent application Ser. No. 10/794,749, filed Mar. 5, 2004, now U.S. Pat. No. 7,676,034, which claims benefit of priority from U.S. Provisional Patent Application No. 60/453,273, filed Mar. 7, 2003, each of which is expressly incorporated herein by reference in its entirety.

TECHNICAL FIELD

The present invention relates generally to computer integrated telecommunications systems and more particularly to a system and method employing an intelligent switching architecture.

BACKGROUND OF THE INVENTION

The description of the invention herein is intended to provide information for one skilled in the art to understand and practice the full scope of the invention, but is not intended to be limiting as to the scope of available knowledge, nor admit that any particular reference, nor the combinations and analysis of this information as presented herein, is itself a part of the prior art. It is, in fact, a part of the present invention to aggregate the below cited information as a part of the disclosure, without limiting the scope thereof. All of the below-identified references are therefore expressly incorporated herein by reference, as if the entirety thereof was recited completely herein. It is particularly noted that the present invention is not limited by a narrow or precise discussion herein, nor is it intended that any disclaimer, limitation, or mandatory language as applied to any embodiment or embodiments be considered to limit the scope of the invention as a whole. The scope of the invention is therefore to be construed as the entire literal scope of the claims, as well as any equivalents thereof as provided by law. It is also understood that the title, abstract, field of the invention, and dependent claims are not intended to, and do not, limit the scope of the independent claims.

Real-time communications are typically handled by dedicated systems which assure that the management and control operations are handled in a manner to keep up with the communications process, and to avoid imposing inordinate delays. In order to provide cost-effective performance, complex processes incidental to the management or control of the communication are typically externalized. Thus, the communications process is generally unburdened from tasks requiring a high degree of intelligence, for example the evaluation of complex algorithms and real time optimizations. One possible exception is least cost routing (LCR), which seeks to employ a communications channel which is anticipated to have a lowest cost per unit. In fact, LCR schemes, when implemented in conjunction with a communications switch, either employ simple predetermined rules, or externalize the analysis.

Modern computer telephone integrated systems typically employ a general purpose computer with dedicated voice-communication hardware peripherals, for example boards made by Dialogic, Inc. (Intel Corp.). The voice communication peripherals execute the low level processing and switching of the voice channels, under control from the general purpose processor. Therefore, the voice-information is generally not communicated on the computer bus.

This architecture typically allows the computing platform to run a modern, non-deterministic operating system, such as Windows 2000, without impairing the real-time performance of the system as a whole, since the communications control functions are not as time critical as the voice processing functions. However, as is well known, non-deterministic operating systems, such as Windows 2000, are subject to significant latencies, especially when multiple tasks are executing, and when contention exists between resources, especially hard disk access and virtual memory. Therefore, in order to assure that system operation is unimpeded by inconsistent demands on the platform, typically the host computer system for the telephony peripherals is "dedicated", and attempts are made to eliminate extraneous software tasks. On the other hand, externalizing essential functions imposes potential latencies due to communications and external processing.

The Call Center

A "call center" is an organization of people, telecommunications equipment and management software, with a mission of efficiently handling electronic customer contact. A typical call center must balance competing goals. Customers should experience high quality and consistent service as measured, for example, by how long the customer's call must wait in queue before being answered and receiving satisfactory service. At the same time, this service should be provided to make efficient use of call center resources.

Strategies for Call Center Management

"Workforce management" systems provide important tools for meeting the goals of the call center. These systems generate forecasts of call volumes and call handling times based on historical data, to predict how much staff will be needed at different times of the day and week. The systems then create schedules that match the staffing to anticipated needs.

Typically, an Automatic Call Distribution (ACD) function is provided in conjunction with a computerized Private Branch Exchange (PBX). This ACD function enables a group of agents, termed ACD agents, to handle a high volume of inbound calls and simultaneously allows a queued caller to listen to recordings when waiting for an available ACD agent. The ACD function typically informs inbound callers of their status while they wait and the ACD function routes callers to an appropriate ACD agent on a first-come-first-served basis.

Today, all full-featured PBXs provide the ACD function and there are even vendors who provide switches specifically designed to support the ACD function. The ACD function has been expanded to provide statistical reporting tools, in addition to the call queuing and call routing functions mentioned above, which statistical reporting tools are used to manage the call center. For example, ACD historical reports enable a manager to identify times: (a) when inbound callers abandon calls after long waits in a queue because, for example, the call center is staffed by too few ACD agents and (b) when many ACD agents are idle. In addition, ACD forecasting reports, based on the historical reports, allow the manager to determine appropriate staffing levels for specific weeks and months in the future.

Queue Management

ACD systems experience high traffic periods and low traffic periods. Consequently, ACD systems must be capable of automating two major decisions. The first major decision may be referred to as the "agent selection decision," i.e., when more than one agent is available to handle the next transaction, which agent should be chosen? The second major decision may be referred to as the "transaction selection decision," i.e., when more than one transaction is waiting for the next available agent and an agent becomes available, which transaction should the agent handle?

One approach to the agent selection decision is to set up a sequencing scheme, so that the switch of the ACD system follows the same sequence of agents until the first available agent in the sequence is found. The concern with this approach is that it creates "hot seats," i.e. an inequitable distribution of inbound calls to ACD agents who are high in the sequence. Most current ACD systems solve the agent selection decision by using a longest-idle-eligible-agent approach to provide a more equitable distribution of transactions.

There are also different approaches to the transaction selection decision in which there are more available transactions than there are ACD agents. One approach is to create one or more first-in, first-out (FIFO) queues. Under this approach, each transaction may be marked with a priority level by the switch of the ACD system. When an agent becomes available, the transaction with the highest priority is routed to the agent. If several calls of equal priority are waiting in a queue, the call which has been waiting the longest is routed to the available agent. If the call center conducts outbound transactions, each transaction is similarly submitted to a FIFO queue with a priority designation, with the switch routing transactions from the queue to the agents.

Queue/Team Management

Calls that arrive at a call center generally are classified into "call types" based on the dialed number and possibly other information such as calling number or caller responses to prompts from the network. The call center is typically served by an automatic call distributor (ACD), which identifies the call type of each incoming call and either delivers or queues it. Each call type may have a separate first-in-first-out queue in the ACD. In most existing call centers, the agents answering calls are organized into one or more "teams," with each team having primary responsibility of the calls in one or more queues. This paradigm is sometimes referred to as "queue/team."

In the queue/team model, scheduling for each team can be done independently. Suppose, for example, that the call center handles calls for sales, service, and billing, and that each of these call types is served by a separate team. The schedule for sales agents will depend on the forecast for sales call volume and on various constraints and preferences applicable to the agents being scheduled, but this schedule is not affected by the call volume forecast for service or billing. Further, within the sales team, agents are typically considered interchangeable from a call handling viewpoint. Thus, within a team, schedule start times, break times and the like, may be traded freely among agents in the team to satisfy agent preferences without affecting scheduled call coverage. See, U.S. Pat. No. 5,325,292, expressly incorporated herein by reference.

In a queue/team environment, when a new call arrived, the ACD determines the call type and places it in the queue, if all agents are busy, or allocates this call to the team member who had been available the longest.

Skill-Based Routing

Skill-based routing of agents is a well-known principle, in which the agent with the best match of skills to the problem presented is selected for handling the matter. Typically, these matters involve handling of telephone calls in a call center, and the technology may be applied to both inbound and outbound calling, or a combination of each. The skill-based routing algorithms may also be used to anticipate call center needs, and therefore be used to optimally schedule agents for greatest efficiency, lowest cost, or other optimized variable.

In the case of multi-skill criteria, the optimality of selection may be based on a global minimization of the cost function or the like.

The longest-idle-agent approach and the FIFO approach function well in applications having little variation in the types of transactions being handled by the ACD agents. If all agents can handle any transaction, these approaches provide a sufficiently high level of transactional throughput, i.e., the number of transactions handled by the call center in a particular time interval. However, in many call center environments, the agents are not equally adept at performing all types of transactions. For example, some transactions of a particular call center may require knowledge of a language other than the native language of the country in which the call center is located. As another example, some transactions may require the expertise of "specialists" having training in the specific field to which the transaction relates, since training all agents to be knowledgeable in all areas would be cost-prohibitive. For ACD applications in which agents are not equally adept at performing all transactions, there are a number of problems which at least potentially reduce transactional throughput of the call center. Three such problems may be referred to as the "under-skilled agent" problem, the "over-skilled agent" problem, and the "static grouping" problem.

The under-skilled agent problem reduces transactional throughput when the switch routes transactions to ACD agents who do not have sufficient skills to handle the transactions. For example, a call may be routed to an English-only speaking person, even though the caller only speaks Spanish. In another example, the transaction may relate to product support of a particular item for which the agent is not trained. When this occurs, the agent will typically apologize to the customer and transfer the call to another agent who is capable of helping the customer. Consequently, neither the agent's nor the customer's time is efficiently utilized.

Inefficient utilization is also a concern related to the over-skilled agent problem. A call center may have fixed groupings of agents, with each group having highly trained individuals and less-experienced individuals. Call-management may also designate certain agents as "specialists," since it would be cost prohibitive to train all agents to be experts in all transactions. Ideally, the highly skilled agents handle only those transactions that require a greater-than-average skill level. However, if a significant time passes without transactions that require highly skilled agents, the agents may be assigned to calls for which they are over-qualified. This places the system in a position in which there is no qualified agent for an incoming call requiring a particular expertise because the agents having the expertise are handling calls that do not require such expertise. Again, the transactional throughput of the call center is reduced.

Current ACD systems allow agents to be grouped according to training. For example, a product support call center may be divided into four fixed, i.e., "static," groups, with each group being trained in a different category of products sold by the company. There are a number of potentially negative effects of static grouping. Firstly, the call center management must devise some configuration of agents into groups. This may be a costly process requiring extensive analysis and data entry. Secondly, the configuration that is devised is not likely to be optimal in all situations. The pace and mix of transactions will change during a typical day. At different times, the adverse effects of the under-skilled agent problem and the adverse effects of the over-skilled agent problem will vary with respect to the transactional throughput of the call center. Thirdly, when a new product is released, the devised configuration likely will be less valuable. In response to changes in the size, pace and mix of the transaction load over the course of time, call management must monitor and adjust the performance of the current grouping configuration on an ongoing basis. When trends are detected, the grouping configuration should be changed. This requires the time and attention of call center managers and supervisors. Again, the transactional throughput is reduced.

It is thus known in the prior art to provide ACD systems that depart from the queue/team model described above. Calls are still categorized into call types. In place of queues for the call types, however, queues associated with "skills" are provided. The ACD's call distribution logic for the call type determines which queue or queues a call will occupy at various times before it is answered. Agents are not organized into teams with exclusive responsibility for specific queues. Instead, each agent has one or more identified "skills" corresponding to the skills-based queues. Thus, both a given call and a given agent may be connected to multiple queues at the same time. Agent skills designations may be further qualified, for example, as "primary" or "secondary" skills, or with some other designation of skill priority or degree of skill attainment. The ACD call distribution logic may take the skill priority levels into account in its call distribution logic.

In a skills-based routing environment, the "matching" of calls to agents by the ACD becomes more sophisticated and thus complicated. Agents who have more than one skill no longer "belong" to a well-defined team that handles a restricted set of calls. Instead, the skills definitions form "implicit" teams that overlap in complex ways. If, for example, a call center has 10 skills defined, then agents could in principle have any of 1024 possible combinations ($2^{10}$) of those skills. Each skill combination could be eligible to handle a different subset of the incoming calls, and the eligible subset might vary with time of day, number of calls in queue, or other factors used by the ACD in its call routing decisions.

Today, call center managers want to connect a caller to an ACD agent having exactly the right skills to serve the caller. However, "skills based" ACD agent groups are often small and, as a result, whenever an inbound call arrives, all such "skills based" ACD agents may be busy. In such instances, the ACD function can take call back instructions from the caller and the ACD function can manage the call back functions, for example, by assigning such calls, in accordance with the caller instructions, to a "skills based" ACD agent whenever one becomes available.

Scheduling of agents in a skills-based environment is thus a much more difficult problem than it is in a queue/team environment. In a skills-based environment, call types cannot be considered in isolation. Thus, for example, a heavy volume of Service calls might place higher demands on multi-skilled agents, causing an unforeseen shortage of coverage for Billing calls. Further, agents with different skills cannot be considered interchangeable for call handling. Thus, trading lunch times between a Sales-only agent and a multi-skill agent might lead to over-staffing Sales at noon while under-staffing Service at 1:00 p.m. This would lead to undesirable results. Moreover, with respect to the needs of a particular call type, a multi-skilled agent might provide no help over a given span of time, might be 100% available for calls of that type, or might be available part of the time and handling other call types for another part of time.

All agents having a particular combination of skills may be deemed a "skill group." A central problem of skills-based scheduling is then finding a way to predict what fraction of scheduled agents from each skill group will be available to each call type during each time interval being scheduled. If these fractions are known, then the effect of different agent schedules can be generated. Unfortunately, it is difficult or impossible to calculate the skill group availability fractions directly. These functions depend on the relative and absolute call volumes in each call type, on the particulars of the skills-based call distribution algorithms in the ACD, and on the skills profiles of the total scheduled agent population. Particularly as ACD skills-based routing algorithms themselves evolve and become more sophisticated, the factors affecting skill group availability become too complex for direct analysis. One proposed solution provides a feedback mechanism involving call handling simulation and incremental scheduling, to schedule agents in a skills-based routing environment. See, U.S. Pat. No. 6,044,355, expressly incorporated herein in its entirety.

In accordance with this "skills-based scheduling" method, a computer implemented tool is used to determine an optimum schedule for a plurality of scheduled agents in a telephone call center, each of the plurality of scheduled agents having a combination of defined skills. The plurality of scheduled agents are organized into "skill groups" with each group including all scheduled agents having a particular combination of skills. The method begins by generating a plurality of net staffing arrays, each net staff array associated with a given call type and defining, for each time interval to be scheduled, an estimate of a difference between a given staffing level and a staffing level needed to meet a current call handling requirement. In addition to the net staffing arrays, the method uses a plurality of skills group availability arrays, each skills group availability array associated with the given call type and defining, for each combination of skill group and time interval to be scheduled, an estimate of a percentage of scheduled agents from each skill group that are available to handle a call. According to the method, the plurality of arrays are used to generate a proposed schedule for each of the plurality of scheduled agents. Thereafter, a call handling simulation is then run against the proposed schedule using a plurality of ACD call distribution algorithms (one for each call type being scheduled). Based on the results of the call handling simulation, the net staffing arrays and the skills availability arrays are refined to more accurately define the net staffing and skills usage requirements. The process of generating a schedule and then testing that schedule through the simulator is then repeated until a given event occurs. The given event may be a determination that the schedule meets some given acceptance criteria, a passage of a predetermined period of time, a predetermined number of iterations of the process, or some combination thereof. A proposed schedule is "optimized" when it provides an acceptable call handling performance level and an acceptable staffing level in the simulation. Once the proposed schedule is "optimized," it may be further adjusted (within a particular skill group) to accommodate agent preferences.

U.S. Pat. No. 5,206,903 to Kohler et al. describes ACD equipment which uses static grouping. Each static group of agents is referred to as a "split," and each split is associated with a different queue. The agents are assigned to splits according to skills. Within a single split, the agents may be limited to knowledge of different subtypes of transactions. Preferably, there is at least one agent in each split who is trained to handle calls of any of the subtypes within the particular split. This "expert" may also be trained to efficiently handle calls of other types, i.e., other splits. Each agent possesses up to four skill numbers that represent various abilities of the agent with respect to handling transactions related to subtypes and types of transactions. The ACD equipment assigns each incoming call three prioritized skill numbers that estimate skill requirements of the incoming call. The skill numbers of the incoming call are considered "prioritized," since they are viewed sequentially in searching for a match of the call with an agent, so that the second skill number of the call is unnecessary if a match is found using the first prioritized skill number. The incoming call is assigned the one, two or three prioritized skill numbers and is placed in the appropriate queue of the appropriate static group of agents. A search is made among the available agents for an agent-skill number that matches the first skill number of the call. If no match is found after a predetermined time delay, the second prioritized skill number of the call is used to find a match. If no match is found after a second predetermined time delay, the third prioritized skill number is considered. Then, if no match is still found, the ACD equipment of Kohler et al. expands the search of available agents to other groups of agents.

While the Kohler et al. patent does not directly address the problems associated with static groups, it does consider the skills of the individual agents. The prioritized skill numbers assigned to the incoming calls are logically ordered. The patent refers to the first skill number of a call as the primary call-skill indicator. This primary indicator is used to define the minimal skill level that is required for an agent to competently handle the call. Consequently, if a match is made with the primary indicator, the ACD agent may not be over-skilled or under-skilled. However, if the search is unsuccessful, the secondary call-skill indicator is utilized. The search for a match to the secondary indicator may cause the call to be routed to an agent having more than the minimal required skill. The third prioritized skill number that is assigned to the incoming call is referred to as the "tertiary" call-skill indicator. The tertiary indicator is yet another skill level beyond what is minimally required to competently handle a call. Since the tertiary indicator is utilized only if a match is not found for either of the primary or secondary indicators, an overly skilled agent of the appropriate group will handle the call only if that agent is the only available capable agent. Thus, more highly skilled agents are assigned only when their skills are required, or no lesser-skilled agent is available to handle the call. See, 6453038; 6459784; 6463299; 6466654; 6466909; 6470077; 6477245; 6477494; 6487533; 6493432; 6493696; 6496568; 6510221; 6519259; 6519459; 6522726; 6529870; and 20030002646.

Group Routing

Various types of conventional automatic call distributors (ACDs) are available to distribute incoming calls to a group. Reservation and information services may be provided by large companies, such as major airlines, and may consist of geographically separated groups of agents that answer incoming calls distributed to the agents by separate ACDs. Agent communication terminals (ACTs) which are connected to an ACD are utilized by the agents to process incoming calls routed to a particular ACT by the ACD.

A public branch exchange (PBX) type ACD such as a Definity® ACD available from AT&T functions as a conventional PBX and further functions as an ACD to distribute incoming calls to local agents connected to the PBX. Another type of ACD consists of the utilization of an electronic telecommunication switch such as a 5ESS® switch available from AT&T which is capable of providing ACD service when supposed by ACTs coupled to the switch. Both types of ACD typically function as independent systems which handle incoming calls and make internal decisions concerning which agent will receive a given call. Both types of ACD systems are capable of generating statistical reports which can be monitored by a workstation coupled to the ACD system to allow a supervisor to monitor call handling statistics. Such data typically represents an average of statistics for a given system.

Telephone call centers that handle calls to toll-free "800" numbers are well-known in the art. Typically, a company may have many call centers, all answering calls made to the same set of 800 numbers. Each of the company's call centers usually has an automatic call distributor (ACD) or similar equipment capable of queuing calls. ACD management information systems keep statistics on agent and call status, and can report these statistics on frequent intervals. Such capabilities are in use today for centralized reporting and display of multi-location call center status.

In such systems, the company will want to distribute the calls to its call centers in a way that will optimally meet its business goals. Those goals might include low cost of call handling, answering most calls within a given amount of time, providing customized handling for certain calls, and many others. It is also known in the prior art that certain call routing criteria and techniques support a broad range of business goals. These include "load balancing," "caller segmentation" and "geographic routing." Load balancing refers to distribution of calls so that the expected answer delay for new calls is similar across all the call centers. If other considerations do not dictate otherwise, load balancing is desirable because it provides optimum efficiency in the use of agents and facilities, and it provides the most consistent grade of service to callers. In special situations it might be desirable to unbalance the load in a particular way, but control over the distribution of call load is still desired.

If the caller's identity can be inferred from the calling number, caller-entered digits, or other information, that identity may influence the choice of destination for the call. Call routing based on such information is referred to as caller segmentation. Also, it has been found desirable for particular call centers to handle calls from particular geographic areas. The motivation may be to minimize call transport costs, to support pre-defined call center "territories", or to take advantage of agents specifically trained to handle calls from given locations. Such techniques are known as geographic routing.

The interexchange carriers who provide 800 service today generally support some form of "routing plan" to help achieve load balancing, caller segmentation and geographic routing. Typically, these routing plans allow 800 call routing based on time of day, day of week, the caller's area code, caller-entered digits, and fixed percentage allocations. Predominately, however, the routing plans supported by the carriers are static in the sense that they do not automatically react to unexpected variations in incoming call volume or distribution, nor to actual call delays being experienced at each destination. Reaction to changing conditions is done via manual modification of the plan, on a time scale of minutes or hours.

Recent service offerings from some interexchange carriers offer some degree of automatic reaction to changing conditions. One such offering, called "alternate termination sequence" or "ATS" (from AT&T), allows customers to establish maximum numbers of calls to be queued for each destination, with a pre-defined alternative when a primary destination is overloaded. Another offering, referred to as "intelligent routing control" or "IRC" (from MCI), allows an ACD to refuse a call from the network, again resulting in pre-defined alternative call handling. A third kind of service, AT&T's Intelligent Call Processing, lets the interexchange network pass call-by-call data to a computer.

In a conventional ACD, phone calls are processed on a first-in, first-out basis: the longest call waiting is answered by the next available agent. Answering calls across multiple automated call distributors (ACD) is typically done on a first-in, first-out basis dependent upon time of receipt of the call by each ACD, whether the call is directly connected or forwarded.

Another call distribution scheme is provided in Gechter et al., U.S. Pat. No. 5,036,535. This patent discloses a system for automatically distributing telephone calls placed over a network to one of a plurality of agent stations connected to the network via service interfaces, and providing status messages to the network. Gechter et al.'s disclosed system includes means for receiving the agent status messages and call arrival messages from the network, which means are connected via a network service interface to the network. Routing means responsive to the receiving means is provided for generating a routing signal provided to the network to connect the incoming call to an agent station through the network. In the system disclosed in Gechter et al, when an incoming call is made to the call router, it decides which agent station should receive the call, establishes a call with that agent station, and then transfers the original call onto the second call to connect the incoming caller directly to the agent station and then drops out of the connection.

U.S. Pat. No. 5,193,110 issued to Jones et al discloses an integrated services platform for a telephone communications system which platform includes a plurality of application processing ports for providing different types of information services to callers. In Jones et al.'s disclosed system, a master control unit and a high speed digital switch are used to control processing of incoming phone calls by recognizing the type of service requested by the caller and then routing the call to the appropriate processing port. The Jones et al system is disclosed as an adjunct to current switching technology in public and private networks.

Intelligent Call Management

Call centers are also used to make outbound calls, for example for telemarketing. Agents making outbound calls, referred to as outbound agents, are typically separate from ACD agents handling inbound calls and call center software separately manages outbound call lists for outbound agents to ensure that each outbound agent wastes little time in dialing or in performing overhead operations.

A call center typically has multiple agents for answering incoming calls and placing outgoing calls. A call center may also have agents participating in outgoing call campaigns, typically in conjunction with an outbound call management system. Each agent may be assigned to a particular group, such as an inbound group or an outbound group. Agents can also be assigned to a supervisor team, which represents multiple agents that report to the same supervisor.

In certain situations, it is necessary to restrict an agent's activity to answering calls or handling a particular type of call (e.g., answering only incoming calls). For example, during an outbound campaign, the system placing the outbound calls and controlling the rate at which the calls are placed, e.g., a so-called predictive dialer, relies on the availability of the agent to handle an answered call. If the system places outbound calls expecting the agent to be available, but the agent instead places their own call to another agent or a supervisor, or has an incoming call connected to them, the outbound system may not have an agent available to handle an answered outbound call. Additionally, if an agent is assigned to handle incoming calls, but instead places a call to another agent or listens to voice mail messages, the number of queued incoming calls may increase, thereby increasing the waiting time experienced by the callers.

One document which provides considerable information on intelligent networks is "ITU-T Recommendation Q.1219, Intelligent Network User's Guide for Capability Set 1", dated April, 1994. This document is incorporated herein by reference.

One known system proposes a call-management method and system for distributing calls to a plurality of individuals, such as automatic call distribution (ACD) agents, which routes calls to the individuals based upon a correlation of attributes of the individuals with calls that are tagged with identification of abilities that are advantageous to efficiently processing the calls. That is, for each call that is to be distributed, one or more skills that are relevant to efficient handling of the call are determined and then used to route the call to an appropriate individual. In addition, call management preferences may also be accommodated.

Personalization and Collaborative Filtering

Known systems allow personalization or prediction of user type, preferences or desires based on historical data or limited information available. These known systems have been applied to a number of different domains.

In a non-collaborative personalization system, the available information about a person is analyzed, and based on this information, conclusions are drawn. In a collaborative system, the available information is used to associate the person with a group of other users having common attributes. By grouping users, the data sets are more dense, permitting more detailed inferences to be drawn. The groups are defined by mapping user attributes in a multidimensional space, and then defining clusters of users having correlated traits. Further, the use of data relating to past transactions of other users allows prediction of outcomes and sequences of actions, without having a true past example of the activity from that particular user.

The following references are expressly incorporated herein by reference: U.S. Pat. Nos. 5,560,011; 5,774,357; 5,790,935; 5,867,386; 5,867,799; 5,875,108; 5,901,246; 5,903,454; 5,920,477; 5,983,214; 5,999,908; 6,006,218; 6,016,475; 6,018,738; 6,029,161; 6,078,928; 6,081,750; 6,112,181; 6,112,186; 6,138,119; 6,144,964; 6,146,026; 6,170,742; 6,177,932; 6,185,683; 6,236,978; 6,236,980; 6,253,193; 6,256,648; 6,266,649; 6,308,175; 6,314,420; 6,317,718; 6,317,722; 6,321,179; 6,321,221; 6,327,590; 6,334,127; 6,334,131; 6,345,264; 6,353,813; 6,356,899; 6,389,372; 6,400,996; 6,405,922; 6,412,012; 6,418,424; 6,421,709; 6,430,558; 6,446,035; 6,449,367; 6,466,970; 6,477,246; 6,480,844; 6,484,123; and 6,529,891. See References, below. See, also U.S. Pat. Nos. 4,048,452; 4,737, 983, 4,757,529; 4,893,301; 4,953,204; 5,073,890; 5,278, 898; 5,309,513; 5,369,695; 5,506,898; 5,511,117; 5,519, 773; 5,524,147; 5,590,188; 5,633,922; 5,633,924; 5,715, 307; 5,740,240; 5,768,360; 5,825,869; 5,848,143; 5,870, 464; 5,878,130; 5,901,214; 5,905,792; 5,907,608; 5,910, 982; 5,915,011; 5,917,903; 5,923,745; 5,926,539; 5,933, 492; 5,940,496, 5,940,947; 5,946,387; 5,953,332; 5,953, 405; 5,956,397; 5,960,073; 5,963,632; 5,970,134; 5,978, 465; 5,982,868; 5,987,116; 5,987,118; 5,991,391; 5,991, 392; 5,991,395; 5,995,614; 5,995,615; 5,999,965; 6,002, 760; 6,005,931; 6,044,146; 6,058,435; 6,061,347; 6,064, 667; 6,072,864; 6,104,801; 6,115,462; 6,118,865; 6,122, 358; 6,122,360; 6,122,364; 6,128,380; 6,134,530; 6,147, 975; 6,157,655; 6,175,563; 6,175,564; 6,185,292; 6,223, 165; 6,226,289; 6,229,888; 6,230,197; 6,233,332, 6,333, 979; 6,333,980; 6,347,139; and U.S. Patent Application Nos. 010000458 A1; 0010024497 A1; 0020006191 A1; 0020009190 A1; 0020019846 A1; and 0020021693 A1, each of which is expressly incorporated herein by reference.

Internet Auctions

On-line electronic auction systems which allow efficient sales of products and services are well known, for example, EBAY.COM, ONSALE.COM, UBID.COM, and the like. Inverse auctions that allow efficient purchases of product are also known, establishing a market price by competition between sellers. The Internet holds the promise of further improving efficiency of auctions by reducing transaction costs and freeing the "same time-same place" limitations of traditional auctions. This is especially appropriate where the goods may be adequately described by text or images, and thus a physical examination of the goods is not required prior to bidding.

In existing Internet systems, the technological focus has been in providing an auction system that, over the course of hours to days, allow a large number of simultaneous auctions, between a large number of bidders to occur. These systems must be scalable and have high transaction throughput, while assuring database consistency and overall system reliability. Even so, certain users may selectively exploit known technological limitations and artifacts of the auction system, including non-real time updating of bidding information, especially in the final stages of an auction.

Because of existing bandwidth and technological hurdles, Internet auctions are quite different from live auctions with respect to psychological factors. Live auctions are often monitored closely by bidders, who strategically make bids, based not only on the "value" of the goods, but also on an assessment of the competition, timing, psychology, and progress of the auction. It is for this reason that so-called proxy bidding, wherein the bidder creates a preprogrammed "strategy", usually limited to a maximum price, are disfavored. A maximum price proxy bidding system is somewhat inefficient, in that other bidders may test the proxy, seeking to increase the bid price, without actually intending to purchase, or contrarily, after testing the proxy, a bidder might give up, even below a price he might have been willing to pay. Thus, the proxy imposes inefficiency in the system that effectively increases the transaction cost.

In order to address a flurry of activity that often occurs at the end of an auction, an auction may be held open until no further bids are cleared for a period of time, even if advertised to end at a certain time. This is common to both live and automated auctions. However, this lack of determinism may upset coordinated schedules, thus impairing efficient business use of the auction system.

In order to facilitate management of bids and bidding, some of the Internet auction sites have provided non-Hypertext Markup Language (HTML) browser based software "applet" to track auctions. For example, ONSALE.COM has made available a Marimba Castanet® applet called Bidwatch to track auction progress for particular items or classes of items, and to facilitate bidding thereon. This system, however, lacks real-time performance under many circumstances, having a stated refresh period of 10 seconds, with a long latency for confirmation of a bid, due to constraints on software execution, quality of service in communications streams, and bid confirmation dialogue. Thus, it is possible to lose a bid even if an attempt was made prior to another bidder. The need to quickly enter the bid, at risk of being too late, makes the process potentially error prone.

Proxy bidding, as discussed above, is a known technique for overcoming the constraints of Internet communications and client processing limitations, since it bypasses the client and telecommunications links and may execute solely on the host system or local thereto. However, proxy bidding undermines some of the efficiencies gained by a live market.

U.S. Pat. No. 5,890,138 to Godin, et al. (Mar. 30, 1999), expressly incorporated herein by reference in its entirety, relates to an Internet auction system. The system implements a declining price auction process, removing a user from the auction process once an indication to purchase has been received. See, Rockoff, T. E., Groves, M.; "Design of an Internet-based System for Remote Dutch Auctions", Internet Research, v 5, n 4, pp. 10-16, MCB University Press, Jan. 1, 1995.

A known computer site for auctioning a product on-line comprises at least one web server computer designed for serving a host of computer browsers and providing the browsers with the capability to participate in various auctions, where each auction is of a single product, at a specified time, with a specified number of the product available for sale. The web server cooperates with a separate database computer, separated from the web server computer by a firewall. The database computer is accessible to the web computer server computer to allow selective retrieval of product information, which includes a product description, the quantity of the product to be auctioned, a start price of the product, and an image of the product. The web server computer displays, updated during an auction, the current price of the product, the quantity of the product remaining available for purchase and the measure of the time remaining in the auction. The current price is decreased in a predetermined manner during the auction. Each user is provided with an input instructing the system to purchase the product at a displayed current price, transmitting an identification and required financial authorization for the purchase of the product, which must be confirmed within a predetermined time. In the known system, a certain fall-out rate in the actual purchase confirmation may be assumed, and therefore some overselling allowed. Further, after a purchase is indicate, the users screen is not updated, obscuring the ultimate lowest selling price from the user. However, if the user maintains a second browser, he can continue to monitor the auction to determine whether the product could have been purchased at a lower price, and if so, fail to confirm the committed purchase and purchase the same goods at a lower price while reserving the goods to avoid risk of loss. Thus, the system is flawed, and may fail to produce an efficient transaction or optimal price.

An Internet declining price auction system may provide the ability to track the price demand curve, providing valuable marketing information. For example, in trying to determine the response at different prices, companies normally have to conduct market surveys. In contrast, with a declining price auction, substantial information regarding price and demand is immediately known. The relationship between participating bidders and average purchasers can then be applied to provide a conventional price demand curve for the particular product.

U.S. Pat. No. 5,835,896, Fisher, et al., issued Nov. 10, 1998, expressly incorporated herein by reference in its entirety, provides method and system for processing and transmitting electronic auction information over the Internet, between a central transaction server system and remote bidder terminals. Those bids are recorded by the system and the bidders are updated with the current auction status information. When appropriate, the system closes the auction from further bidding and notifies the winning bidders and losers as to the auction outcome. The transaction server posts information from a database describing a lot available for purchase, receives a plurality of bids, stored in a bid database, in response to the information, and automatically categorizes the bids as successful or unsuccessful. Each bid is validated, and an electronic mail message is sent informing the bidder of the bid status. This system employs HTTP, and thus does not automatically update remote terminal screens, requiring the e-mail notification feature.

The auction rules may be flexible, for example including Dutch-type auctions, for example by implementing a price markdown feature with scheduled price adjustments, and English-type (progressive) auctions, with price increases corresponding to successively higher bids. In the Dutch type auction, the price markdown feature may be responsive to bidding activity over time, amount of bids received, and number of items bid for. Likewise, in the progressive auction, the award price may be dependent on the quantity desired, and typically implements a lowest successful bid price rule. Bids that are below a preset maximum posted selling price are maintained in reserve by the system. If a certain sales volume is not achieved in a specified period of time, the price is reduced to liquidate demand above the price point, with the new price becoming the posted price. On the other hand, if a certain sales volume is exceeded in a specified period of time, the system may automatically increase the price. These automatic price changes allow the seller to respond quickly to market conditions while keeping the price of the merchandise as high as possible, to the sellers benefit. A "Proxy Bidding" feature allows a bidder to place a bid for the maximum amount they are willing to pay, keeping this value a secret, displaying only the amount necessary to win the item up to the amount of the currently high bids or proxy bids of other bidders. This feature allows bidders to participate in the electronic auction without revealing to the other bidders the extent to which they are willing to increase their bids, while maintaining control of their maximum bid without closely monitoring the bidding. The feature assures proxy bidders the lowest possible price up to a specified maximum without requiring frequent inquiries as to the state of the bidding.

A "Floating Closing Time" feature may also be implemented whereby the auction for a particular item is automatically closed if no new bids are received within a predetermined time interval, assuming an increasing price auction. Bidders thus have an incentive to place bids expeditiously, rather than waiting until near the anticipated close of the auction.

U.S. Pat. No. 5,905,975, Ausubel, issued May 18, 1999, expressly incorporated herein by reference in its entirety, relates to computer implemented methods and apparatus for auctions. The proposed system provides intelligent systems for the auctioneer and for the user. The auctioneer's system contains information from a user system based on bid information entered by the user. With this information, the auctioneer's system determines whether the auction can be concluded or not and appropriate messages are transmitted. At any point in the auction, bidders are provided the opportunity to submit not only their current bids, but also to enter future bids, or bidding rules which may have the opportunity to become relevant at future times or prices, into the auction system's database. Participants may revise their executory bids, by entering updated bids. Thus, at one extreme, a bidder who wishes to economize on his time may choose to enter his entire set of bidding rules into the computerized system at the start of the auction, effectively treating this as a sealed-bid auction. At the opposite extreme, a bidder who wishes to closely participate in the auction may choose to constantly monitor the auction's progress and to submit all of his bids in real time. See also, U.S. patent application Ser. No. 08/582,901 filed Jan. 4, 1996, which provides a method for auctioning multiple, identical objects and close substitutes.

E-Commerce Systems

U.S. Pat. No. 5,946,669 (Polk, Aug. 31, 1999), expressly incorporated herein by reference, relates to a method and apparatus for payment processing using debit-based electronic funds transfer and disbursement processing using addendum-based electronic data interchange. This disclosure describes a payment and disbursement system, wherein an initiator authorizes a payment and disbursement to a collector and the collector processes the payment and disbursement through an accumulator agency. The accumulator agency processes the payment as a debit-based transaction and processes the disbursement as an addendum-based transaction. The processing of a debit-based transaction generally occurs by electronic funds transfer (EFT) or by financial electronic data interchange (FEDI). The processing of an addendum-based transaction generally occurs by electronic data interchange (EDI).

U.S. Pat. No. 6,005,939 (Fortenberry, et al., Dec. 21, 1999), expressly incorporated herein by reference, relates to a method and apparatus for storing an Internet user's identity and access rights to World Wide Web resources. A method and apparatus for obtaining user information to conduct secure transactions on the Internet without having to re-enter the information multiple times is described. The method and apparatus can also provide a technique by which secured access to the data can be achieved over the Internet. A passport containing user-defined information at various security levels is stored in a secure server apparatus, or passport agent, connected to computer network. A user process instructs the passport agent to release all or portions of the passport to a recipient node and forwards a key to the recipient node to unlock the passport information.

U.S. Pat. No. 6,016,484 (Williams, et al., Jan. 18, 2000), expressly incorporated herein by reference, relates to a system, method and apparatus for network electronic payment instrument and certification of payment and credit collection utilizing a payment. An electronic monetary system provides for transactions utilizing an electronic-monetary system that emulates a wallet or a purse that is customarily used for keeping money, credit cards and other forms of payment organized. Access to the instruments in the wallet or purse is restricted by a password to avoid unauthorized payments. A certificate form must be completed in order to obtain an instrument. The certificate form obtains the information necessary for creating a certificate granting authority to utilize an instrument, a payment holder and a complete electronic wallet. Electronic approval results in the generation of an electronic transaction to complete the order. If a user selects a particular certificate, a particular payment instrument holder will be generated based on the selected certificate. In addition, the issuing agent for the certificate defines a default bitmap for the instrument associated with a particular certificate, and the default bitmap will be displayed when the certificate definition is completed. Finally, the number associated with a particular certificate will be utilized to determine if a particular party can issue a certificate.

U.S. Pat. No. 6,029,150 (Kravitz, Feb. 22, 2000), expressly incorporated herein by reference, relates to a system and method of payment in an electronic payment system wherein a plurality of customers have accounts with an agent. A customer obtains an authenticated quote from a specific merchant, the quote including a specification of goods and a payment amount for those goods. The customer sends to the agent a single communication including a request for payment of the payment amount to the specific merchant and a unique identification of the customer. The agent issues to the customer an authenticated payment advice based only on the single communication and secret shared between the customer and the agent and status information, which the agent knows about the merchant, and/or the customer. The customer forwards a portion of the payment advice to the specific merchant. The specific merchant provides the goods to the customer in response to receiving the portion of the payment advice.

U.S. Pat. No. 6,047,269 (Biffar, Apr. 4, 2000), expressly incorporated herein by reference, relates to a self-contained payment system with creating and facilitating transfer of circulating digital vouchers representing value. A digital voucher has an identifying element and a dynamic log. The identifying element includes information such as the transferable value, a serial number and a digital signature. The dynamic log records the movement of the voucher through the system and accordingly grows over time. This allows the system operator to not only reconcile the vouchers before redeeming them, but also to recreate the history of movement of a voucher should an irregularity like a duplicate voucher be detected. These vouchers are used within a self-contained system including a large number of remote devices that are linked to a central system. The central system can be linked to an external system. The external system, as well as the remote devices, is connected to the central system by any one or a combination of networks. The networks must be able to transport digital information, for example the Internet, cellular networks, telecommunication networks, cable networks or proprietary networks. Vouchers can also be transferred from one remote device to another remote device. These remote devices can communicate through a number of methods with each other. For example, for a non-face-to-face transaction the Internet is a choice, for a face-to-face or close proximity transactions tone signals or light signals are likely methods. In addition, at the time of a transaction a digital receipt can be created which will facilitate a fast replacement of vouchers stored in a lost remote device.

Micropayments

U.S. Pat. No. 5,999,919 (Jarecki, et al., Dec. 7, 1999), expressly incorporated herein by reference, relates to an efficient micropayment system. Existing software proposals for electronic payments can be divided into "on-line" schemes which require participation of a trusted party (the bank) in every transaction and are secure against overspending, and "off-line" schemes which do not require a third party and guarantee only that overspending is detected when vendors submit their transaction records to the bank (usually at the end of the day). A new "hybrid" scheme is proposed which combines the advantages of both "on-line" and "off-line" electronic payment schemes. It allows for control of overspending at a cost of only a modest increase in communication compared to the off-line schemes. The protocol is based on probabilistic polling. During each transaction, with some small probability, the vendor forwards information about this transaction to the bank. This enables the bank to maintain an accurate approximation of a customer's spending. The frequency of polling messages is related to the monetary value of transactions and the amount of overspending the bank is willing to risk. For transactions of high monetary value, the cost of polling approaches that of the on-line schemes, but for micropayments, the cost of polling is a small increase over the traffic incurred by the off-line schemes.

Micropayments are often preferred where the amount of the transaction does not justify the costs of complete financial security. In the micropayment scheme, typically a direct communication between creditor and debtor is not required; rather, the transaction produces a result which eventually results in an economic transfer, but which may remain outstanding subsequent to transfer of the underlying goods or services. The theory underlying this micropayment scheme is that the monetary units are small enough such that risks of failure in transaction closure is relatively insignificant for both parties, but that a user gets few chances to default before credit is withdrawn. On the other hand, the transaction costs of a non-real time transactions of small monetary units are substantially less than those of secure, unlimited or potentially high value, real time verified transactions, allowing and facilitating such types of commerce. Thus, the rights management system may employ applets local to the client system, which communicate with other applets and/or the server and/or a vendor/rights-holder to validate a transaction, at low transactional costs.

The following U.S. Patents, expressly incorporated herein by reference, define aspects of micropayment, digital certificate, and on-line payment systems: U.S. Pat. Nos. 5,666, 416; 5,677,955; 5,717,757; 5,793,868; 5,815,657; 5,839, 119; 5,857,023; 5,884,277; 5,903,651; 5,903,880; 5,915, 093; 5,930,777; 5,933,498; 5,937,394; 5,960,083; 5,963, 924; 5,987,132; 5,996,076; 6,016,484; 6,018,724; 6,021, 202; 6,035,402; 6,049,786; 6,049,787; 6,057,872; 6,058, 381; 6,061,448; 6,061,665. See also, Rivest and Shamir, "PayWord and MicroMint: Two Simple Micropayment Schemes" (May 7, 1996); Micro PAYMENT transfer Protocol (MPTP) Version 0.1 (22 Nov. 1995) et seq., www.w3.org/pub/WWW/TR/WD-mptp; Common Markup for web Micropayment Systems, www.w3.org/TR/WD-Micropayment-Markup (9 Jun. 1999); "Distributing Intellectual Property: a Model of Microtransaction Based Upon Metadata and Digital Signatures", Olivia, Maurizio, olivia-.modlang.denison.eduholivia/RFC/09/, all of which are expressly incorporated herein by reference. See, also: U.S. Pat. Nos. 4,977,595; 5,224,162; 5,237,159; 5,392,353; 5,511,121; 5,621,201; 5,623,547; 5,679,940; 5,696,908; 5,754,939; 5,768,385; 5,799,087; 5,812,668; 5,828,840; 5,832,089; 5,850,446; 5,889,862; 5,889,863; 5,898,154; 5,901,229; 5,920,629; 5,926,548; 5,943,424; 5,949,045; 5,952,638; 5,963,648; 5,978,840; 5,983,208; 5,987,140; 6,002,767; 6,003,765; 6,021,399; 6,026,379; 6,029,150; 6,029,151; 6,047,067; 6,047,887; 6,055,508; 6,065,675; 6,072,870; each of which is expressly incorporated herein by reference. See Also References, below. See also, U.S. Pat.

Nos. 4,286,118; 4,677,663; 4,768,221; 4,797,911; 4,807,279; 4,852,149; 4,866,754; 4,878,243; 4,894,857; 4,924,501; 4,930,150; 4,933,964; 4,935,956; 4,941,168; 4,958,371; 4,975,841; 4,979,171; 4,987,587; 4,998,272; 5,007,000; 5,007,078; 5,014,298; 5,016,270; 5,020,095; 5,020,097; 5,040,208; 5,048,075; 5,063,522; 5,070,525; 5,070,526; 5,073,929; 5,077,789; 5,081,711; 5,097,528; 5,103,449; 5,121,422; 5,128,984; 5,161,181; 5,163,083; 5,163,087; 5,164,981; 5,166,974; 5,168,517; 5,185,786; 5,214,688; 5,218,635; 5,224,153; 5,239,574; 5,251,252; 5,253,289; 5,276,732; 5,283,818; 5,289,530; 5,297,146; 5,297,195; 5,309,504; 5,309,505; 5,311,574; 5,311,577; 5,313,516; 5,319,703; 5,321,745; 5,327,490; 5,329,579; 5,333,190; 5,341,412; 5,341,414; 5,351,285; 5,359,645; 5,365,575; 5,381,470; 5,390,236; 5,400,393; 5,402,474; 5,420,852; 5,420,919; 5,425,093; 5,430,792; 5,432,835; 5,434,906; 5,436,967; 5,442,693; 5,448,624; 5,448,631; 5,459,781; 5,465,286; 5,467,391; 5,479,487; 5,479,501; 5,481,596; 5,485,506; 5,493,690; 5,495,523; 5,495,528; 5,502,762; 5,506,898; 5,511,112; 5,515,421; 5,517,566; 5,519,773; 5,524,140; 5,526,417; 5,528,666; 5,530,931; 5,533,103; 5,533,107; 5,533,109; 5,535,257; 5,537,470; 5,544,220; 5,544,232; 5,546,452; 5,546,456; 5,555,290; 5,555,295; 5,557,668; 5,559,867; 5,559,878; 5,561,711; 5,568,540; 5,570,419; 5,572,576; 5,572,586; 5,574,784; 5,577,112; 5,579,377; 5,579,383; 5,581,602; 5,581,604; 5,581,607; 5,586,179; 5,588,049; 5,590,171; 5,592,543; 5,594,790; 5,594,791; 5,600,710; 5,610,774; 5,610,978; 5,619,557; 5,625,676; 5,625,682; 5,633,917; 5,636,267; 5,636,268; 5,638,436; 5,646,986; 5,646,988; 5,652,788; 5,655,013; 5,655,014; 5,657,074; 5,661,283; 5,675,637; 5,684,863; 5,687,225; 5,692,033; 5,692,034; 5,696,809; 5,696,818; 5,699,418; 5,701,295; 5,703,935; 5,717,741; 5,724,418; 5,727,154; 5,729,600; 5,740,233; 5,742,675; 5,748,711; 5,761,285; 5,768,355; 5,774,537; 5,787,156; 5,787,159; 5,793,846; 5,796,791; 5,796,816; 5,799,077; 5,806,071; 5,812,642; 5,815,551; 5,815,554; 5,815,566; 5,822,400; 5,822,401; 5,822,410; 5,825,869; 5,828,731; 5,828,734; 5,835,572; 5,838,772; 5,838,779; 5,841,852; 5,848,143; 5,850,428; 5,854,832; 5,857,013; 5,867,559; 5,867,564; 5,867,572; 5,872,833; 5,878,126; 5,893,902; 5,894,505; 5,896,446; 5,898,759; 5,898,762; 5,901,209; 5,903,641; 5,905,979; 5,907,601; 5,912,947; 5,913,195; 5,914,951; 5,917,893; 5,918,213; 5,923,746; 5,924,016; 5,926,528; 5,930,339; 5,933,480; 5,937,055; 5,937,390; 5,940,493; 5,940,497; 5,940,813; 5,943,403; 5,946,388; 5,946,394; 5,949,852; 5,949,854; 5,949,863; 5,956,392; 5,963,635; 5,966,429; 5,970,132; 5,974,120; 5,974,135; 5,978,465; 5,978,467; 5,978,471; 5,982,857; 5,987,115; 5,987,116; 5,991,393; 5,991,604; 5,991,761; 5,995,948; 6,002,760; 6,005,534; 6,005,928; 6,009,149; 6,011,845; 6,014,439; 6,016,344; 6,018,579; 6,021,114; 6,021,190; 6,021,428; 6,026,149; 6,026,156; 6,031,899; 6,035,021; 6,041,116; 6,041,118; 6,044,135; 6,044,149; 6,044,368; 6,049,599; 6,052,453; 6,055,307; 6,058,435; 6,064,730; 6,064,731; 6,064,973; 6,067,348; 6,070,142; 6,084,943; 6,097,806; 6,098,069; 6,102,970; 6,115,693; 6,122,358; 6,122,364; 6,122,484; 6,125,178; 6,128,376; 6,130,937; 6,134,530; 6,137,862; 6,137,870; 6,144,737; 6,148,065; 6,151,387; 6,154,528; 6,154,535; 6,157,711; 6,170,011; 6,173,052; 6,178,240; 6,185,283; 6,192,121; 6,192,413; 6,201,950; 6,205,207; 6,208,970; 6,212,178; 6,226,287; 6,226,360; 6,229,888; 6,230,197; 6,243,684; RE35758; RE36416; RE37001; each of which is expressly incorporated herein by reference.

SUMMARY AND OBJECTS OF THE INVENTION

The summary description of the invention herein provides disclosure of a number of embodiments of the invention. Language describing one embodiment or set of embodiments is not intended to, and does not, limit or constrain the scope of other embodiments of the invention.

The present invention provides a system and method for intelligent communication routing within a low-level communication server system. Therefore, it allows replacement or supplementation of telephone numbers, IP addresses, e-mail addresses and the like, to identify targets accessible by the system with high-level definitions, which are contextually interpreted at the time of communications routing, to appropriately direct the communication. Therefore, the target of a communication is defined by an algorithm, rather than a predetermined address or simple rule, and the algorithm evaluated in real time for resolution of the target, to deliver the communication or establish a real or virtual channel.

Alternately, the intelligence of the server may be used to implement telephony or computer-telephony integration features, other than destination or target.

Therefore, according to the present invention, communications are, or may be, routed or other telecommunications features implemented, inferentially or intelligently, at a relatively low level within the communications management architecture. For example, in a call center, the software system which handles virtual or real circuit switching and management resolves the destination using an algorithm or the like, rather than an unambiguous target.

An embodiment according to the present invention, the control over switching in a circuit switch is partitioned together with intelligent functions.

Intelligent functions include, for example, but are not limited to, optimizations, artificial neural network implementation, probabilistic and stochastic process calculations, fuzzy logic, Bayesian logic and hierarchical Markov models (HMMs), or the like.

A particularly preferred embodiment provides a skill-based call automatic call director for routing an incoming call in a call center to an appropriate or optimal agent. While skill-based routing technologies are known in the art, the intelligence for routing the call is separate from the voice routing call management system. Thus, the prior art provides a separate and distinct process, and generally a separate system or partition of a system, for evaluation of the skill based routing functionality. For example, while the low level voice channel switching is performed in a PBX, the high level policy management is often performed in a separate computer system, linked to the PBX through a packet switched network and/or bus data link.

The present invention, however, integrates evaluation of intelligent aspects of the control algorithm with the communications management. This integration therefore allows communications to be established based on an inferential description of a target, rather than a concrete description, and allows a plurality of considerations to be applied, rather than a single unambiguous decision rule.

An aspect of the present invention therefore proposes an architectural change in the computer telephony integrated (CTI) systems, wherein the CTI host takes on greater responsibilities, for example intelligent tasks, than in known systems. In this case, the host is, for example, a PC server having a main processor, for example one or more Intel Pentium 4 Xeon or AMD Athlon MP processors, and one or more voice channel processors, such as Dialogic D/320-PCI or D/160SC/LS, or PrimeNet MM PCI, or the like. In this type of system, the voice channel processor handles connections and switching, but does not implement control. The control information is provided by the main processor over, for example, a PCI bus, although some or all control information may also be relayed over a mezzanine bus. Because the actual voice channel processing is offloaded from the main processor, real time response with respect to voice information is not required. Therefore, the main processor may operate and be controlled by a standard operating system, in contrast to a real time operating system. While the control processor does operate under certain latency constraints, these are quite long as compared to the response latency required of the voice channel processors. This, in turn, allows the main processor(s) to undertake a plurality of tasks which are not deterministic, that is, the time required to complete processing of a task is unknown and is not necessarily completed within a time window. However, by using state of the art processors, such as a 3.06 GHz Pentium processor, the amount of processing which may be undertaken, meeting a reasonable expectation of processing latency, is substantial. Thus, operating under the same instance of the operating system, for example sharing the same message queue, as the interface between the main processor and the voice channel processor(s), the system according to the present invention may process advanced and complex algorithms for implementing intelligent control. This architecture reduces the required bandwidth for communications with an external high level management system, as well as the processing load thereon. Likewise, since significant decisions and resource allocations are made within the switching system, the need for high quality of service communications channels between the switching system and management system is also reduced.

Preferably, the intelligent algorithm for controlling the voice channels requires minimal access to a disk or mass-storage based database. That is, for any transaction to be processed, preferably either all information is available to the main processor at the commencement of the process, or an initial request is made at commencement of the process, with no additional requests necessary to complete the process, although a stored database may be updated at the conclusion of the process. For example, as a call is received, sufficient information is gathered to define the caller, either by identity or characteristics. This definition may then trigger an initial database lookup, for example to recall a user transaction file or a user profile. Preferably, therefore, a table or other data structure is stored in low-latency memory, for example, double data rate dynamic random access memory (DDR-RAM), which holds the principal parameters and information necessary for execution of the algorithm. Therefore, preferably agent and system status information is present and maintained locally, and need not be recalled for each transaction.

According to a preferred embodiment of the invention, a process is provided for optimizing the selection of an agent within the voice channel switching system. This process is a multi-step process. Only the later part of the process generally need be completed in a time-critical fashion, e.g., as a foreground task. The initial part(s) of the process may be implemented over an extended period of time, so long as the data available for transactions is sufficient current to avoid significant errors.

First, a set of skills are defined, which are generally independent skills, although high cross correlations between skills would not defeat the utility thereof. The skill definitions may be quite persistent, for example over a particular campaign, call center, or even multiple call centers and multiple campaigns. The skills generally are not subject to change after being defined, although through advanced processing or reprocessing of data, clusters in multidimensional space may be defined or revised, representing "skills". Likewise, a manual process may be employed to define the skill set.

Next, for any given task, the skills are weighted. That is, the importance of any skill with respect to the task is defined or predicted. This may also be a manual or automated process. In the case of an automated process for weighting the skills, past tasks similar in nature are analyzed to determine which skills were involved, and to what extent. Typically, since the skill set definitions are normative, the task-skill relationships are derived from data for various or all agents, and need not be limited to the data pertaining to a single or respective agent. The weighting may be adaptive, that is, the weighting need not be invariant, and may change over time based on a number of factors. The weightings may also be time dependent, for example following a diurnal variation.

Each agent is assigned a metric with respect to each skill. This process may be manual or automated, however, a number of advantages accrue from an automated analysis of agent skill level. Typically, an initial skill level will be assigned manually or as a result of an off-line assessment. As the agent is presented with tasks, the proficiency of the agent is analyzed, and the results used to define skill-specific metrics. As stated above, since the skill definitions are normative, the skills of one agent are compared or comparable to skills of others. For example, the skill sets are assigned using a multivariate analysis technique, based on analysis of a plurality of transactions, predicting the best set of skills consistent with the results achieved. In this analysis, each skill metric may be associated with reliability indicia; that is, in some instances, where the outcome of clearly determinable, and a skill as defined is highly correlated with the outcome, the reliability of the determined skill value for a statistically significant sample size is high. On the other hand, where a particular skill is relatively unrelated to the tasks included within the data analysis set, that is, the outcome factor is relatively uncorrelated with the value of the skill, the reliability of a determination of an agent skill will be low.

A related issue relates to inferring an agent skill level for a skill parameter where little or no data is available. For this task, collaborative filtering may be appropriate. A collaborative filter seeks to infer characteristics of a person based on the characteristics of others having similar associated parameters for other factors. See references cited and incorporated by reference above. In this case, there is only a small analytic difference between a parameter for which data is available from a respective agent, but yields an unreliable measurement, and a parameter for which data is unavailable, but can be inferred with some reliability. Therefore, the skill determining process may employ both techniques in a composite; as more data becomes available relating to an actual skill level of an agent with respect to a skill parameter, reliance on inferred skill levels is reduced. It is therefore an aspect of one embodiment of the invention that a collaborative filter is used to infer agent skill levels where specific data is unavailable. It is also an aspect of an embodiment of the invention that in addition to a skill level metric, a reliability estimate for the measurement of the skill level metric is also made available.

It is noted that in defining a desired agent profile for a task, the skill metrics themselves are subject to unreliability. That is, the target skill levels themselves are but an estimate or prediction of the actual skills required. Therefore, it is also possible to estimate the reliability of the target skill level deemed desired. Where the target skill level is low or its estimate unreliable, two separate and distinct parameters, the selected agent may also have a low or unreliably determined skill level for that attribute. On the other hand, where a skill is reliably determined to be high, the agent skill profile should also be high and reliably determined.

In other instances, the metric of skill does not represent a quantitative metric, but rather a qualitative continuum. For example, the optimal speech cadence for each customer may differ. The metric, in this case, represents a speech cadence parameter for an agent. The idea is not to maximize the parameter, but rather to optimize it. Therefore, reliability in this instance does not equate to a reduction in estimated magnitude. It is also noted that a further ancillary parameter may be applied for each skill, that is, tolerance to mismatch. For example, while call received by a call center, for technical support, may seek an agent who is more knowledgeable than the caller is with respect to the problem, but not one who is so far advanced that a communication gap would be apparent. Thus, an optimum skill parameter as well as a range is defined. In like manner, other descriptors of a statistical function or distribution may be employed, for example, kurtosis and skew.

It is noted that there are a number of ways of scoring outcome of a call, and indeed, a number of parallel scoring systems may be employed, although they should be consistently applied; that is, if an agent is selected for handling a call based on one paradigm, care should be employed in scoring the agent or the call outcome using a different paradigm. Such cross analyses, however, may be useful in determining an optimum outcome analysis technique.

When a new matter is to be assigned to an agent, the pool of agents are analyzed to determine, based on the predefined skills, which is the best agent. Selecting the best agent for a task is dependent on a method of scoring outcome, as discussed above. In some instances, there is a relatively simple process. For example, agents entrusted to sell a single product can be scored based on number of units sold per unit time, or the time it takes to close a sale. However, where different products are for sale, optimization may look at different parameters, such as call duration, revenues per call or unit time, profit per call or unit time, or the like. As the variety of options for a user grows, so does the theoretical issues involved in scoring an agent.

It is also possible for agents to engage in an auction; that is, agents bid for a caller. In this case, an agent must be sufficiently competent to handle the call based on the information available, and agents with skills far in excess of those required may be excluded from the bidder pool. For example, agents may be compensated on a commission basis. The bidding may involve an agent bidding a commission rate (up to the maximum allowed). In this way, the employer gets the benefit of competition between agents. The bid, in this instance, may be a manual process entered into by the agent as a prior call is being concluded.

The bid may also be automatically generated at an agent station, based on both objective and subjective factors. See, U.S. Pat. No. 9,818,136, (Hoffberg), expressly incorporated herein by reference, and Steven M. Hoffberg, "Game Theory in the Control of Ad Hoc Networks", Wireless Systems Design 2004 (San Diego, March 8). That is, a bid may be automatically defined and submitted on behalf of an agent. The bid may be defined based on an economic or other criteria.

The optimization of agent selection may also be influenced by other factors, such as training opportunities. Therefore, in determining a cost benefit of selection of a particular agent, a training cost/benefit may also be included.

Thus, according to a simplistic analysis, the agent with the highest score is selected. This is, indeed an "optimum" condition, assuming that there is uniform incremental cost in selecting each agent, and that the system remains static as a result of the selection. On the other hand, if agent costs differ, or the system status is materially altered on the basis of the selection, or there are extrinsic factors, such as training, then the optimum may also differ.

A number of factors may also influence optimality of selection. While most are merely business-based considerations, some may be politically incorrect (bad public policy), or even illegal. For example, an optimization may take into account discrimination on an illegal basis, resulting in harm to either callers or agents within a protected class. That is, a traditionally discriminated-against minority may be subjected to automated and institutionalized discrimination as a result of an algorithm which favors a discriminatory outcome. In fact, the discriminatory outcome may be both efficient and optimal, under an economic or game theory analysis. However, this may be undesired. One way to counteract this is to estimate the discriminatory impact of the algorithm as a whole and apply a global antidiscriminatory factor. While this has the effect of correcting the situation on an overall level, it results in significant inefficiencies, and may result in a redistribution in an "unfair" manner. Further, the antidiscriminatory factor is itself a form of discrimination.

Another method for approaching this problem is to analyze the profile or skill vectors a the presumably discriminated-against agent or customer classes, and compare this to the corresponding vectors of non-discriminated-against class of agents or customers. Assuming that discrimination occurs on a class basis, then, a corrective factor may be used to normalize components of the vector to eliminate the discriminatory effect.

A further method of remediating the perceived discrimination is through training. In this case, the presumably objective outcome determinations are not adjusted, nor is the "economic" model for optimal agent selection disturbed. Instead, a mismatch of the skill profile of an agent with the caller is used as an opportunity to modify behavior (presumably of the agent), such that the deficiency is corrected.

For example, a call center agent may have a characteristically ethnic accent. In one case, the agent accent may be matched with a corresponding caller accent, assuming that data shows this to be optimum. However, assuming that vocal ethnicity relates to socioeconomic status, the result may be that the value of the transaction (or other score value) is associated with this status. The goal would therefore be for the agent to retrain his or her accent, and indeed use a different accent based on an inferred optimal for the caller, or to overcome this impediment by scoring well in transactions involving those other than a "corresponding" accent. Each of these is subject to modification through agent training.

Therefore, it is apparent that the optimization may be influenced by economic and non-economic factors, and the optimization may include objective and subjective factors.

The system may also intelligently analyze and control other aspects of telecommunications besides call routing.

For example, it is particularly advantageous to characterize the caller, especially while the call is in the queue. However, increasing the amount of information which must be communicated between the switch control and a high-level system is undesirable, thus limiting the ability to extract low-level information from the caller. Such information may include preferred language, a voice stress analysis, word cadence, accent, sex, the nature of the call (IVR and/or speech recognition), personality type, etc. In fact, much of this information may be obtained through interaction and/or analysis of the caller during the queue period. Further, in some instances, it may be possible to resolve the callers issues without ever connecting to an agent, or at least to determine whether a personal or automated resolution is preferred. According to an aspect of the invention, the switch itself may control and analyze the interaction with the caller. Advantageously, the switch may further perform a sensitivity analysis to determine which factors relating to the call are most useful with respect to selecting an appropriate agent, and more particularly by limiting this analysis to the agents within the pool which are likely to be available. Further information characterizing the user may also be gathered to construct a more detailed user profile.

It is noted that, in some cases, a caller prefers to remain passive in the queue, while in other instances, the caller would prefer to actively assist in optimizing the experience. This does not necessarily correlate with a universal caller profile, nor the optimal selection of agent. This can be quickly ascertained, for example through IVR.

It is noted that an efficient analysis performed by the switch may differ from an efficient analysis performed or controlled by a high level system. For example, a high level system may employ speech recognition technology for each caller in a queue. The switch, on the other hand, would likely not be able to implement speech recognition for each caller in a large queue internally. Further, since the profile of the caller and the correspondence thereof to the agent skill profile, as well as the correlation to the outcome, is dependent on the selection of characteristics for analysis and outcome metric, the parameters of each, according to the present invention, will also likely differ.

Returning now to the problem of routing a call using an intelligent switch, the condition of optimality in the case of equal incremental cost, a stationary system condition as a result of the selection, and scalar skill parameters having a magnitude correlated to value, is denoted by the formula:

$$A_n = \text{Max } \Sigma(rs_i a_n s_i)$$

Which denotes that Agent "n" is selected by maximizing the sum, for each of the required skills $s_i$, of the product of weighting for that skill $rs_i$, and the score for agent n $a_n s_i$.

As stated above, this optimization makes two very important, and not always applicable assumptions. First, more highly skilled agents often earn higher salaries. While, once scheduled, presumably the direct cost is fixed, over the long term, the pool of agents must be adjusted to the requirements, and therefore the selection of an "expensive" agent leads to increased costs. On the other hand, by preferentially selecting the skilled agent over the unskilled agent, the job experience for the skilled agent may be diminished, leading to agent retention problems. Likewise, the unskilled agent is not necessarily presented with opportunities for live training. Thus, it is seen that the agent cost may therefore be a significant variable.

The formula is therefore modified with a cost function as follows:

$$A_n = \text{Max } [Ac_{n1} \Sigma(rs_i a_n s_i) + AC_{n2}]$$

Wherein $AC_{n1}$ and $Ac_{n2}$ are agent cost factors for agent n. To determine the anticipated cost, one might, for example, divide the daily salary by the average number of calls per day handled by the agent. This, however, fails to account for the fact that the average length of a call may vary based on the type of call, which is information presumed available, since the skill set requirements are also based on a classification of the type of call. Further, an agent highly skilled in some areas may be relatively unskilled in others, making an average call duration or average productivity quite misleading. Another cost to be considered is training cost. Since this is generally considered desirable, the actual value may be negative, i.e., an unskilled trainee may be selected over a highly skilled agent, for a given call, even though the simple incremental agent costs might tend toward a different result. Likewise, selection of an agent for a certain call may be considered a reward or a punishment for good or bad performance, and this may also be allocated a cost function. The key here is that all of these disparate factors are normalized into a common metric, "cost", which is then subject to numeric analysis. Finally, the optimization may itself evolve the skill sets and cost function, for example through training and reward/punishment.

The cost of the "connection" between a caller and an agent may also be considered, for example in a multi-location call center, or where agents are compensated on a per-call basis.

Another factor to be considered in many cases is anticipated outcome. In some instances, the outcome is irrelevant, and therefore productivity alone is the criterion. On the other hand, in many cases, the agents serve a business purpose, and call outcomes may be graded in terms of achieving business goals. In many instances, the business goal is simple an economic parameter, such as sales volume, profit, or the like, and may be directly computed within a cost function normalized in economic units. On the other hand, some business goals, such as customer satisfaction, must be converted and normalized into economic terms prior to use in an optimization. In any case, the expected outcome resulting from a particular agent may be added as a factor in the cost function.

Another factor to consider in making a selection of an agent in a multi-skill call center is the availability of agents for other calls, predicted or actual. Thus, while a selection of an agent for one matter may be optimal in a narrow context, the selected agent might be more valuable for another matter. Even if the other matter is predicted or statistical, in some instances it is preferred to assign more specialized agents to matters that they can handle, rather than assigning multitalented agents.

This is represented as follows:

$$A_n = \text{Max} < (\{[Ac_{n1}\Sigma(rs_i a_n s_i) + Ac_{n2}] + Bc_n\} + Cc_n) + Dc_n >$$

Wherein $B_c$ represents a term for the anticipated change in value of agent n as a result of the selection, $C_c$ represents a term which indicates the anticipated value of the transaction resulting from the selection of agent n, and $D_c$ represents the opportunity cost for allocating agent n to the particular call.

In the case of competing requests for allocation, a slightly different formulation of the problem may be stated. In that case, one might compare all of the cost functions for the matters in the queue with respect to each permissible pairing of agent and matter. Instead of selecting an optimal agent for a given matter, the system selects an optimal pairing of respective multiple agents with multiple matters. In the case of a call center, often the caller hold time is considered a basic criterion for selection. In order to weight this factor, for example, the cost function includes an allocation for caller hold time, and possibly a non-linear function is applied. Thus, a caller may be taken out of order for paring with an optimal agent.

In some cases, the variance of a parameter is also considered, in addition to its mean value. More generally, each parameter may itself be a vector, representing different aspects.

It is noted that the various factors used in the system may be adaptive, that is, the predicted values and actual values are compared, and the formula or variables adjusted in a manner which is expected to improve the accuracy of the prediction. Since outcome is generally measured in the same metric as the cost function, the actual cost is stored along with the conditions of the predictive algorithm, and the parameters updated according to a particular paradigm, for example an artificial neural network or the like. Typically, there will be insufficient data points with respect to a system considered static to perform an algebraic optimization.

The present invention provides cost function optimization capabilities at a relatively low level within the call routing system. Thus, for example, prior systems provide relatively high level software, operating on massive customer relations management (CRM) database systems, to seek optimization.

On the other hand, according to the present invention, the parameters are supplied in advance, generally in a batch format, to the low level routing and computer integrated telephony (CTI) software, which computes the cost functions. Call outcome data is generally available during and after a call to the high level software, which can then set or adjust values as necessary for the future.

It is noted that, generally, the architecture according to the present invention would not generally provide agent scheduling information, since this represents a task separate from the call routing functions. Therefore, known systems which integrate both tasks are typically distinguished from the present invention. However, it would be possible as a separate process for this to be performed on the telephony server according to the present invention. More generally, the updating of agent skill tables or a database, and agent scheduling and call center management, are performed on high level systems which are discrete from the telephony server. These systems typically access large databases, generate reports, and integrate many different functions independent of the communications functions.

The advantage of a preferred architecture according to the present invention is that when a call is received, it can be routed in real time, rather than after a possibly significant delay. Further, this data processing partition reduces data communications bandwidth requirements and reduces transactional load on the CRM system. In addition, this architectural partition reduces the need for the CRM system to be involved in low level call management, and reduces the need for the CTI software to continually interact with the high level CRM software. This, in turn, potentially allows use of simple architecture CTI platforms using standard operating systems.

According to a preferred embodiment, the matter skill requirements, agent skill data, and other parameters, are provided to the CTI software, for example as an ASCII table. The CTI software may, for example, invoke a subprocess for each call received or in the queue, to determine the then-optimum agent selection, for a local optimization, i.e., a selection of the optimal agent without regard for the effect of this selection on other concurrent optimizations. In order to globally optimize, the processing is preferably unitary. As conditions change, for example, further calls are added to the queue, or calls are completed, the optimizations may be recomputed.

For example, in a call center with 500 agents, each classified with respect to 32 skills, with an average of 2000 calls in the queue, with about 50 agents available or anticipated to be available at any given time, the computational complexity for each optimization is on the order of $160 \times 10^6$ ($2000 \times 50 \times 50 \times 32$) multiplies, generally of 8-bit length. A 2 GHz Pentium 4 processor, for example, is capable of theoretical performance of about 2400 MFLOPS. Using a simplified calculation, this means that less than about 10% of the raw capacity of this processor would be required, and more powerful processors are being introduced regularly. For example, a 3.06 GHz Pentium 4 processor with "hyper-threading" has recently been introduced. In fact, in real-world situations, the processor would likely not be able to achieve its benchmark performance, but it is seen that a single modern processor can handle, in near real time, the required processing. Coprocessing systems are available which increased the processing capability, especially with respect to independent tasks, while allowing all processes to be coordinated under a single operating system. For example, Microsoft Windows and Linux both support multiprocessing environments, in case increased processing capacity is required.

On the other hand, if a high level CRM system is interrupted to process each call event to globally reoptimize agent selection, and communicate this with the CTI software, a significant communication and transaction burden would be encountered.

Thus, the present invention proposes that the skill-based call routing algorithm be executed in conjunction with the low level CTI process, as an integral part of the call routing function. Likewise, other call-process related algorithms may be implemented, in addition to or instead of a call routing calculation.

Advantageously, for example in many non-adaptive systems, no high level CRM system is required, and the entire skill-based routing functionality may be implemented in the CTI system, saving significant hardware expense and software complexity. Thus, where the cost function is relatively simple to calculate, the skills required for the call and the skills of each respective agent well known and relatively constant, a simple database may be provided for the CTI platform to route calls intelligently.

Another aspect of the invention provides optimization of communications management based on adaptive parameters, e.g., not only on the existing skills of the respective agents, but rather also based on an anticipated or predicted change in the agent's skills as a result of handling the call. Likewise, when considering an overall cost function for optimizing call directing, any variety of factors may be considered within its context. Therefore, it an another object to provide a consolidated cost function for communications management, wherein pertinent factors or parameters are or may be expressed in common terms, allowing unified consideration. According to a preferred embodiment of the invention, this is handled at a low level within the communications management system, although various aspects may be handled in real time or otherwise at various levels of the communications management system.

In the case of real time communications, such as traditional voice telephony, the switching must by definition occur in real time, so must the resolution of the parties to the communication. Therefore, another aspect of the invention involves communications and coordination in real time of the various system components, including the low level system. Preferably, the data upon which an optimization is based is available locally to the low level system before a real time communication is received, so that external communications to resolve the target are minimized. In some cases, communications with other system components will still be required, but preferably these do not require essentially non-deterministic systems to respond prior to resolution.

Another aspect of the invention seeks to optimize long term call center operations, rather than immediate efficiency per se. Thus, at various times, the system performs functions which are different or even opposite the result expected to achieve highest short term efficiency. Preferably, however, during peak demand periods, the system assures high short term efficiency by switching or adapting mode of operation.

Therefore, according to the present invention, a number of additional factors are applicable, or the same factors analyzed in different ways, beyond those employed in existing optimizations. Since most call centers are operational for extended periods of time, by analyzing and optimizing significant cost factors beyond those contemplated by the prior art, a more global optimization may be achieved.

In a service environment, the goal is typically to satisfy the customer at lowest cost to the company. Often, this comes through making a reasonable offer of compromise quickly, which requires understanding the issues raised by the customer. Delay leads to three costs: the direct and indirect operations cost; the possibility of increased demands by the customer (e.g., impaired business marginal utility of the communication); and the customer satisfaction cost.

In technical support operations, the agent must understand the technical issues of the product or service. The agent must also understand the psychology of the user, who may be frustrated, angry, apologetic, or even lonely. The agent must often remotely diagnose the problem, or understand the information provided by the caller, and communicate a solution or resolution.

In some instances, these seemingly abstract concepts are represented in relatively basic terms at the communications server level. For example, the cadence of a speaker may be available by a simple analysis of a voice channel for silence and word rate. Stress may also represented in a spectral analysis of voice or in other known manner. Alcoholism or other impairment may be detected by word slurring, which may also be detected by certain signature patterns in the voice pattern.

It is noted that, in some instances, the skill related parameters are not independent. That is, there is a high cross correlation or other relationship between the parameters. In other instances, there are non-linearities in the process. A simple summing of magnitude times weight for these parameters may introduce errors. Therefore, a more complex algorithm may be employed, without departing from the spirit or scope of the present invention.

Likewise, for each caller profile class, a different optimization may be employed. There are some traits, such as alcoholism, which may alter the optimal selection of agent, all other thing being equal.

Therefore, communications routing on seemingly sophisticated or abstract concepts may be efficiently handled at a low level without interrupting the basic call processing functions or requiring non-standard hardware. In this sense, "non-standard" refers to a general purpose type computing platform performing the communications routing functions. In fact, efficiency is generally enhanced according to the present invention by avoiding the need for remote communications of the call parameters and the resulting communications and processing latencies. Of course, in certain tightly coupled environments, the target resolution may be performed on a physically separate processor or system from the low level call processing, without deviating from the essential aspects of embodiments of the invention.

In many cases, the caller characteristics and issues will often have a significant effect on the duration of the call. While, in general, more skilled agents will have a higher productivity, in some cases, the caller restricts throughput. Therefore, even though the agent is capable of completing the call quickly, the caller may cause inordinate delays. According to the present invention, through a number of methods, the caller characteristics are determined or predicted, and an appropriate agent selected based on the anticipated dynamic of the call. Thus, for example, if the anticipated call duration for a successful outcome, based on the caller characteristics is a minimum of 5 minutes (depending on the agent), then an agent who is likely to complete the call in about 5 minutes may be selected as the optimum; agents who would be able to complete the call within 4 minutes, while technically more productive, may have little impact on the actual call duration, and thus would be inefficiently employed. Likewise, an agent anticipated to complete the call in 6 minutes might be deemed inefficient, depending on the availability of other agents and additional criteria. The call may be selected as a training exercise. In this case, an agent is selected for training whom would be expected to operate with a certain degree of inefficiency to complete the call. In some cases, unsupervised training is instituted. In other cases, a training agent (or automated system) is allowed to shadow the call, providing assistance, instruction and/or monitoring of the trainee agent during the call. In this case, it would be anticipated that the call duration would be greater than 5 minutes, due to the training nature of the call. Further, the required trainer assistance further reduces immediate efficiency. However, as the agents in the pool become more skilled, long term efficiency increases.

Preferably, these characteristics are extracted through an analysis, by the communications control system, of the available data, although where appropriate, reference to higher level systems may be performed. Thus, in an interactive voice (or key) response system, there may be sufficient time and resources available to query a high level system for data or request analysis relating to a call. However, in many instances, significant analysis may be performed using the computing resources and information available to the low level communication processing system. Even where the information is not available, a DNIS or other type of lookup may provide this information based on a relatively simple query.

More highly skilled agents are both worth more and generally command higher compensation. A program which trains agents internally is either required, due to lack of specific external training programs, or is cost effective, since new hires can be compensated at a lower rate than trained and experienced hires. Thus, for long-term operations, there is an incentive to train agents internally, rather than seeking to hire trained agents. Therefore, according to another aspect of the invention, such training, past present and/or future, is monetized and employed in optimization of a cost function.

Agents may receive additional compensation for training activities, either for their training activities, performance based compensation based on the improvement of their trainees, or both. Thus, there is an incentive for agents to become skilled and to assist in the training. As a result, the average skill level and uniformity in a call center will increase. However, since the optimal skill palette within a call center typically is a moving target, the training process will never cease.

Often, live interaction is an important component of training. Therefore, a significant component of the training encompasses interaction with callers in real-world situations. Training often involves presenting agents with new challenges and experiences in order to assure breadth of exposure.

According to prior skill-based routing schemes, an agent skill level is considered a static upper limit on capabilities, and the ACD avoids distributing calls to agents below a threshold. Agents may be called upon to serve requests within their acknowledged skill set. Likewise, this allows a simple and discrete boundary condition to be respected in the optimization according to the present invention.

On the other hand, according to some embodiments of the present invention, each call is considered a potential training exercise, in order to expand the capabilities of the agent, and therefore the boundary is not concretely applied. Therefore, to the extent that the nature of the call can be determined in advance, the incentive according to this scheme is to route the call to an agent who is barely capable of handling the call, and to avoid routing only to the best available agents. This strategy has other implications. Because agents are challenged continually, there is reduced incentive for an agent to limit his skills to avoid the "tougher" assignments. Further, a self-monitoring scheme may be implemented to determine the status of an agent's skill with each call. For example, agent performance is typically determined on a call-throughput basis, since call centers are managed on a man-hour requirement basis and agents compensated on a per-hour basis. Therefore, based on a presumed agent skill set and an estimation of the skills required for a given call, a call duration may be predicted. The actual duration is then compared with the predicted duration, providing a performance metric for the agent.

This scheme also allows determination of the pertinent factors for call duration, both based on the information about the call or caller and the skill set of the agent. Thus, a variety of low-level data may be collected about a volume of calls, which may be statistically or otherwise analyzed to determine significant relations. For example, an artificial neural network or fuzzy-neural network may be implemented based on the data, which may then be automatically analyzed based on the independent criteria, e.g., call duration, cost function, or the like.

It is noted that, during peak demand periods, reduced productivity due to training exercises is preferably minimized. Thus, as demand increases, high skill set agents are preferably reassigned from training to most-efficient operational status, while lower skill set agents are assigned to calls well within their capabilities. Thus, during such peak demand periods, the staffing requirement will generally be no worse than traditional call centers. On the other hand, since training is integrated with operations, over a period of time, the average skill of all agents will increase. Thus, more skilled agents will be available at peak periods, reducing overall staffing requirements over a long term due to an expected decrease in average call duration and increase in agent productivity.

According to this embodiment of the invention, it is less critical to perform the call routing resolution in the low level system, since the real time criteria is not particularly limited by processing and communication latencies. On the other hand, corresponding skill routing functions may be performed by the communications processing system for both outbound and inbound communications, thus permitting a simplification of the external supporting systems.

An embodiment of the present invention provides an Internet Protocol based communications architecture, permitting geographically dispersed physical communications locations to act as a single coordinated entity. In order to centrally manage a queue, the various pieces of information must be available for processing. As noted above, an interactive optimization may require a real time comparison of all available agents. In this architecture, in cases of an ad hoc organization or peak demand periods, freelance agents may be called upon dynamically as required. Thus, if a peak demand period is much shorter than an agent shift, off-site freelance agents may be dynamically called upon, for example through the Internet, ISDN, POTS, DSL, Cable modem, or a VPN, to handle calls. In this case, the optimal training of such off-site or freelance agents will generally differ from those who are in-house agents. For example, if freelance agents are called upon only during peak demand periods, these agents will be trained specifically for the skills in short supply during such periods, or for generic skills which are commonly required.

In order to gage the skill set required of an agent for a call, a number of methods may be employed. Using a menu or hierarchical menu, a series of questions may be asked of callers in the queue to determine the identity of the caller and the nature of the call. Likewise, ANI/DNIS information, IP address or the like, or other communications channel identifier may be employed to identify the calling telephone communications channel. This information may directly indicate the characteristics or desired characteristics of the communication, or be used to call an external database record associated with the identity of the caller or communications channel. While it is possible to associate such a database closely with the low level communications processing system, this is not generally done, since it may impair the deterministic characteristics of the communications processing system. Rather, if such information is required by the low level communications system for resolution, and cannot be stored locally in a data table, it is preferred that it be available through a closely coupled, but independent system. As discussed above, it is preferred that a call entering the queue require no more than a single database query and receipt of response prior to action, although other non-time critical access may occur both before and after action. The prior art, on the other hand, generally provides such information through independent and generally high level systems. High level systems are generally characterized by general purpose interfaces, broad range of functionality, and often a communications protocol having a rich and complex grammar. On the other hand, tightly coupled systems can often forgo extensibility and interoperability in favor of efficiency.

In many instances, call centers are implemented to provide support for computer systems. It is known to provide a message automatically generated by a computer to identify and report the status of the computer at a given time, and possibly the nature of a computer problem. One aspect of the present invention allows this message to be associated with a direct semantic communication session with the user, for example to predefine the nature of the call and possibly the skill set required to address the issues presented. Thus, for example, a caller may be prompted to specify information of particular relevance in the routing process, while not being prompted for information irrelevant to the selection. For example, if only one agent is available, the entire prompting process may be bypassed. If two agents are available, their profiles may be analyzed, and only the most critical distinctions probed. This entire process may be handled in the low level communications processing system, without substantial loss of efficiency or throughput in that system, and with substantial gains in overall architectural efficiency.

Often, a highly skilled agent will serve as mentor for the trainee, and "shadow" the call. Thus, the routing of a call may depend on availability of both trainee and skilled instructor. This dual-availability checking and pairing may be performed in the low level system.

Another aspect of call center efficiency impacted by this scheme is agent motivation. Because an agent with lower skill levels will be given assignments considered challenging, while more skilled agents given training assignments which may be considered desirable, there is an incentive for agents to progress, and likewise no incentive to avoid progressing. Thus, an agent will have no incentive to intentionally or subliminally perform poorly to avoid future difficult skill-based assignments. These factors may be accommodated in a cost function calculation, for example with an update of the agent vector after each call based on call characteristic vector, call outcome and duration, chronological parameters, and the like.

In operation, the system works as follows. Prior to call setup, the nature of the call is predicted or its requirements estimated, as well as the prospective issues to be encountered. This may be performed in standard manner, for example in an inbound call based on the number dialed, based on the ANI/DNIS of the caller (with possible database past history lookup), selections made through automated menus, voice messages, or other triage techniques. In the case of outbound calls, a database of past history, demographic information (both particular to the callee and for the region of the call), and nature of the call may all be used to determine the projected agent skill set required for the call. Alternately, only parameters available locally to the communications control system are employed, which, for example, may exclude a past history database lookup. Collaborative filtering may be used to assist in inferring a profile of a remote user.

It is noted that, after initial call setup, the actual skill set required may become apparent, and the call may be rerouted to another agent. For example, this may be performed at a high level, thus permitting correction of errors or inappropriate selections made by the low level system.

Once the predicted skill sets are determined, these are then compared against a database of available agents and their respective skill sets. A weighting is applied based on perceived importance of selection criteria, and the requirements correlated with the available agent skill sets.

When the call center is operating below peak capacity, marginally acceptable agents may be selected to receive the call, possibly with a highly acceptable agent available if necessary for transfer or handoff or to monitor the call. When the call center is operating near peak capacity, the agents are assigned to minimize the anticipated man-hour burden (throughput) and/or wait time. Thus, peak throughput operation generally requires that agents operate within their proven skill sets, and that training be minimized.

Each call is associated with a skill expression that identifies the skills that are relevant to efficient handling of the call. As previously noted, the preferred embodiment is one in which more than one relevant skill is identified, so that all of the factors that determine a "best" agent for handling a call can be considered. This is expressed, for example, as a call characteristic vector. The relevant skills required may be determined using different techniques.

The skill expression of a call includes the required skills and skill levels for efficiently handling the call. In one embodiment, the skills may be divided into two categories: mandatory and optional skills. Mandatory skills are those skills that an agent must possess in order to handle the call, even if the call remains in queue for an extended period of time. For example, language proficiency is often a mandatory skill for handling a call. Optional skills are those that are considered in the selection of the appropriate agent, but not critical. In operation, these mandatory skills are expressed as a high relevance rating with respect to a call characteristic having a non-linear (e.g., binary or sigmoid) characteristic. Therefore, in the absence of exceptional circumstances, other factors for qualified agents will determine resolution. Alternately, the mandatory skills may be specified as a pre-filter, with optional skills and cost function expressed through linear-type equations.

It is noted that the peak/non-peak considerations may be applied on a call-by-call basis. Thus, certain callers may be privileged to have a shorter anticipated wait and greater efficiency service than others. Thus, these callers may be treated preferentially, without altering the essential aspects of the invention.

The present invention may also generate a set of reports directed to management of the call center. Typically, the communications server generates a call log, or a statistically processed log, for analysis by a higher level system, and does not generate complete, formatted reports itself. The quality of service reports are generated to indicate the effectiveness of the call-management method and system. An agent summary report is organized according to the activities of particular individuals, i.e. agents. A skill summary report organizes the data by skill expressions, rather than by agents. This report may list the number of calls requiring selected skill expressions and the average time spent on those calls. Other known report types are also possible. An important report type is the improvement in call center efficiency over time, i.e., decreased wait time, increased throughput, increased customer satisfaction, etc. Thus, each agent should demonstrate improved skills over time. Peak throughput should meet or exceed reasonable expectations based on a statically skill-routed call center. Other metrics may also be evaluated. Such reports are typically not generated from low level communications systems, and are considered an inventive feature.

It is therefore an object of the invention to provide a communications control system comprising an input for receiving a call classification vector, a table of agent characteristic vectors, and a processor, for (a) determining, with respect to the received call classification, an optimum agent selection based on at least a correspondence of said call classification vector and said table of agent characteristic vectors, and (b) controlling a call routing of the information representing said received call in dependence thereon. It is a further object of the invention to provide a system wherein the process maintains a table of skill weights with respect to the call classification, and applies said weights to determine an optimum agent selection.

Another object of the invention is to provide a communications control system for handling real time communications, wherein an integral system resolves a communications target based on an optimizing algorithm and establishes a communications channel with the resolved communications target.

A further object of the invention provides a communications method comprising receiving a call, classifying the call to determine characteristics thereof, receiving a table representing characteristics of potential targets, determining an optimum target based on the characteristics of both the call and the potential targets, and routing the received call to the optimum target, the determining step and the routing step being performed by a common platform.

A still further object of the invention provides a communications control software system, comprising a multi-threaded operating system, providing support for applications and for passing messages between concurrently executing applications, a communications control server application executing under said multithreaded operating system, for controlling real time communications, and at least one dynamically linkable application, executing under said multithreaded operating system, communicating with said communications control server application to receive call characteristic data and transmit a resolved communications target.

Another object of the invention provides a method of determining an optimum communications target in real time, comprising receiving a communication having an indeterminate target, selecting an optimum target, and establishing a channel for the communication with the optimum target, wherein said selecting and establishing steps are performed on a consolidated platform.

It is a further object of the invention to provide a communications processing system for directly establishing and controlling communications channels, receiving information regarding characteristics of a preferred target of a communication, comparing the characteristics with a plurality of available targets using an optimizing algorithm, and establishing the communication with the target in dependence thereon.

It is another object of the invention to provide a method of selecting a call handling agent to handle a call, comprising the steps of identifying at least one characteristic of a call to be handled; determining a call center load, and routing the call to an agent in dependence on the characteristic, call center load, and agent characteristics.

A further object of the invention provides a method optimizing an association of a communication with an agent in a communications center, comprising the steps of determining a characteristic of a communication; accessing a skill profile of a set of agents; cost-optimizing the matching of the communication with an agent based on the respective skill profile, and routing the call to a selected agent based on said cost-optimization with a common system with said optimizing.

An object of the invention also includes providing a method for matching a communication with a communication handler, comprising the steps of predicting a set of issues to be handled during the communication; accessing a profile record for each of a plurality of communications handlers; analyzing the profile records with respect to the anticipated issues of the communication to determine a minimal capability; selecting an optimum communication handler; and controlling the communication, all controlled within a common process.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which:

FIG. 5 shows a second block diagram in accordance with the present invention.

DETAILED DESCRIPTION OF THE PREFERRED EMBODIMENTS

The Detailed description of the invention is intended to describe relatively complete embodiments of the invention, through disclosure of details and reference to the drawings. The following detailed description sets forth numerous specific details to provide a thorough understanding of the invention. However, those of ordinary skill in the art will appreciate that the invention may be practiced without these specific details. In other instances, well-known methods, procedures, protocols, components, and circuits have not been completely described in detail so as not to obscure the invention. However, many such elements are described in the cited references which are incorporated herein by reference, or as are known in the art.

For each agent, a profile is created based on manual inputs, such as language proficiency, formal education and training, position, and the like, as well as automatically, based on actual performance metrics and analysis, and used to create a skills inventory table. This process is generally performed in a high level system, such as a customer relations management system or human resources management system. A profile thus represents a synopsis of the skills and characteristics that an agent possesses, although it may not exist in a human readable or human comprehensible form.

Preferably, the profile includes a number of vectors representing different attributes, which are preferably independent, but need not be. The profile relates to both the level of ability, i.e. expertise, in each skill vector, as well as the performance of the agent, which may be a distinct criterion, with respect to that skill. In other words, an agent may be quite knowledgeable with respect to a product line, but nevertheless relatively slow to service callers. The profile, or an adjunct database file, may also include a level of preference that call management has for the agent to handle transactions that require particular skills versus transactions that require other skills, or other extrinsic considerations.

This table or set of tables is communicated to the communications server. Typically, the communications server does not create or modify the agent skills table, with the possible exception of updating parameters based on immediate performance. For example, parameters such as immediate past average call duration, spoken cadence, and other statistical parameters of a call-in-progress or immediately past concluded will be available to the communications server. These parameters, which may vary over the course of a single shift, may be used to adaptively tune the profile of the agent in real time. Typically, however, long term agent performance is managed at higher levels.

Figure 1:
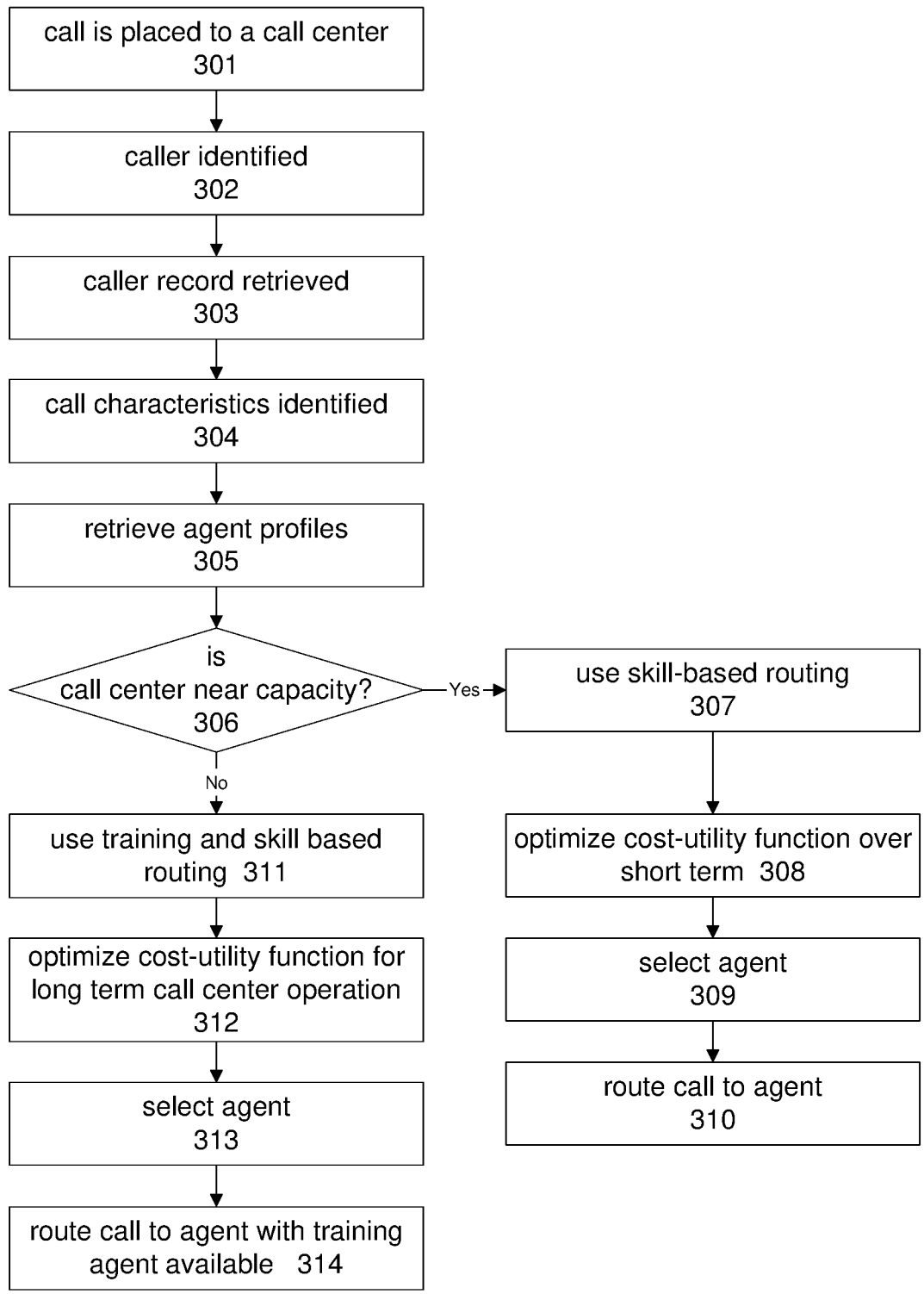
FIG. 1 shows a first flow chart showing a skill routing method according to the present invention.
Figure 2:
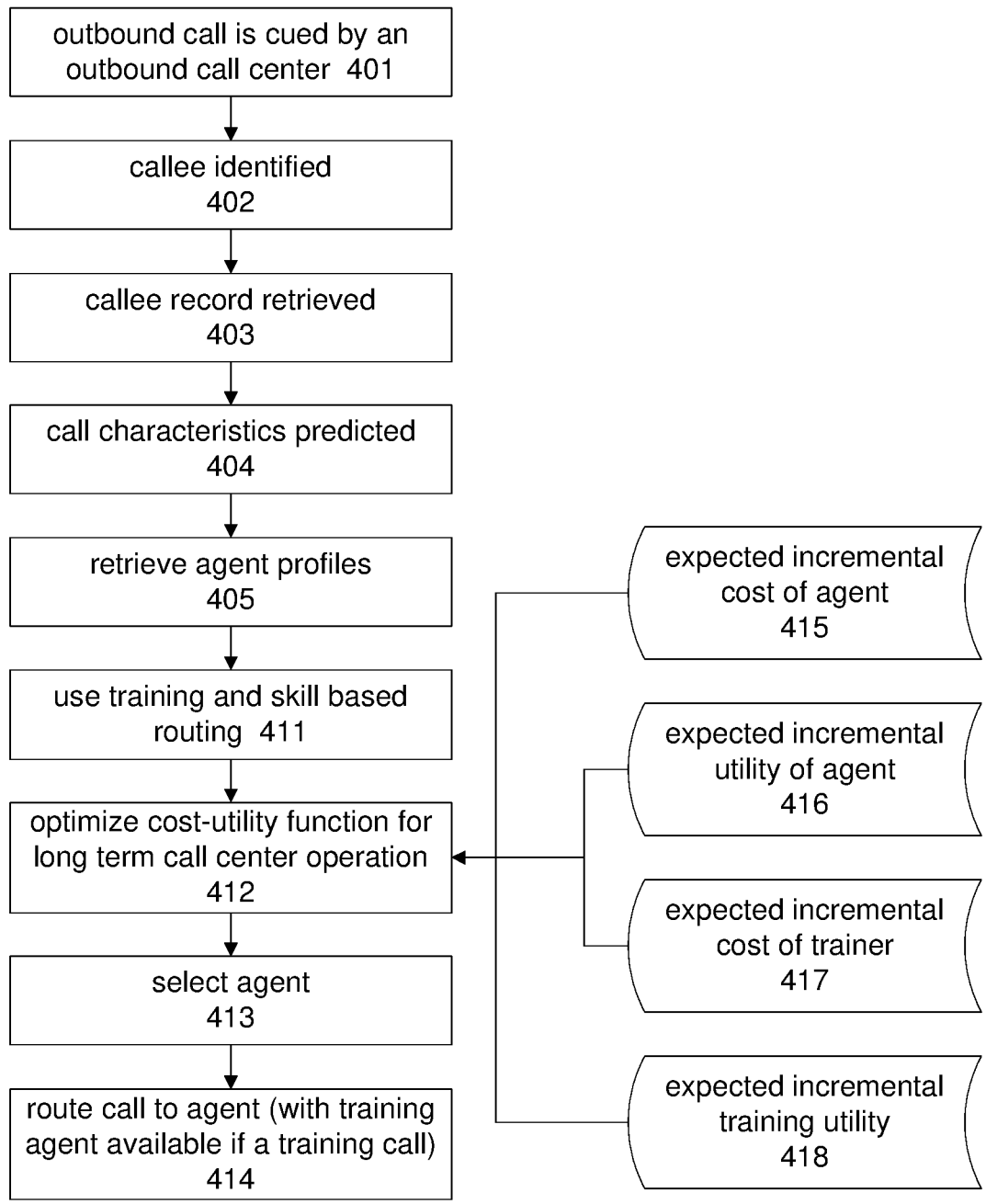
FIG. 2 shows a second flow chart showing a skill routing method according to the present invention.

FIG. 1 shows a flow chart of an incoming call routing algorithm according to a preferred embodiment of the present invention. A call is placed by a caller to a call center 301. The call is directed, through the public switched telephone network, although, calls or communications may also be received through other channels, such as the Internet, private branch exchange, intranet VOIP, etc. The source address of the call, for example the calling telephone number, IP address, or other identifier, is received to identify the caller 302. While the call is in the waiting queue, this identifier is then used to call up an associated database record 303, providing, for example, a prior history of interaction, a user record, or the like. The call waiting queue may be managed directly by the telephony server. In this case, since the caller is waiting, variable latencies due to communications with a separate call management system would generally not interfere with call processing, and therefore may be tolerated. In other instances, an interactive voice response (IVR) system may be employed to gather information from the caller during the wait period.

In some instances, there will be no associated record, or in others, the identification may be ambiguous or incorrect. For example, a call from a PBX wherein an unambiguous caller extension is not provided outside the network, a call from a pay phone, or the like. Therefore, the identity of the caller is then confirmed using voice or promoted DTMF codes, which may include an account number, transaction identifier, or the like, based on the single or ambiguous records.

During the identity confirmation process, the caller is also directed to provide certain details relating to the purpose of the call. For example, the maybe directed to "press one for sales, two for service, three for technical support, four for returns, and five for other". Each selected choice, for example, could include a further menu, or an interactive voice response, or an option to record information.

The call-related information is then coded as a call characteristic vector 304. This call characteristic is either generated within, or transmitted to, the communications server system.

Each agent has a skill profile vector. This vector is developed based on various efficiency or productivity criteria. For example, in a sales position, productivity may be defined as sales volume or gross profits per call or per call minute, customer loyalty of past customers, or other appropriate metrics. In a service call, efficiency may be defined in terms of minutes per call, customer loyalty after the call, customer satisfaction during the call, successful resolution of the problem, or other metrics. These metrics may be absolute values, or normalized for the agent population, or both. The skill profile vector is stored in a table, and the profiles, which may be updated dynamically, of available or soon to be available agents, are accessed from the table (database) 305.

Typically, the table 305 is provided or updated by a high level call center management system to the communications server system as the staffing assignments change, for example once or more per shift. Intra-shift management, such as scheduling breaks, may be performed at a low or high level.

The optimization entails analysis of various information, which may include the caller characteristics, the call incident characterization, availability of agents, the agent profile(s), and/or various routing principles. According to the present invention, the necessary information is made directly available to the communications server, which performs an optimization to determine a "best" target, e.g., agent selection, for the caller.

For example, if peak instantaneous efficiency is desired, for example when the call center is near capacity 306, more advanced optimizations may be bypassed and a traditional skill based call routing algorithm 307 implemented, which optimizes a short term cost-utility function of the call center 308. An agent who can "optimally" handle the call is then selected 309, and the call routed to that agent 310. The global (e.g., call center) factors may be accounted as a separate set of parameters.

Thus, in order to immediately optimize the call routing, the general principle is to route the call such that the sum of the utility functions of the calls be maximized while the cost of handling those calls be minimized. Other types of optimizations may, of course, be applied.

According to one optional aspect of the invention, the various routing principles discussed above explicitly value training as a utility of handling a call 311, and thus a long-term optimization is implemented 312. The utility of caller satisfaction is also weighted, and thus the agent selected is generally minimally capable of handling the call. Thus, while the caller may be somewhat burdened by assignment to a trainee agent, the call center utility is maximized over the long term, and call center agents will generally increase in skill rapidly.

In order for the communications server system to be able to include these advanced factors, they must be expressed in a normalized format, such as a cost factor.

As for the cost side of the optimization, the cost of running a call center generally is dependent on required shift staffing, since other costs are generally constant. Accordingly, a preferred type of training algorithm serves to minimize sub-locally optimal call routing during peak load periods, and thus would be expected to have no worse cost performance than traditional call centers. However, as the call center load is reduced, the call routing algorithm routes calls to trainee agents with respect to the call characteristics. This poses two costs. First, since the trainee is less skilled than a fully trained agent, the utility of the call will be reduced. Second, call center agent training generally requires a trainer be available to monitor and coach the trainee. While the trainer may be an active call center agent, and therefore part of the fixed overhead, there will be a marginal cost since the trainer agent might be assuming other responsibilities instead of training. For example, agents not consumed with inbound call handling may engage in outbound call campaigns.

It is clearly apparent that the communications server system will have direct access to call center load data, both in terms of availability of agents and queue parameters.

Thus, in a training scheme, an optimization is performed, using as at least one factor the value of training an agent with respect to that call 312, and an appropriate trainee agent selected 313.

In order to provide proper training, the trainer and trainee must both be available, and the call routed to both 314. Generally, the trainee has primary responsibility for the call, and the trainer has no direct communication with the caller. Therefore, the trainer may join the call after commencement, or leave before closing. However, routing a call which requires two agents to be simultaneously available poses some difficulties. In general, the trainer is an agent capable of handling the entire call alone, while the trainee may not be. Therefore, the trainer is a more important participant, and the initial principle in routing the training call is to ensure that a trainer is available. The trainer may then await availability of an appropriate trainee, or if none is imminently available, handle the call himself or herself.

On the other hand, where a specific training campaign is in place, and a high utility associated with agent training, then the availability of a specific trainee or class of trainees for a call having defined characteristics is particularly important. In that case, when an appropriate trainee is available, the call held in that agent's cue, and the call possibly commenced, awaiting a training agent's availability.

If the training is highly structured, it is also possible to assign the trainer and trainee agents in pairs, so that the two are always available for calls together.

The system according to the present invention may also provide reinforcement for various training. Thus, if a subset of agents receive classroom training on a topic, the server may target those agents with calls relating to that topic. For example, the topic may represent a parameter of a call characterization vector. In order to target certain agents for calls having particular characteristics, a negative cost may be applied, thus increasing the probability that the agent will be selected, as compared with an agent having a positive cost. By using a single cost function, rather than specific override, the system becomes resilient, since this allocation is not treated as an exception, and therefore other parameters may be simultaneously evaluated. For example, if a caller must communicate in a foreign language, and the agent does not speak that foreign language, then the system would not target the call to that agent, even if other factors weigh in favor of such targeting.

The same techniques are available for outbound campaigns and/or mixed call centers. In this case, the cost of training is more pronounced, since agents idle for inbound tasks are generally assigned to outbound tasks, and thus the allocation of trainer agents and trainee agents generally results in both longer call duration and double the number of agents assigned per call. This cost may again be balanced by avoiding training during peak utility outbound calling hours and peak inbound calling hours; however, training opportunities should not be avoided absolutely.

According to one embodiment of the invention, at the conclusion of a call, the caller is prompted through an IVR to immediately assess the interaction, allowing a subjective scoring of the interaction by the caller without delay. This information can then be used to update the stored profile parameters for both caller and agent, as well as to provide feedback to the agent and/or trainer. Under some circumstances, this may also allow immediate rectification of an unsatisfactory result.

Figure 3:
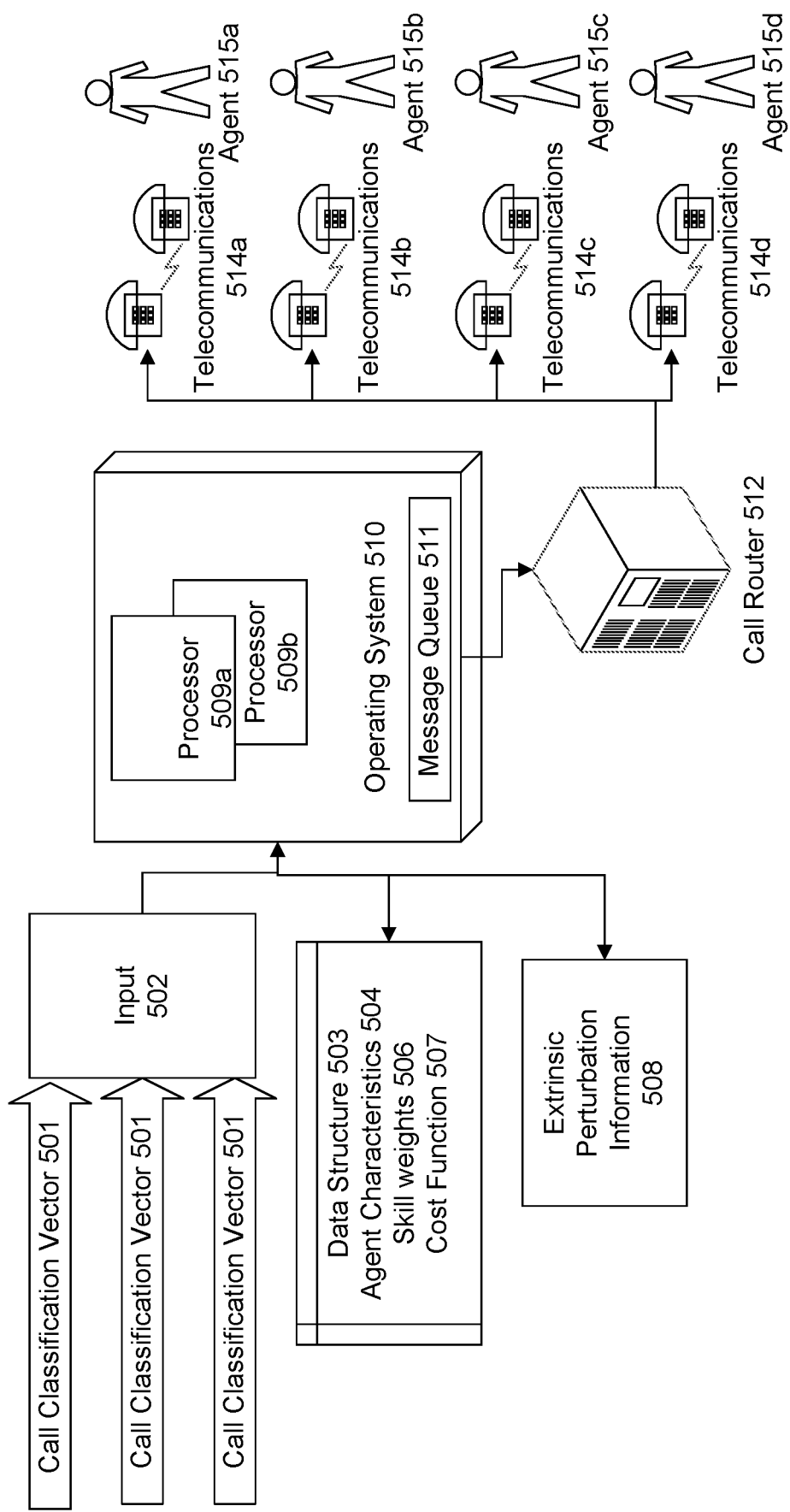
FIG. 3 shows a first block diagram in accordance with the present invention.

As shown in FIG. 3, a communications control system is shown comprising an input 502 receiving call classification information, the call classification information comprising a plurality of classification characteristics 501, a data structure 503 representing a plurality of distinct agent characteristics 504 for each of a plurality of agents; and a processor 509*a*, 509*b*, which may include a plurality of central processing units, for: (i) determining, with respect to the received call classification information, an optimum agent 515*a*, 515*b*, 515*c*, 515*d*, selected from sufficiently capable available agents for association with a call corresponding to call classification information, the determination of an optimum agent being based on a multifactorial optimization of (a) at least a non-binary weighted correspondence of said plurality of classification characteristics and (b) said plurality of distinct agent characteristics 504 for each of said plurality of agents 515*a*, 515*b*, 515*c*, 515*d*, and (ii) controlling a routing of a plurality of concurrent calls with a call router 512 in dependence on the determination. The processor may operate under control of a consolidated operating system 510. The determination and control by the processor may employ a common message queue 511 in the operating system 510. The process may maintain a data structure 503 representing skill weights 506 with respect to said call classification information 501, and applies said weights to determine an optimum agent selection. The processor may receive extrinsic perturbation information 508 independent of the plurality of classification characteristics and the plurality of distinct agent characteristics, to provide discrimination in control of call routing. A cost function may be provided for each agent 515*a*, 515*b*, 515*c*, 515*d*, the processor optimizing a cost-benefit outcome of a routing.

Figure 4:
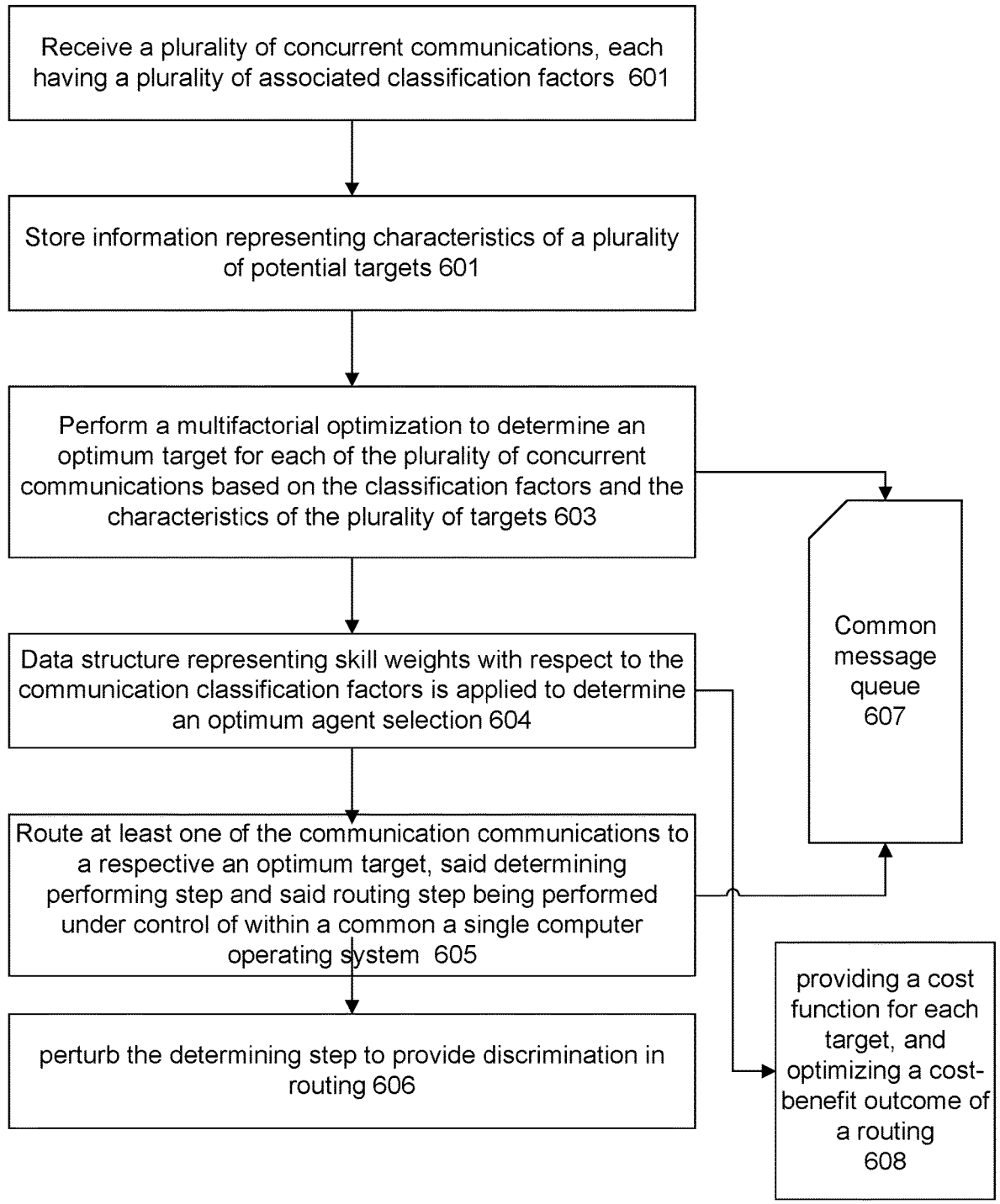
FIG. 4 shows a third flowchart in accordance with the present invention.

A plurality of call classification vectors 501 may be received, the processor being adapted to determine, with respect to the received plurality of call classification vectors 501, an optimum association of the set of agents 15*a*, 515*b*, 15*c*, 515*d*, and calls having the associated call classification vectors 501. As shown in FIG. 4, a communications method is shown comprising: (a) receiving a plurality of concurrent communications, each having a plurality of associated classification factors 601; (b) storing information representing characteristics of a plurality of potential targets; (c) performing a multifactorial optimization to determine an optimum target for each of the plurality of concurrent communications based on the classification factors and the characteristics of the plurality of targets 602; and (d) routing at least one of the communications to a respective an optimum target, said performing step and said routing step being performed under control of a single computer operating system 605.

The performing and routing may employ a common message queue in an operating system 607. A data structure representing skill weights with respect to the communication classification factors is applied to determine an optimum agent selection 604. The method may also include the step of perturbing the determining step to provide discrimination in routing 606. The determining step may comprise providing a cost function for each target, and optimizing a cost-benefit outcome of a routing 608.

FIG. 4 shows a communications control system 701, comprising at least one programmable processor 702 executing instructions stored in a computer readable medium 703, the instructions being adapted to control the at least one programmable processor to execute: (a) a multithreaded operating system, providing support for applications and for passing messages between concurrently executing applications 703; (b) a communications control server application executing under said multithreaded operating system, for controlling concurrent real time communications 704; and (c) at least one dynamically linkable application, executing under said multithreaded operating system, communicating with said communications control server application to receive call characteristic data and perform a multifactorial optimization with respect to a plurality of target characteristics for each of a plurality of available communications targets, to resolve a an optimal communications target and transmit a resolved communications target, said communications control server application controlling a plurality of concurrent real time communications in dependence on the transmitted resolved communications target 706.

Figure 6:
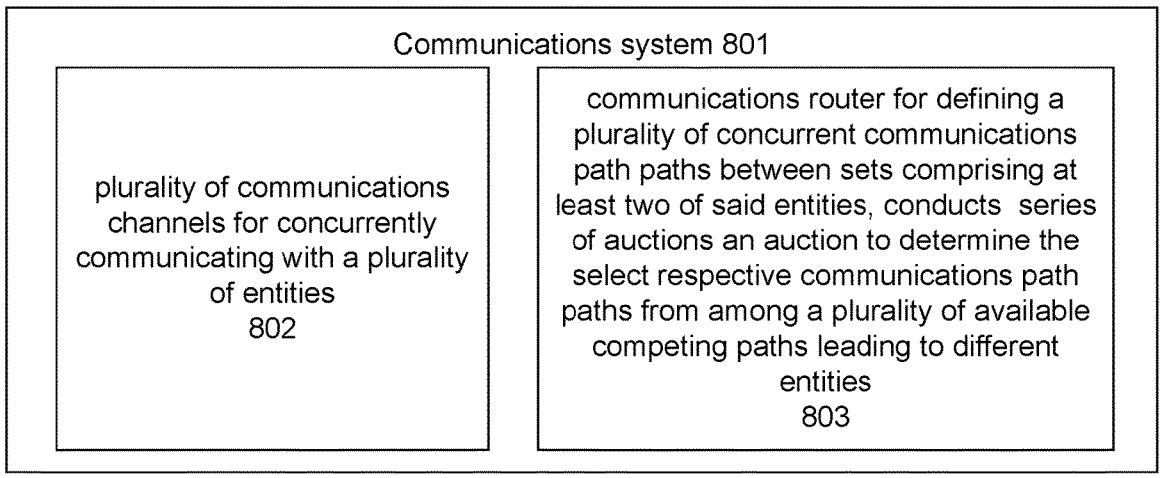
FIG. 6 shows a third block diagram in accordance with the present invention.

As shown in FIG. 6, a communications matching system 801 is shown, comprising: (a) a plurality of communications channels for concurrently communicating with a plurality of entities 802; and (b) a communications router for defining a plurality of concurrent communications paths between sets comprising at least two of said entities, wherein said communications router conducts series of auctions to select respective communications paths from among a plurality of available competing paths, wherein said series of auctions determine winners based on a valuation function which is sensitive to both economic factors and non-economic factors, wherein the non-economic factors have an effect on auction outcome which changes over time, the non-economic factors being valued at the time of the auction 803.

Figure 7:
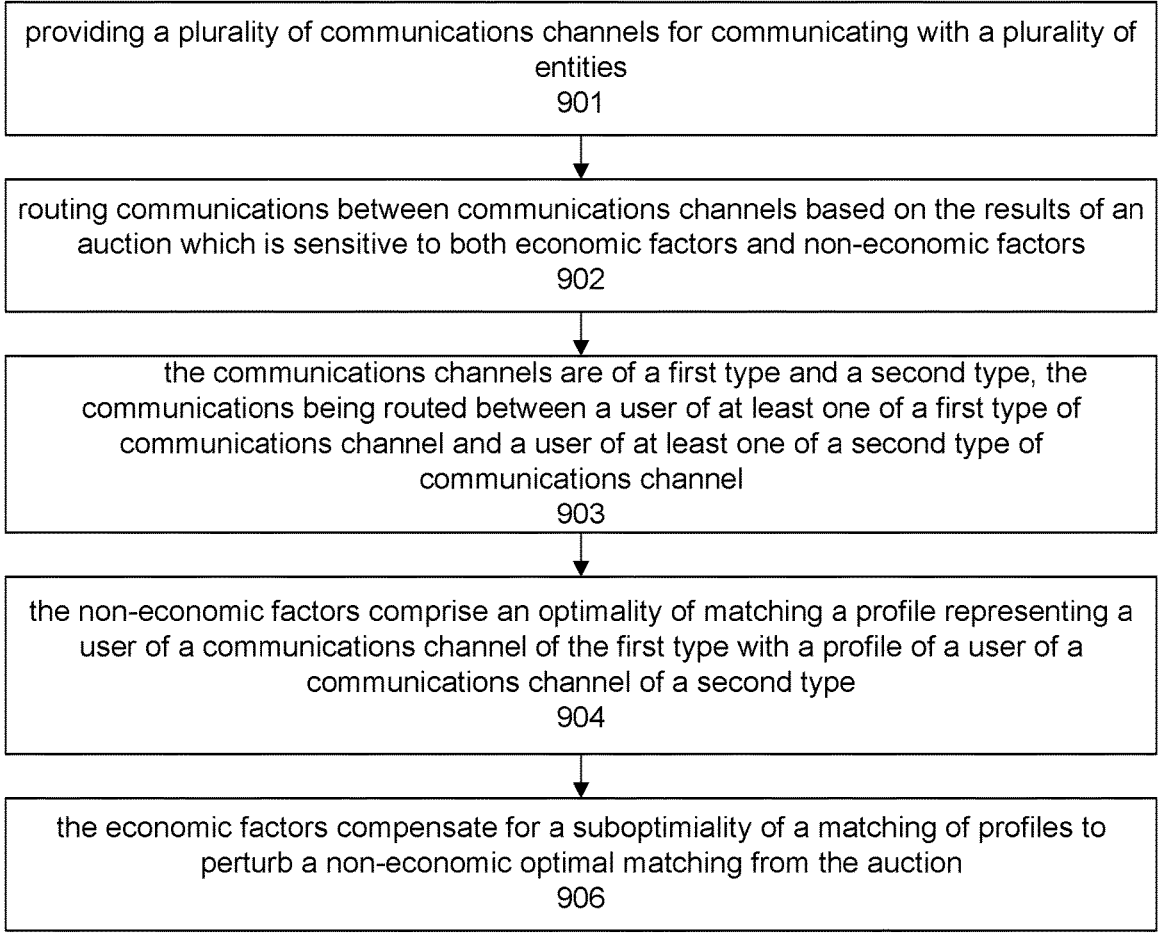
FIG. 7 shows a forth flowchart in accordance with the present invention.

As shown in FIG. 7, a communications method is shown, comprising the steps of: (a) providing a plurality of communications channels for concurrently communicating with a plurality of entities 901; and (b) automatically concurrently routing communications between a plurality of communications channels based on the results of an automated auction which determines at least one winner based on a valuation function which is sensitive to both economic factors and non-economic factors 902, wherein the non-economic factors have an effect on auction outcome which changes over time, the non-economic factors being valued at the time of the auction.

The communications channels may be of a first type and a second type, the communications being routed between a user of at least one of a first type of communications channel and a user of at least one of a second type of communications channel 903. The non-economic factors may comprise an optimality of matching a profile representing a user of a communications channel of the first type with a profile of a user of a communications channel of a second type 904.

The economic factors may compensate for a suboptimality of a matching of profiles to perturb a non-economic optimal matching from the auction 905.

Figure 8:
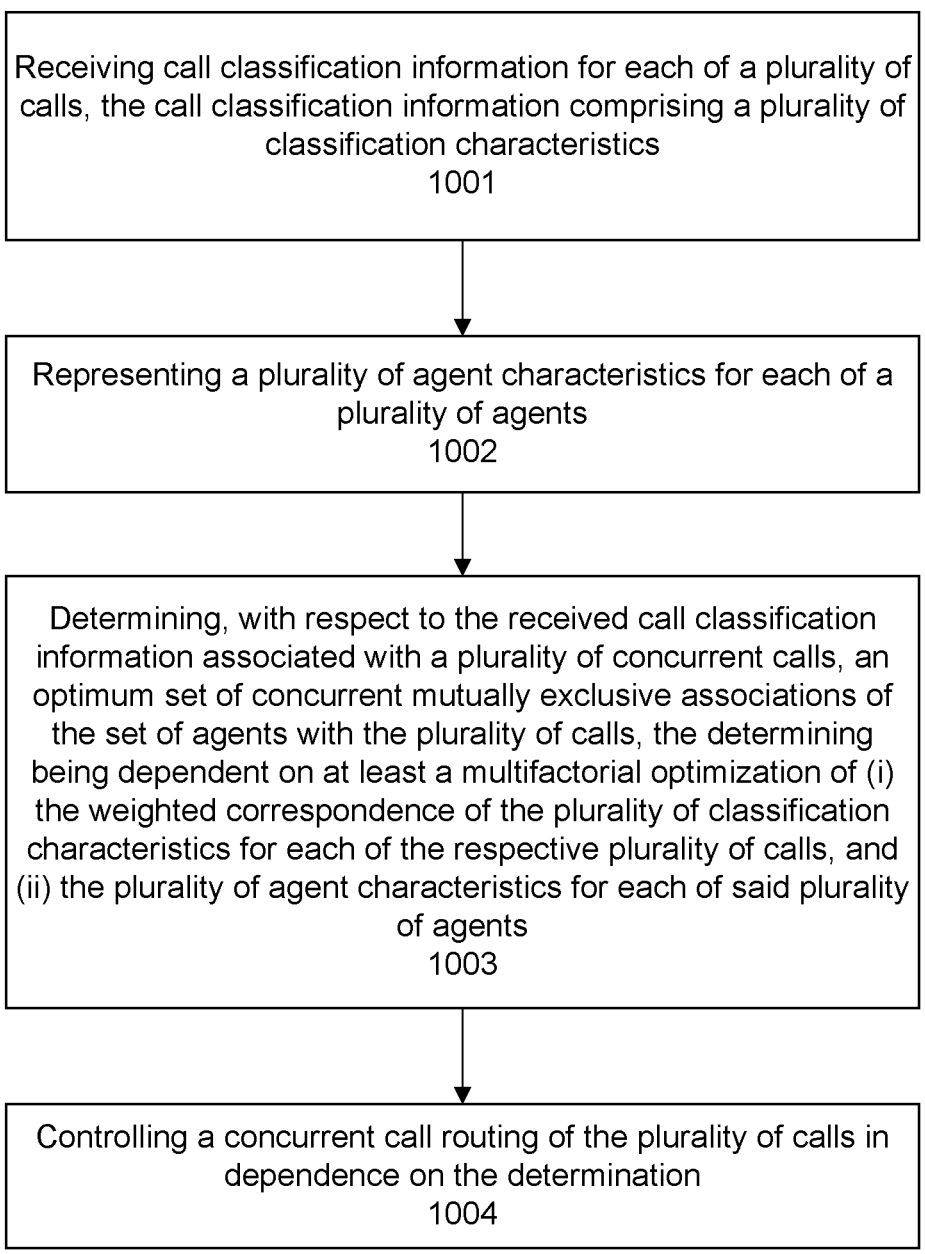
FIG. 8 shows a fifth flowchart in accordance with the present invention.

As shown in FIG. 8, a communications control method is shown, comprising the steps of: (a) receiving call classification information for each of a plurality of calls, the call classification information comprising a plurality of classification characteristics 1001; (b) representing a plurality of agent characteristics for each of a plurality of agents 1002; (c) determining, with respect to the received call classification information associated with a plurality of concurrent calls, an optimum set of concurrent mutually exclusive associations of the set of agents with the plurality of calls, the determining being dependent on at least a multifactorial optimization of (i) the weighted correspondence of the plurality of classification characteristics for each of the respective plurality of calls, and (ii) the plurality of agent characteristics for each of said plurality of agents 1003; and (d) controlling a concurrent call routing of the plurality of calls in dependence on the determination 1004.

Example 1

Each agent is classified with respect to 10 skills, and each skill can have a weight of 0 to 127. The skill weights may be entered manually by a supervisor, developed adaptively, or provided by other means. These are sent as a parameter file to the communications server.

A rule vector specifies a normalized contribution of each skill to apply to the total. This rule vector, for example, represents the call characteristic vector. Thus, attributes of the call and the status of the system are analyzed to generate this rule vector. There can be more than one rule vector defined in a project (split), or a rule can be setup in a per call basis. Generally, routing with predefined rules is much more efficient than routing with rules in a per call bases. When a call needs to be routed to an agent, the rule vector is applied to the skills of the available agents and a score is derived for each agent. The agent with the highest score is assigned the call, as shown in Table 1.

As shown in Table 1, Agent 1 would be selected, since this is the highest score.

In this example, it is presumed that all selections have the same cost, and therefore the utility only varies. Thus, the agent with the highest utility function is the optimal selection.

Example 2

The conditions below are the same as in Example 1, except two new factors are provided, Ac1 and Ac2. The Preliminary Score is calculated as the sum of the products of the Rule Vector and the Agent Vector. The Final Score is calculated as (Ac1×sum)+Ac2.

In this case, Ac1 represents an agent-skill weighting cost function, while Ac2 represents an agent cost function. Since we select the maximum value, more expensive agents have correspondingly lower cost values.

As can be seen in Table 2, Agent 5 is now optimum.

Example 3

In this example, a limiting criterion is imposed, that is, only agents with a skill score within a bound are eligible for selection. While this may be implemented in a number of ways, possibly the simplest is to define the range, which will typically be a lower skill limit only, below which an agent is excluded from selection, as a preliminary test for "availability".

As noted below in Table 3, the screening criteria may be lower, upper or range limits. In this case, the screening process excludes agents 2, 3, and 5, leaving agents 1 and 4 available. Of these two choices, agent 1 has the higher score and would be targeted. (Note: 2, 3, 5 excluded, 1, 4 available).

Example 4

In this example, the optimization seeks to optimize the placement of 5 incoming calls to 5 agents. As shown in Table 4, each caller is represented by a different call vector, and each agent by a distinct skill vector. The optimization therefore seeks the maximum utility from the respective possible pairings.

TABLE 1

| Rule vector | | | Agent 1 | Agent 2 | Agent 3 | Agent 4 | Agent 5 |
|---|---|---|---|---|---|---|---|
| 20% | Skill | 1 | 20 | 5 | 3 | 5 | 4 |
| 5% | Skill | 2 | 3 | 3 | 3 | 3 | 3 |
| 10% | Skill | 3 | 10 | 6 | 9 | 10 | 10 |

TABLE 1-continued

| Rule vector | | | Agent 1 | Agent 2 | Agent 3 | Agent 4 | Agent 5 |
|---|---|---|---|---|---|---|---|
| 15% | Skill | 4 | 43 | 50 | 33 | 46 | 25 |
| 3% | Skill | 5 | 7 | 2 | 9 | 2 | 8 |
| 7% | Skill | 6 | 5 | 8 | 5 | 8 | 9 |
| 20% | Skill | 7 | 2 | 3 | 4 | 2 | 2 |
| 8% | Skill | 8 | 64 | 80 | 29 | 45 | 77 |
| 5% | Skill | 9 | 4 | 5 | 4 | 1 | 2 |
| 7% | Skill | 10 | 9 | 3 | 8 | 3 | 6 |
| 100% | Score | | 18.51 | 17.33 | 11.1 | 13.93 | 13.65 |

TABLE 2

| Rule Vector | | | Agent 1 | Agent 2 | Agent 3 | Agent 4 | Agent 5 |
|---|---|---|---|---|---|---|---|
| | Ac1 | | 0.4 | 0.55 | 0.45 | 0.7 | 0.6 |
| | Ac2 | | 6 | 3 | 6.8 | 2 | 5.5 |
| 20% | Skill | 1 | 20 | 5 | 3 | 5 | 4 |
| 5% | Skill | 2 | 3 | 3 | 3 | 3 | 3 |
| 10% | Skill | 3 | 10 | 6 | 9 | 10 | 10 |
| 15% | Skill | 4 | 43 | 50 | 33 | 46 | 25 |
| 3% | Skill | 5 | 7 | 2 | 9 | 2 | 8 |
| 7% | Skill | 6 | 5 | 8 | 5 | 8 | 9 |
| 20% | Skill | 7 | 2 | 3 | 4 | 2 | 2 |
| 8% | Skill | 8 | 64 | 80 | 29 | 45 | 77 |
| 5% | Skill | 9 | 4 | 5 | 4 | 1 | 2 |
| 7% | Skill | 10 | 9 | 3 | 8 | 3 | 6 |
| 100% | Prelim Score | | 18.51 | 17.33 | 11.1 | 13.93 | 13.65 |
| | Final Score | | 13.40 | 12.53 | 11.80 | 11.75 | 13.69 |

TABLE 3

| Rule Vector | | | Exclude | | | Agent 1 | Agent 2 | Agent 3 | Agent 4 | Agent 5 |
|---|---|---|---|---|---|---|---|---|---|---|
| | Min Skill | Max Skill | Agent | | | | | | | |
| | | | | Ac1 | | 0.4 | 0.55 | 0.45 | 0.7 | 0.6 |
| | | | | Ac2 | | 6 | 3 | 6.8 | 2 | 5.5 |
| 20% | 0% | 25% | | Skill | 1 | 20 | 5 | 3 | 5 | 4 |
| 5% | | | | Skill | 2 | 3 | 3 | 3 | 3 | 3 |
| 10% | | | | Skill | 3 | 10 | 6 | 9 | 10 | 10 |
| 15% | 40% | 100% | 3, 5 | Skill | 4 | 43 | 50 | 33 | 46 | 25 |
| 3% | | | | Skill | 5 | 7 | 2 | 9 | 2 | 8 |
| 7% | | | | Skill | 6 | 5 | 8 | 5 | 8 | 9 |
| 20% | | | | Skill | 7 | 2 | 3 | 4 | 2 | 2 |
| 8% | 30% | 75% | 2, 3, 5 | Skill | 8 | 64 | 80 | 29 | 45 | 77 |
| 5% | | | | Skill | 9 | 4 | 5 | 4 | 1 | 2 |
| 7% | | | | Skill | 10 | 9 | 3 | 8 | 3 | 6 |
| 100% | | | | Prelim Score | | 18.51 | 17.33 | 11.1 | 13.93 | 13.65 |
| | | | | Final Score | | 13.40 | 12.53 | 11.80 | 11.75 | 13.69 |

TABLE 4

| SKILL | Rule Vector 1 | Rule Vector 2 | Rule Vector 3 | Rule Vector 4 | Rule Vector 5 | | Agent 1 | Agent 2 | Agent 3 | Agent 4 | Agent 5 |
|---|---|---|---|---|---|---|---|---|---|---|---|
| 1 | 20% | 25% | 17% | 20% | 14% | | 20 | 5 | 3 | 5 | 4 |
| 2 | 5% | 10% | 5% | 5% | 3% | | 3 | 3 | 3 | 3 | 3 |
| 3 | 10% | 15% | 20% | 10% | 8% | | 10 | 6 | 9 | 10 | 10 |
| 4 | 15% | 10% | 5% | 5% | 5% | | 43 | 50 | 33 | 46 | 25 |
| 5 | 3% | 0% | 5% | 8% | 1% | | 7 | 2 | 9 | 2 | 8 |
| 6 | 7% | 10% | 13% | 10% | 7% | | 5 | 8 | 5 | 8 | 9 |
| 7 | 20% | 10% | 5% | 10% | 20% | | 2 | 3 | 4 | 2 | 2 |
| 8 | 8% | 4% | 8% | 4% | 8% | | 64 | 80 | 29 | 45 | 77 |
| 9 | 5% | 8% | 13% | 18% | 23% | | 4 | 5 | 4 | 1 | 2 |
| 10 | 7% | 8% | 9% | 10% | 11% | | 9 | 3 | 8 | 3 | 6 |
| | 100% | 100% | 100% | 100% | 100% | Rule 1 | 18.51 | 17.33 | 11.1 | 13.93 | 13.65 |
| | | | | | | Rule 2 | 15.4 | 12.39 | 8.72 | 10.77 | 10.12 |
| | | | | | | Rule 3 | 15.25 | 13.31 | 8.97 | 10.54 | 12.71 |
| | | | | | | Rule 4 | 12.74 | 9.91 | 7.6 | 7.89 | 8.98 |
| | | | | | | Rule 5 | 13.69 | 12.83 | 8.24 | 9.03 | 11.09 |

TABLE 6

| SKILL | Rule Vector 1 | Rule Vector 2 | Rule Vector 3 | Rule Vector 4 | Rule Vector 5 | | Agent 1 | Agent 2 | Agent 3 | Agent 4 | Agent 5 |
|---|---|---|---|---|---|---|---|---|---|---|---|
| Caller time factor | 3 | 3.5 | 2.75 | 4 | 10 | | | | | | |
| | | | | | | Agent Cost | 0.59 | 0.68 | 1 | 0.86 | 0.79 |
| | | | | | | Agent time factor | 1.3 | 1.3 | 1 | 1.1 | 1.2 |
| 1 | 20% | 25% | 17% | 20% | 14% | | 20 | 5 | 3 | 5 | 4 |
| 2 | 5% | 10% | 5% | 5% | 3% | | 3 | 3 | 3 | 3 | 3 |
| 3 | 10% | 15% | 20% | 10% | 8% | | 10 | 6 | 9 | 10 | 10 |
| 4 | 15% | 10% | 5% | 5% | 5% | | 43 | 50 | 33 | 46 | 25 |
| 5 | 3% | 0% | 5% | 8% | 1% | | 7 | 2 | 9 | 2 | 8 |
| 6 | 7% | 10% | 13% | 10% | 7% | | 5 | 8 | 5 | 8 | 9 |
| 7 | 20% | 10% | 5% | 10% | 20% | | 2 | 3 | 4 | 2 | 2 |
| 8 | 8% | 4% | 8% | 4% | 8% | | 64 | 80 | 29 | 45 | 77 |
| 9 | 5% | 8% | 13% | 18% | 23% | | 4 | 5 | 4 | 1 | 2 |
| 10 | 7% | 8% | 9% | 10% | 11% | | 9 | 3 | 8 | 3 | 6 |
| | 100% | 100% | 100% | 100% | 100% | Rule 1 | 72.189 | 58.80069 | 19.647 | 31.71861 | 36.855 |
| | | | | | | Rule 2 | 70.07 | 49.045815 | 18.0068 | 28.610505 | 31.878 |
| | | | | | | Rule 3 | 54.51875 | 41.3974275 | 14.553825 | 21.999615 | 31.45725 |
| | | | | | | Rule 4 | 66.248 | 44.83284 | 17.936 | 23.95404 | 32.328 |
| | | | | | | Rule 5 | 177.97 | 145.1073 | 48.616 | 68.5377 | 99.81 |

TABLE 5

Combinatorial analysis of agents vs. callers

| | | | | | | | | | | | | | | | | | | | |
|---|---|---|---|---|---|---|---|---|---|---|---|---|---|---|---|---|---|---|---|
| 58.85 | 59.52 | 58.77 | 59.58 | 60.68 | 58.79 | 58.04 | 58.85 | 60.28 | 57.72 | 58.12 | 58.93 | 60.42 | 57.86 | 59.01 | 60.15 | 59.26 | 56.7 | 59.96 | 58.18 |
| 57.88 | 58.55 | 58.88 | 60.66 | 59.71 | 57.82 | 58.15 | 59.93 | 59.31 | 56.75 | 55.41 | 57.19 | 60.53 | 57.97 | 56.3 | 57.33 | 60.34 | 57.78 | 57.25 | 55.36 |
| 60.13 | 61.28 | 59.25 | 60.06 | 61.96 | 61.33 | 59.3 | 60.11 | 62.04 | 60.26 | 58.9 | 59.71 | 60.9 | 59.12 | 59.79 | 60.93 | 59.74 | 57.96 | 58.63 | 58.96 |
| 60.24 | 49.54 | 56.54 | 58.32 | 62.07 | 58.99 | 56.96 | 58.74 | 59.33 | 57.92 | 56.56 | 58.34 | 58.19 | 56.78 | 57.45 | 58.48 | 58 | 56.59 | 57.26 | 56.51 |
| 58.66 | 59.81 | 60.14 | 62.42 | 60.49 | 59.86 | 60.19 | 62.47 | 60.57 | 58.79 | 57.45 | 59.73 | 61.79 | 60.01 | 58.34 | 58.59 | 62.1 | 60.32 | 58.65 | 56.62 |
| 59.74 | 58.07 | 57.32 | 59.6 | 61.57 | 58.49 | 57.74 | 60.02 | 58.83 | 57.42 | 57.82 | 60.1 | 58.97 | 57.56 | 58.71 | 58.96 | 59.28 | 57.87 | 59.02 | 56.99 |

TABLE 7

Combinatorial Analysis

| | | | | | | | | | |
|---|---|---|---|---|---|---|---|---|---|
| 259.5527 | 255.3573 | 256.8383 | 289.6307 | 267.1886 | 254.8785 | 256.3595 | 289.1519 | 255.0903 | 246.9756 |
| 236.6543 | 232.4589 | 235.0236 | 290.7144 | 244.2902 | 231.9801 | 234.5448 | 290.2356 | 232.1919 | 224.0773 |
| 260.9804 | 259.9429 | 259.9962 | 292.7886 | 268.6163 | 260.932 | 260.9853 | 293.7777 | 259.6759 | 253.0292 |
| 239.1658 | 163.4004 | 231.9914 | 287.6822 | 246.8016 | 234.7961 | 234.8494 | 290.5402 | 231.6711 | 226.8933 |
| 224.1784 | 223.1409 | 225.7056 | 295.3001 | 231.8143 | 224.13 | 226.6947 | 296.2892 | 222.8739 | 216.2272 |
| 225.2621 | 218.0345 | 219.5155 | 289.1099 | 232.898 | 220.8925 | 222.3735 | 291.9679 | 217.7675 | 212.9896 |
| 247.4191 | 280.2116 | 264.8651 | 256.7504 | 255.7129 | 291.0701 | 309.1051 | 300.9904 | 367.4349 | 302.5176 |
| 219.4143 | 275.1051 | 243.0504 | 234.9358 | 227.7081 | 284.8799 | 310.1888 | 302.0741 | 339.4301 | 296.3275 |
| 248.887 | 281.6795 | 268.023 | 261.3763 | 257.1808 | 292.538 | 312.263 | 305.6163 | 301.4208 | 303.9855 |
| 222.7511 | 278.4419 | 240.0182 | 235.2403 | 231.0449 | 288.2167 | 307.1566 | 302.3787 | 298.1833 | 299.6643 |
| 211.5642 | 281.1587 | 233.7324 | 227.0857 | 219.858 | 289.5057 | 314.7744 | 308.1277 | 300.9 | 300.9533 |
| 213.4331 | 283.0276 | 227.5423 | 222.7644 | 221.7269 | 291.3746 | 308.5843 | 303.8064 | 302.7689 | 302.8222 |

Using a combinatorial analysis, as shown in Table 5, the maximum value is 62.42, which represents the selection of agent 1/caller 1; agent 2/caller 5; agent 3/caller 4; agent 4, caller 2; and agent 5, caller 3.

Example 5

Similar to Example 4, it is also possible to include an agent cost analysis, to provide an optimum cost-utility function. As in Example 2, the cost factors are reciprocal, since we select the largest value as the optimum. Likewise, time factors are also reciprocal, since we seek to minimize the time spent per call. In this case, shown in Table 6, the cost analysis employs three additional parameters: the agent cost, a value representing the cost of the agent per unit time; a value representing an anticipated duration of the call based on the characteristics of the caller; and a value representing the anticipated duration of the call based on characteristics of the agent.

As can be seen in Table 7, the maximum value is 314.78, which corresponds to a selection of: Agent 1/Call 5; Agent 2/Call 1; Agent 3/Call 4; Agent 4/Call 2; and Agent 5/Call 3.

Therefore, it is seen that the optimum agent/caller selection is sensitive to these cost factors.

It is also seen that, while the analysis can become quite complex, the formulae may be limited to evaluation of simple arithmetic functions, principally addition and multiplication, with few divisions required. Thus, these calculations may be executed efficiently in a general purpose computing environment.

Example 6

Geographic information may be used as a basis for communications routing. Mobile phones are or will be capable of geolocation, meaning that the location of the handset may be automatically determined in real time and communicated. Likewise, a location of landlines can typically be determined. There are a number of instances where this information may then advantageously be used to route calls. For example, a call to a national pizza delivery chain toll free number or central facility may be automatically routed to a geographically proximate local franchisee, or, if a number are available, to one of a qualified group. It is noted that while the communications are preferably voice communications, other type of communications may be supported.

However, it is also possible to perform evaluation of more complex algorithms in order to determine a set of communications partners. For example, a geographic factor, a past history, and/or user profile may be available to describe the caller. This information may provide, for example, a preferred language, a contact report (identifying likely issues), demographic information, and user personality (as determined from a prior communication). Likewise, an interactive voice or keypad response system can glean further information to determine the issues involved in the call. Using this information, a vector may be provided describing the caller and the likely issues of the call, which may then be used to optimize a targeting of the call to available recipients. The maintenance of vectors to describe available call targets is described above.

In cases where multiple recipients are available and have, within a reasonable range, equivalent or super-threshold qualifications or suitability to receive the call, it may be appropriate for the potential recipients to compete for the call. That is, the optimization of targeting (e.g., pairing of a caller and callee) includes an economic component, optionally with a non-economic component. For example, the potential recipients each submit a bid for the call, with the call being routed to the auction winner (which may be a payment to or from the recipient, depending on the circumstances of the auction) at, for example, a first or second price, according to the auction rules.

In a typical case, the routing server has a direct and prearranged financial arrangement with the bidders, and the auction process does not directly involve the caller. On the other hand, other cases allow the caller to be involved in the auction as a "buyer" or "seller", with the communications router serving only in the capacity of auctioneer, and not a principal to the auction.

In cases where the potential recipients do not all have equivalent qualifications, a normalization function may be applied to correct the bids. For example, a potential recipient with a 60% match with the required qualification profile might have to bid 50% more than a potential recipient with a 90% match, assuming that the matching function linearly corresponds with an economic factor; otherwise, a non-linear normalization may be applied. This is equivalent to providing that the value applied to determine the auction winner includes a component representing an economic value and a component representing a non-economic value, e.g., a match or optimality score for the call, which is determined for each bidder to determine the winner. The bidder in this case may either have knowledge of the match score, or may bid blind.

In a commission based system, for example, an agent with a higher sales average performance might have to bid a lower amount than an agent with lower performance, the difference being an amount which tends to equalize (but not necessarily completely equalize) the anticipated payoff from the call, thus incentivizing higher sales performance. In any case, the communications router (or a separate system which communicates with the communications router in some embodiments) evaluates the bids including both economic and non-economic components, determines the winning bidder, and determines the communications path(s).

In another embodiment, a group of agents within a call center have performance goals for a shift, with possible gradation between agents of the goals based on compensation, seniority, etc. The agents are within a queue, in which the default is a sequential selection of available agents. However, an agent may seek to take a break, and therefore bids for a lower position within the queue. Likewise, an agent may find him or herself behind in performance, and wish to bid for higher placement within the queue. As discussed above, the bid cost or perturbation effect may be normalized based on a variety of factors and schemes, including the optimality of matching. In this scheme, the auction may be economic or non-economic. In a non-economic scheme, each agent is provided with a set of bid units, for example 100 per shift. The bid units may then be applied to advance within the queue, or even traded with another agent (although this possibility leaves open the issue of undesired indirect real economic effects, since the trade may involve extrinsic value).

Another possibility is the ad hoc formation of chat groups. In this case, the composition of the group is optimized based on the respective profile vectors of the members. In some cases, the ideal or optimum is minimum variance of the vectors, but in other cases optimality may require complementary components. Assuming multiple chat groups and multiple callers, there may be a market economy for matching a caller with a group. In such a scenario, a VCG type auction may be conducted, with the composition of each group allocated based on an optimization of bid values. An example of this is a sports chat line. A number of fans and sports celebrities contact a call center and are identified and a profile applied. Using market principles, the groups are formed to maximize the utility aggregate functions. Thus, a group of "high rollers" may gain the benefit of a superstar, while neophytes may only communicate with a rookie, with the set of groups optimized to achieve maximum utility.

An automated chat system may also be used for dating services, adult theme entertainment, business services, consumer services, or the like. In these systems, the communications router typically taxes some of the economic surplus generated by the system, in a real economic form, while benefiting the various classes of user.

It is noted that the auction may involve transfer of real economic benefits, or a synthetic economy constructed within a closed system. For example, micropayment technologies may be employed to authorize and convey the value between entities, even through an open network, without having to trust all entities within the chain of custody.

The bidding may be a volitional real time event, allowing those involved to make decisions on the spot; but more typically, a bidder will define a personal value function, which is then used in an automated auction process. The bidder will therefore provide an indirect control over the bidding on his or her behalf, for example using feedback to tune the attributed value function to a desired value. In auction types where broadcast of a true value is a dominant strategy, the function itself may be presented as a bid (assuming that the auctioneer has sufficient information to evaluate the function), otherwise, it may be evaluated under the circumstances and a normalized value transmitted. The auctioneer is, in this case, the communications arbitrator or switch. In a successive price auction, the value function itself is preserved, although the dropout pattern may be noted, allowing an estimation of the value function of competitors.

It should be clear that there are many possible scenarios which allow callers and/or potential recipients to compete for a connection, and therefore a large variety of auction types may be implemented accordingly.

The present system differs from a known telecommunications auction in that, for example, it is sensitive to user characteristics, and does not treat each communications line as a simple commodity.

From the above description and drawings, it will be understood by those of ordinary skill in the art that the particular embodiments shown and described are for purposes of illustration only and are not intended to limit the scope of the invention. Those of ordinary skill in the art will recognize that the invention may be embodied in other specific forms without departing from its spirit or essential characteristics. References to details of particular embodiments are not intended to limit the scope of the claims.

It should be appreciated by those skilled in the art that the specific embodiments disclosed above may be readily utilized as a basis for modifying or designing other structures for carrying out the same purposes of the present invention. It should also be realized by those skilled in the art that such equivalent constructions do not depart from the spirit and scope of the invention as set forth in the appended claims.

REFERENCES

Adomavicius, Gediminas, and Alexander Tuzhilin. "Extending recommender systems: A multidimensional approach." In *Proceedings of the International Joint Conference on Artificial Intelligence (IJCAI-01), Workshop on Intelligent Techniques for Web Personalization (ITWP2001)*, Seattle, Wash., August, pp. 4-6. 2001. www.mineit.com/lc/ijcai/papers/adomavicius.pdf Adomavicius, Gediminas, and Alexander Tuzhilin. "Using data mining methods to build customer profiles." *Computer* 34, no. 2 (2001): 74-82. www.eng.auburn.edu/users/wenchen/mining.pdf Aggarwal, Charu C. "On the effects of dimensionality reduction on high dimensional similarity search." In *Proceedings of the twentieth ACM SIGMOD-SIGACT-SIGART symposium on Principles of database systems*, pp. 256-266. ACM, 2001. web.mit.edu/charu/www/dim.ps Aggarwal, Charu C., Joel L. Wolf, Kun-Lung Wu, and Philip S. Yu. "Horting hatches an egg: A new graph-theoretic approach to collaborative filtering." In *Proceedings of the fifth ACM SIGKDD international conference on Knowledge discovery and data mining*, pp. 201-212. ACM, 1999. web.mit.edu/charu/wvvw/kdd386.ps Aguzzoli, Stefano, Paolo Avesani, and Paolo Massa. "Compositional CBR via collaborative filtering." In *Proceedings of ICCBR, vol. 1*. 2001. sra.itc.it/tr/AAM01.ps.gz Almeida, Joao Paulo Andrade, Giancarlo Guizzardi, and José Gonçalves Pereira Filho. "Agent-Mediators in Media on Demand Eletronic Commerce." In *VII International Congress of new technologies and Computer Applications*, Cuba. 2000. wwwhome.cs.utwente.nl/~guizzard/mod-amec-cuba.pdf Amento, Brian, Loren Terveen, and Will Hill. "Does "authority" mean quality? Predicting expert quality ratings of Web documents." In *Proceedings of the 23rd annual international ACM SIGIR conference on Research and development in information retrieval*, pp. 296-303. ACM, 2000. www.research.att.com/~terveen/sigir2000.ps Ardissono, Liliana, and Anna Goy. "Tailoring the interaction with users in web stores." *User Modeling and User-Adapted Interaction* 10, no. 4 (2000): 251-303. www.di.unito.it/~liliana/EC/umuai-per-www.ps.gz Ardissono, Liliana, Luca Console, and Ilaria Torre. "An adaptive system for the personalized access to news." *Ai Communications* 14, no. 3 (2001): 129-147. www.di.unito.it/~liliana/EC/aiComm01.pdf Aron, Ravi, Arun Sundararajan, and Siva Viswanathan. "Intelligent agents in electronic markets for information goods: customization, preference revelation and pricing." *Decision Support Systems* 41, no. 4 (2006): 764-786. oz.stern.nyu.edu/papers/agent.pdf Asdoorian, Mark. "Data manipulation services in the Haystack IR system." PhD diss., Massachusetts Institute of Technology, 1998. grebe.lcs.mit.edu/papers/Asdoorian.thesis.ps.gz Bakos, Yannis. "The emerging role of electronic marketplaces on the Internet." *Communications of the ACM* 41, no. 8 (1998): 35-42. www-ec.njit.edu/~bartel/B2Breports/EmergingRoleOfElectronicMarketplaces.pdf Basu, Chumki, Haym Hirsh, William W. Cohen, and Craig G. Nevill-Manning. "Technical paper recommendation: A study in combining multiple information sources." *J. Artif. Intell. Res. (JAIR)* 14 (2001): 231-252. www.cs.washington.edu/research/jair/volume14/basu01a.ps Baudisch, Patrick, and Lars Brueckner. "TV Scout: Lowering the entry barrier to personalized TV program recommendation." In *International Conference on Adaptive Hypermedia and Adaptive Web-Based Systems*, pp. 58-68. Springer Berlin Heidelberg, 2002. ipsi.fhg.de/~baudisch/publications/2002-Baudisch-AH2002-TVScoutLoweringTheEntryBarrier.pdf Baudisch, Patrick. "Joining collaborative and content-based filtering." In *Proceedings of the ACM CHI Workshop on Interacting with Recommender Systems*, pp. 1-3. 1999. ipsi.fhg.de/~baudisch/publications/1999-Baudisch-RecSys99-JoiningCollaborativeAndContent-basedFiltering.pdf Baudisch, Patrick. "Recommending TV Programs: How far can we get at zero user effort?" In *AAAI Workshop on Recommender Systems*. 1998. www-cui.darmstadt.gmd.de/~baudisch/Publications/baudisch1998b Recommending TVProgramsAtZeroUserEffort.ps Baudisch, Patrick. "The Profile Editor: designing a direct manipulative tool for assembling profiles." In *Proceedings of Fifth DELOS Workshop on Filtering and Collaborative Filtering*, vol. 7. 1997. www.ercim.org/publication/ws-proceedings/DELOS5/delos5.pdf Baudisch, Patrick. Dynamic information filtering. GMD-Forschungszentrum Informationstechnik, 2001. ipsi.fhg.de/~baudisch/publications/2001-Baudisch-Dissertation-DynamicInformationFiltering.pdf Bennett, Paul N. "Text categorization through probabilistic learning: Applications to recommender systems." (1998). ftp.cs.utexas.edu/pub/mooney/papers/pbennett-ugthesis.ps.Z Bhaysar, Virendra C., Ali A. Ghorbani, and Stephen Marsh. "A performance evaluation of the acorn architecture." In *High Performance Computing Systems and Applications*, pp. 9-19. Springer, Boston, Mass., 2002. www.cs.unb.ca/profs/ghorbani/ali/./papers/hpcs00.ps Bibliography—Agrawal Mannila www.cs.cmu.edu/~TextLearning/pww/papers/PhD/PhDBib.ps.gz Billsus, Daniel, and Michael J. Pazzani. "Learning Collaborative Information Filters." In *Icml*, vol. 98, pp. 46-54. 1998.www.ics. uci.edu/-dbillsus/papers/icm198.pdf Blanzieri, E., and A. Ebranati. *COOL-TOUR: A case based reasoning system for tourism culture support*. Technical Report 0002-05, Istituto Trentino di Cultura, 2000. sra.itc.it/tr/BE00.ps.gz Blanzieri, E., and P. Giorgini. "From collaborative filtering to implicit culture." In *Proceedings of the workshop on agents and recommender systems*. 2000. www.cs.unitn.it/~pgiorgio/papers/wars2000.ps.gz Blanzieri, E., P. Giorgini, P. Massa, and S. Recta. "Collaborative Filtering via Implicit Culture Support." *Preliminary version submitted to UM*2001 (11 Nov. 2000) (2000). www.science.unitn.it/~pgiorgio/ic/ic-um2001.ps.gz Blanzieri, E., P. Giorgini, P. Massa, and S. Recla. "Data mining, decision support and meta-learning: towards an implicit culture architecture for KDD." In *Proc. Workshop Positions, Developments Future Directions Connection IDDM-*2001, pp. 9-20. 2001. www.science.unitn.it/~pgiorgio/ic/ws01.ps.gz Blanzieri, Enrico, and Paolo Giorgini. "Implicit Culture for Information Agents." In *AgentLink*, pp. 152-164. 2003. www.science.unitnit/~pgiorgio/ic/blanzieri-giorgini.pdf.gz Boley, Daniel, Maria Gini, Robert Gross, Eui-Hong Sam Han, Kyle Hastings, George Karypis, Vipin Kumar, Bamshad Mobasher, and Jerome Moore. "Document categorization and query generation on the world wide web using webace." *Artificial Intelligence Review* 13, no. 5-6 (1999): 365-391. www-users.cs.umn.eduhgross/papers/aij.agent.ps Bollen, Johan, and Francis Heylighen. "A system to restructure hypertext networks into valid user models." *New Review of HyperMedia and Multimedia* 4, no. 1 (1998): 189-213. lib-www.lanl.gov/~jbollen/pubs/JBollen_NRHM99.pdf Borking, John J., B. M. A. Van Eck, P. Siepel, and P. J. A. Verhaar. Intelligent software agents and privacy. The Hague: Registratiekamer, 1999. www.ipc.on.ca/english/pubpres/papers/isat.pdf Boticario, Jesus G., and Elena Gaudioso. "A multiagent architecture for a web-based adaptive educational system." *Papers from the* (2000): 20-22. newatlantis.isle.org/~aui/papers/JBoticario00.ps Boutilier, C. and Zemel, R. S.: Online queries for collaborative filtering. Ninth International Workshop on Artificial Intelligence and Statistics (2002). www.cs.toronto.edu/~cebly/Papers/_download_/querycf.ps Boutilier, Craig, Ronen I. Brafman, Holger H. Hoos, and David Poole. "Reasoning with conditional ceteris paribus preference statements." In *Proceedings of the Fifteenth conference on Uncertainty in artificial intelligence*, pp. 71-80. Morgan Kaufmann Publishers Inc., 1999. www.cs.ubc.ca/spider/hoos/Publ/uai99.ps.gz www.cs.ubc.ca/spider/cebly/Papers/CPnets.ps Bradley, Keith, Rachael Rafter, and Barry Smyth. "Case-based user profiling for content personalisation." In *Adaptive Hypermedia and Adaptive Web-Based Systems*, pp. 62-72. Springer Berlin/Heidelberg, 2000. kermit.ucd.ie/casper/ah2000bradley.ps Brandberg, Gustaf. "Query Expansion using Collaborative Filtering Algorithm." *Information Technology Department of Information Technology*, Uppsala University (2001). ftp.csd.uu.se/pub/papers/masters-theses/0207-brandberg.pdf Branting, L. Karl. "Active exploration in instance-based preference modeling." *Lecture notes in computer science* (1999): 29-43. pyramid.cs.uwyo.edu/~karl/papers/iccbr99a.ps Branting, L. Karl. "Learning feature weights from customer return-set selections." *Knowledge and Information Systems* 6, no. 2 (2004): 188-202. www.karlbranting.net/papers/kais.ps; pdfs.semanticscholar.org/b5a9/c184f6ab8a66ca1f51dd66de79458ee57be6.pdf Branting, L. Karl. "Optimizing return-set size for requirements satisfaction and cognitive load." In *Electronic Commerce*, 2002. Proceedings. Third International Symposium on, pp. 96-102. IEEE, 2002. www.karlbranting.net/papers/isec-2002.ps Breese, John S., David Heckerman, and Carl Kadie. "Empirical analysis of predictive algorithms for collaborative filtering." In *Proceedings of the Fourteenth conference on Uncertainty in artificial intelligence*, pp. 43-52. Morgan Kaufmann Publishers Inc., 1998.www.cs.auc.dk/research/DSS/papers/ALM002a.ps Brown, Eric W., and Alan F. Smeaton. "Hypertext information retrieval for the Web." In *ACM SIGIR Forum*, vol. 32, no. 2, pp. 8-13. ACM, 1998. lorca.compapp.dcuie/SIGIR98-wshop/SIGIR-Forum-summary.ps Bruckman, Amy, Thomas Erickson, Danyel Fisher, and Christopher Lueg. "Dealing with community data." In CSCW 2000 workshop. Philadelphia USA: ACM. 2000. www.cs. berkeley.eduhdanyelf/research/cscw-workshop.pdf Bulletin of the Technical Committee on Data Engineering, March 2000, Vol 23, No 1, sites.computer.org/debull/A00mar/marA00-a4final.ps Buono, Paolo, Maria Francesca Costabile, Stefano Guida, and Antonio Piccinno. "Integrating user data and collaborative filtering in a web recommendation system." In *Workshop on Adaptive Hypermedia*, pp. 315-321. Springer, Berlin, Heidelberg, 2001. wwwis.win.tue.nl/ah2001/papers/costabile.pdf Burke, Robin. "A case-based reasoning approach to collaborative filtering." *Advances in Case-Based Reasoning* (2000): 49-71. www.ics.uci.eduhburke/research/papers/burke-ewcbr00.pdf Burke, Robin. "Integrating knowledge-based and collaborative-filtering recommender systems." In Proceedings of the Workshop on AI and Electronic Commerce, pp. 69-72. 1999. www.ics. uci.edu/-burke/research/papers/burke-aiec99.pdf Burke, Robin. "Semantic ratings and heuristic similarity for collaborative filtering." In *AAAI Workshop on Knowledge-based Electronic Markets*, pp. 14-20. 2000. ecommerce.cbe.fullerton.eduhrburke/pubs/burke-kbem00.pdf www.igec.umbc.edu/kbem/final/burke.pdf Canny, John. "Collaborative filtering with privacy." In *Security and Privacy*, 2002. Proceedings. 2002 IEEE Symposium on, pp. 45-57. IEEE, 2002. www.cs.berkeley.edu/Hfc/papers/02/IEEESP02.pdf Carbonell, Jaime, Mark Craven, Steve Fienberg, Tom Mitchell, and Yiming Yang. "Report on the CONALD Workshop on Learning from Text and the Web." Pittsburgh, Pa., June (1998). www.cs.cmu.edu/~yiming/papers.yy/conald98-report.ps Cayzer, Steve, and Uwe Aickelin. "A recommender system based on the immune network." In Evolutionary Computation, 2002. CEC'02. Proceedings of the 2002 Congress on, vol. 1, pp. 807-812. IEEE, 2002. www-uk.hpl.hp.com/people/steve_cayzer/Publications/020514Immune_Recommender.pdf Cayzer, Steve, and Uwe Aickelin. "On the effects of idiotypic interactions for recommendation communities in artificial immune systems." Browser Download This Paper (2002). www.aber.ac.uk/icaris-2002/Proceedings/paper-16/paper16.pdf Chai, Wei, and Barry Vercoe. "Using User Models in Music Information Retrieval Systems." In *ISMIR*. 2000. www.media.mitedu/~chaiwei/papers/usermodeling.pdf Chalmers, Matthew, Kerry Rodden, and Dominique Brodbeck. "The order of things: activity-centred information access." Computer Networks and ISDN Systems 30, no. 1-7 (1998): 359-367. www.ubs.com/e/index/about/ubilab/print_versions/ps/cha98.ps.gz Chalmers, Matthew. "Information awareness and representation." *Computer Supported Cooperative Work (CSCW). An International Journal* (2001). www.dcs.glasgow.ac.uk/personal/personal/matthew/papers/awareness-Repn.pdf Chalmers, Matthew. "Paths and Contextually Specific Recommendation." In *DELOS Workshop: Personalisation and Recommender Systems in Digital Libraries*. 2001. www.ercim.org/publication/ws-proceedings/DelNoe02/MathewChalmers.pdf Chandrinos, Konstantinos, John Immerkr, Martin Dorr, and Panos Trahanias. "A Visual Tagging Technique for Annotating Large-Volume Multimedia Databases." In *ERCIM 5th DELOS Workshop, Budapest, Hungary*. 1997. www.ics.forth.grhkostel/papers/delos5.ps.gz Chee, Sonny Han Seng, Jiawei Han, and Ke Wang. "Rectree: An efficient collaborative filtering method." In *DaWaK*, vol. 1, pp. 141-151. 2001. www.cs.sfu.cahwangk/pub/dawakfin.pdf Chen, Zhixiang, Xiannong Meng, Richard H. Fowler, and Binhai Zhu. "FEATURES: Real-time adaptive feature and document learning for web search." *Journal of the Association for Information Science and Technology* 52, no. 8 (2001): 655-665. www.cs.panam.edu/~chen/./paper-file/features.ps.Z Cheng, Heyning Adrian. "Knowledgescapes: A probabilistic model for mining tacit knowledge for information retrieval." University of California, Berkeley (2001). www.cs.berkeley.edu/~jfc/papers/01/heyning/ms_knowledgescapes.pdf Chircu, Alina M., and Robert J. Kauffman. "The 'eBay of Blank': Digital Intermediation in Electronic Commerce." (2000). webfoot.csom.umn.edu/faculty/phds/achircu/researchweb/ck_bh_2000.pdf Cho, Hichang, Social Network Analysis of Information Sharing Networks. newmedia.colorado.edu/cscl/88.pdf Claypool, Mark, Anuja Gokhale, Tim Miranda, Paul Murnikov, Dmitry Netes, and Matthew Sartin. "Combing content-based and collaborative filters in an online newspaper." In Proceedings of ACM SIGIR workshop on recommender systems, Vol. 60. (1999) www.cs.umbc.eduhian/sigir99-rec/papers/claypool_m.ps.gz www.cs.umbc.edu/~ian/sigir99-rec/papers/claypool_m.ps.gz Claypool, Mark, David Brown, Phong Le, and Makoto Waseda. "Inferring user interest." *IEEE Internet Computing* 5, no. 6 (2001): 32-39. ftp.cs.wpi.edu/pub/techreports/01-07.ps.gz Cohen, Edith, Mayur Datar, Shinji Fujiwara, Aristides Gionis, Piotr Indyk, Rajeev Motwani, Jeffrey D. Ullman, and Cheng Yang. "Finding interesting associations without support pruning." *IEEE Transactions on Knowledge and Data Engineering* 13, no. 1 (2001): 64-78. www.stanford.edu/~datar/papers/icde00.ps Cohen, William W., and Wei Fan. "Web-collaborative filtering: Recommending music by crawling the web." *Computer Networks* 33, no. 1 (2000): 685-698. www.cs.columbia.edu/~wfan/papers/www9.ps.gz Collaborative Filtering cairo.aist-nara.ac.jp/~tomohi-f/Docs/cofil.ps.gz Condli, Michelle Keim, David D. Lewis, David Madigan, and Christian Posse. "Bayesian Mixed-E ects Models for Recommender Systems." In *ACM SIGIR*, vol. 99. 1999. www.stat.rutgers.edu/~madigan/PAPERS/collab.ps Cooley, Robert, Bamshad Mobasher, and Jaideep Srivastava. "Web mining: Information and pattern discovery on the world wide web." In *Tools with Artificial Intelligence, 1997. Proceedings., Ninth IEEE International Conference on*, pp. 558-567. IEEE, 1997. maya.cs.depaul.edu/~mobasher/papers/webminer-tai97.ps Cöster, Rickard, Andreas Gustaysson, Tomas Olsson, and Asa Rudstrom. "Enhancing web-based configuration with recommendations and cluster-based help." (2002). ectrl.itc.it/rpec/RPEC-Papers/04-coster.pdf Dai, Honghua Kathy, and Bamshad Mobasher. "Using ontologies to discover domain-level web usage profiles." *Semantic Web Mining* (2002): 35. maya.cs.depaul.edu/~mobasher/papers/swm02.pdf Dasgupta, Sanjoy, Wee Sun Lee, and Philip M. Long. "A theoretical analysis of query selection for collaborative filtering." *Machine Learning* 51, no. 3 (2003): 283-298. www.comp.nus.edu.sg/~leews/publications/colt01.pdf De Kroon, H. C. M. D., and E. J. H. Kerckhoffs. "Improving learning accuracy in information filtering." In *International Conference on Machine Learning-Workshop on Machine Learning Meets HCI (ICML-96.* 1996. www.ics.forth.gr/~moustaki/ICML96_HCI_ML/kroon.ps De Roure, David, Samhaa El-Beltagy, Steven Blackburn, and Wendy Hall. "A multiagent system for content based navigation of music." In Proceedings of the seventh ACM international conference on *Multimedia* (Part 2), pp. 63-66. ACM, 1999. www.bib.ecs.soton.ac.uk/data/4464/PDF/mascbnm.pdf De Vel, O., and S. Nesbitt. "A collaborative filtering agent system for dynamic virtual communities on the web." In *Working notes of Learning from Text and the Web, Conference on Automated Learning and Discovery CONALD*, vol. 98. 1998. www.cs.jcu.edu.au/~olivier/projects/web/conald98.ps Delgado, Joaquin, Naohiro Ishii, and Tomoki Ura. "Intelligent collaborative information retrieval." *Progress in Artificial Intelligence—IBERAMIA* 98 (1998): 465-465. www-ishii.ics.nitech.ac.jp/~jdelgado/iberamia98.ps.gz Dellarocas, Chrysanthos. "Immunizing online reputation reporting systems against unfair ratings and discriminatory behavior." In *Proceedings of the 2nd ACM conference on Electronic commerce*, pp. 150-157. ACM, 2000. ccs.mit.edu/dell/ec00reputation.pdf Dellarocas, Chrysanthos. "Mechanisms for coping with unfair ratings and discriminatory behavior in online reputation reporting systems." In *Proceedings of the twenty first international conference on Information systems*, pp. 520-525. Association for Information Systems, 2000. ccs.mit.edu/dell/icis2000.pdf Demiriz, Ayhan. "Enhancing product recommender systems on sparse binary data." *Data Mining and Knowledge Discovery* 9, no. 2 (2004): 147-170. www.rpi.edu/~demira/productrecommenderps.gz Distributing digital music over the internet—a chance for the.—Schulz (2000) www.ebs.de/Lehrstuehle/Wirtschaftsinformatik/Lehre/Seminar00/p_schulz.pdf Doe, John, Smith, Mary, "Maybe CHI", User Interface Research Center 380 Gui Lane Hillsville, N.Y. (2001) www.dcs.gla.ac.uk/equator/2001/09/workshop.pdf Dubosson-Torbay, Magali, Alexander Osterwalder, and Yves Pigneur. "E-business model design, classification, and measurements." *Thunderbird International Business Review* 44, no. 1 (2002): 5-23. inforge.unil.ch/yp/Pub/01-thunderbird.pdf Dwork, Cynthia, Ravi Kumar, Moni Naor, and D. Sivakumar. "Rank aggregation revisited." (2001): 613-622. www.cs.berkeley.edu/~christos/games/readings/rank.ps El-Beltagy, Samhaa, David DeRoure, and Wendy Hall. "The evolution of a practical agent-based recommender system." (2000). www.bib.ecs.soton.ac.uk/data/4495/postscript/rec4.ps Eriksson, Joakim, Niclas Finne, and Sverker Janson. "To each and everyone an agent: augmenting web-based commerce with agents." In *Proceedings of the International Workshop on Intelligent Agents on the Internet and Web, Fourth World Congress on Expert Systems*. 1998. www.sics.se/~sverker/public/papers/agentweb.pdf Fagrell, Henrik. "IntraNews: A News Recommending Service for Corporate Intranets." In *Proceedings of Computer Supported Cooperative Work in Design*, pp. 323-328. 1999. www.viktoria.informatik.gu.se/groups/mi3/results/papers/intranews.pdf Fano, Andrew E. "Shopper's eye: using location-based filtering for a shopping agent in the physical world." In *Proceedings of the second international conference on Autonomous agents*, pp. 416-421. ACM, 1998. www.ac.com/services/cstar/documents/a086fano.ps Fernández, Lourdes, J. Alfredo Sanchez, and Alberto Garcia. "Mibiblio: personal spaces in a digital library universe." In *Proceedings of the fifth ACM conference on Digital libraries*, pp. 232-233. ACM, 2000. ict.pue.udlap.mx/pubs/Mibiblio.ps.gz Ferrario, Maria-Angela, and Barry Smyth. "Collaborative Maintenance." In *Proceedings of the Irish Conference on Artificial Intelligence and Cognitive Science*. Cork, Ireland. 1999. www.cs.ucd.ie/pubs/1999/././staff/bsmyth/home/crc/aics99b.ps Fisher, D., K. Hildrum, J. Hong, M. Newman, and R. Vuduc. "SWAMI: a framework for collaborative filtering algorithm development and evaluation 1999." www.cs.berkeley.edu/~richie/swami/sigir00-final/report.ps Forsberg, Matas, Kristina Höök, and Martin Svensson. "Design principles for social navigation tools." In *Proceedings of the 4th ERCIM Workshop on 'User Interfaces for All', Special Theme 'Towards an Accessible Web'*, Stockholm. 1998. www.ics.forth.gr/proyat-hci/UI4ALL/UI4ALL-98/forsberg.pdf French, James C., and David B. Hauver. "Flycasting: On the Fly Broadcasting." In *DELOS workshop: Personalisation and recommender systems in digital libraries*. 2001. www.cs.virginia.edu/~cyberia/papers/flycast.pdf Friedman, Nir, and Moises Goldszmidt. *Learning Bayesian networks from data*. Morgan Kaufmann, 1999. www.cs.huji.ac.il/~nir/tutorial/readings.ps Funk, Peter, and Owen Conlan. "Case-Based Reasoning to Improve Adaptability of Intelligent Tutoring Systems." In *ECCBR Workshops*, pp. 15-24. 2002. www.mrtc.mdh.se/publications/0420.pdf Gandon, Fabien. "Engineering an ontology for a multi-agents corporate memory system." In *ISMICK 2001 Eighth International Symposium on the Management of Industrial and Corporate Knowledge*. 2001. www-sop.inria.fr/acacia/personnel/Fabien.Gandon/research/ismick2001/article_fabien_gandon_ismick2001.pdf /IJCAI2001/article_fabien_gandon_ijcai2001.ps Garcia, Octavio, Jesus Favela, Guillermo Licea, and Roberto Machorro. "Extending a collaborative architecture to support emotional awareness." CICESE, Mexico (1999). www.ai.mit.edu/people/jvelas/ebaa99/garcia-ebaa99.pdf Gayo Avello, Daniel, Dario Alvarez Gutierrez, and Juan Manuel Cueva Lovelle. "A concept-based retrieval tool: The cooperative Web." In *Proceedings of the IADIS International Conference on WWW/Internet*. IADIS, 2002. di002.edv.uniovi.eshdani/publications/gayoicwi02.pdf Getoor, Lise, and Mehran Sahami. "Using probabilistic relational models for collaborative filtering." In *Workshop on Web Usage Analysis and User Profiling (WEBKDD'99)*. 1999. viror.wiwi.uni-karlsruhe.de/webmining/bib/pdf/Getoor1999.pdf Getoor, Lise, Daphne Koller, and Nir Friedman. "From instances to classes in probabilistic relational models." In *Proceedings of the ICML Workshop on Attribute-Value and Relational Learning*. 2000. www.informatik.uni-freiburg.de/~ml/icm12000_workshop/getoorps Geyer-Schulz, Andreas, and Michael Hahsler. "Evaluation of recommender algorithms for an internet information broker based on simple association rules and on the repeat-buying theory." In *proceedings WEBKDD*, pp. 100-114. 2002. wwwai.wu-wien.ac.at/~hahsler/research/recomm_webkdd2002/final/webkdd2002.pdf Geyer-Schulz, Andreas, Michael Hahsler, and Maximillian Jahn. "A customer purchase incidence model applied to recommender services." In *International Workshop on Mining Web Log Data Across All Customers Touch Points*, pp. 25-47. Springer, Berlin, Heidelberg, 2001. wwwai.wu-wien.ac.at/~hahsler/research/recomm_webKDD2001/paper/geyerschulz.pdf Geyer-Schulz, Andreas, Michael Hahsler, and Maximillian Jahn. "Educational and scientific recommender systems: Designing the information channels of the virtual university." *International Journal of Engineering Education* 17, no. 2 (2001): 153-163. wwwai.wu-wien.ac.at/~hahsler/research/recomm_ijee2001/paper.pdf Ghani, Rayid, and Andrew Fano. "Building recommender systems using a knowledge base of product semantics." *Recommendation and Personalization in eCommerce* (2002): 40. ectrl.itc.it/rpec/RPEC-Papers/05-ghani.pdf Gionis, Aristides, Dimitrios Gunopulos, and Nick Koudas. "Efficient and tumble similar set retrieval." *ACM SIGMOD Record* 30, no. 2 (2001): 247-258. Stanford diglib.stanford.edu/~gionis/papers/sigmod01.ps Giudici, Paolo, and Robert Castelo. "Association models for web mining." *Data mining and knowledge discovery* 5, no. 3 (2001): 183-196. www.cs.uu.nl/~roberto/kddj2k1.pdf Glance, Natalie S., Antonietta Grasso, Uwe M. Borghoff, Dave Snowdon, and Jutta Willamowski. "Supporting collaborative information activities in networked communities." In *HCI* (2), pp. 422-426. 1999. inf2-www.informatik.unibw-muenchen.de/People/borghoff/pspapers/hci99.ps Glance, Natalie, Damián Arregui, and Jean-Luc Meunier. "Collaborative document monitoring via a recommender system." In *Proceedings of International Workshop on Agent-Based Recommender Systems, Fourth International Conference on Autonomous Agents.* Barcelona, Spain, 2000. www.xrce.xerox.com/research/ct/publications/Documents/P87437/content/kpma-wars.pdf Glance, Natalie, Damián Arregui, and Manfred Dardenne. "Knowledge pump: Community-centered collaborative filtering." Xerox Research Centre Europe, Grenoble Laboratory (1997): 1-5. www.ercim.org/publication/ws-proceedings/DELOS5/arregui.ps.gz Godbole, Shantanu. "Document Classification as an Internet service: Choosing the best classifier." *School of Information Technology, Bombay*, September, www.it.iitb.ac.in/~shantanu/work/mtpsg.pdf (2001). www.it.iitb.ac.in/~shantanu/work/mtpsg.pdf Goker, M., and Cynthia Thompson. "The adaptive place advisor: A conversational recommendation system." In *Proceedings of the 8th German Workshop on Case Based Reasoning*, Lammerbuckel, Germany, pp. 187-198. 2000. www.cs.utah.edu/~cindi/papers/gwcbr.ps.gz Gokhale, Anuja, and Mark Claypool. "Correlation thresholds for more accurate collaborative filtering." (1999). ftp.cs.wpi.edu/pub/techreports/99-17.ps.gz Gokhale, Anuja. "Improvements to collaborative filtering algorithms." Master's thesis, Worcester Polytechnic Institute., 1999. www.cs.wpi.eduhclaypool/ms/cf-improve/cf-improve.ps Good, N., Schafer, J. B., Konstan, J., Borchers, A., Sarwar, B., Herlocker, J., and Riedl, J., Combining Collaborative Filtering with Personal Agents for Better Recommendations. Proceedings of the 1999 Conference of the American Association of Artifical Intelligence (AAAI-99). pp 439-446, www.cs.umn.edu/Research/GroupLens/papers/pdf/aaai-99.pdf Graef, Guntram, and Christian Schaefer. "Application of art2 networks and self-organizing maps to collaborative filtering." In *Workshop on Adaptive Hypermedia*, pp. 296-309. Springer, Berlin, Heidelberg, 2001. wwwis.win.tue.nl/ah2001/papers/graef-schaefer-1.pdf Graef, Guntram, and Martin Gaedke. "Construction of adaptive web-applications from reusable components." In *International Conference on Electronic Commerce and Web Technologies*, pp. 1-13. Springer, Berlin, Heidelberg, 2000. www.teco.edu/~graef/paper/ecweb-graef-gaedke-sv2.pdf Graef, Guntram, and Martin Gaedke. "Self-Adaptive Web-Applications." *Poster-Proceedings of the 8th International World Wide Web Conference*. 2000. www.teco.edu/~gaedke/paper/2000-www9-poster.pdf Grasso, Antonietta, Michael Koch, and Alessandro Rancati. "Augmenting recommender systems by embedding interfaces into practices." In *Proceedings of the international ACM SIGGROUP conference on Supporting group work*, pp. 267-275. ACM, 1999. www.xrce.xerox.com/research/ct/publications/Documents/P10226/content/HICSS-33.ps Grasso, Antonietta, Michael Koch, and Dave Snowdon. "Campiello—New user interface approaches for community networks." *ACM SIGGROUP Bulletin* 20, no. 2 (1999): 15-17. www11.informatik.tu-muenchen.de/publications/pdf/Grasso1998a.pdf Grasso, M. Antonietta, Uwe M. Borghoff, Natalie Glance, and Jutta Willamowski. "Collaborative information gathering." In *2nd International Conference EuroMedia/WEBTEC*, pp. 65-72. 1998. inf2-www.informatik.unibw-muenchen.de/People/borghoff/pspapers/euromedia98b.ps Green, Shaw, Pádraig Cunningham, and Fergal Somers. "Agent mediated collaborative web page filtering." *Cooperative Information Agents II Learning, Mobility and Electronic Commerce for Information Discovery on the Internet* (1998): 195-205. www.cs.tcd.ie/research_groups/aig/iag/cia.ps Griffith, Josephine, and Colm O'Riordan. "Collaborative filtering." (2000). www.it.nuigalwayie/TR/./rep00/NUIG-IT-160900.ps.gz Groves, Sacha, and Judy Kay. "Foundations for building a digital sister-in-law: explicitly building scrutable user models from critical reviews." www.ted.cmis.csiro.au/adcs01/012_Groves.pdf Gunnarsson, Maj, Tomas Lindroth, Maria Magnusson, P. Rasmusson, and Ulrika Snis. "Less is more: When IT comes to knowledge management." In *Proceedings of IRIS*, vol. 23. 2000. iris23.htu.se/proceedings/PDF/110final.PDF Guo, Hui, Thomas Kreifelts, and Angi Voss. "Soap: Social filtering through social agents." *ECRIM Workshop Proceedings No. 98/W001 of the 5 th DELOS Workshop on Filtering and Collaborative Filtering. The European Research Consortium for Inormatics and Mathematics*. 1997. www.ercim.org/publication/ws-proceedings/DELOS5/guo.ps.gz Guo, Hui. "Soap: Live recommendations through social agents." In *Fifth DELOS Workshop on Filtering and Collaborative Filtering*, Budapest. 1997. www.sztaki.hu/conferences/delosbudapest/papers/guo.ps Gupta, J E Moreira S P Midkiff M., and R. Lawrence. "Parallel Data Mining using the Array Package for Java." www.research.ibm.com/people/g/gupta/sc99.ps Ha, Vu Anh. "Reasoning with partial preference models." PhD diss., University of Wisconsin, Milwaukee, 2001. cs.uwm.edu/~vu/papers/proposal.pdf Ha, Vu, Peter Haddawy, and John Miyamoto. "Similarity measures on preference structures, part ii: utility functions." In *Proceedings of the Seventeenth conference on Uncertainty in artificial intelligence*, pp. 186-193. Morgan Kaufmann Publishers Inc., 2001. www.cs.uwm.edu/~vu/papers/uai01.ps.gz Hahn, Jungpil, and Mani R. Subramani. "A framework of knowledge management systems: issues and challenges for theory and practice." In *Proceedings of the twenty first international conference on Information systems*, pp. 302-312. Association for Information Systems, 2000. www.a-kindofmagic.com/~jhahn/./papers/hs_icis2000.pdf Hall, Robert J. "A countermeasure to duplicate-detecting anti-spam techniques." *Unknown Month, AT&T Labs Technical Report* 99, no. 1 (1999). www.research.att.com/resources/trs/./TRs/99/99.9/99.9.1.body.ps Han, Eui-Hong, Daniel Boley, Maria Gini, Robert Gross, Kyle Hastings, George Karypis, Vipin Kumar, Bamshad Mobasher, and Jerome Moore. "Webace: a web agent for document categorization and exploration." In *Proceedings of the second international conference on Autonomous agents*, pp. 408-415. ACM, 1998. www-users.cs.umn.edu/~gross/papers/agents98.ps Hauver, David B., and James C. French. "Flycasting: using collaborative filtering to generate a playlist for online radio." In *Web Delivering of Music*, 2001. *Proceedings. First International Conference on*, pp. 123-130. IEEE, 2001. www.cs.virginia.edu/~cyberia/papers/wedelmusic.ps Haveliwala, Taher, Aristides Gionis, and Piotr Indyk. "Scalable techniques for clustering the web." (2000). www.research.att.com/conf/webdb2000/PAPERS/8c.ps Hayes, Conor, and Padraig Cunningham. *An on-line evaluation framework for recommender systems*. Trinity College Dublin, Dept. Computer Science, 2002. ectrl.itc.it/rpec/RPEC-Papers/06-hayes.pdf Hayes, Conor, and Padraig Cunningham. *Smart Radio-a proposal*. Trinity College Dublin, Department of Computer Science, 1999. ftp.cs.tcd.ie/pub/tech-reports/reports.99/TCD-CS-1999-24.pdf Hayes, Conor, Padraig Cunningham, and Barry Smyth. "A case-based reasoning view of automated collaborative filtering." *Case-Based Reasoning Research and Development* (2001): 234-248. ftp.cs.tcd.ie/pub/tech-reports/reports.01/TCD-CS-2001-09.pdf Heckerman, David, David Maxwell Chickering, Christopher Meek, Robert Rounthwaite, and Carl Kadie. "Dependency networks for inference, collaborative filtering, and data visualization." *Journal of Machine Learning Research* 1, no. October (2000): 49-75. www.ai.mit.edu/projects/jmlr/papers/volume1/heckerman00a/heckerman00a.ps.gz www.cs.brown.edu/people/amygreen/seminar/dependency.pdf Heer, Jeffrey, and Ed H. Chi. "Identification of web user traffic composition using multi-modal clustering and information scent." *Proc. Workshop on Web Mining, SIAM Conference on Data Mining*, pp. 51-58. 2001. www-users.cs.umn.eduhechi/papers/SIAM-data-mining-2001/SIAM-Data-Mining-MMC2.pdf Herlocker, J., Konstan, J., and Riedl, J., Explaining Collaborative Filtering Recommendations. In proceedings of ACM 2000 Conference on Computer Supported Cooperative Work, Dec. 2-6, 2000, pp. 241-250. www.cs.umn.edu/Research/GroupLens/papers/pdf/explain-CSCW.pdf Herlocker, Jonathan L., Joseph A. Konstan, Al Borchers, and John Riedl. "An algorithmic framework for performing collaborative filtering." In *Proceedings of the 22nd annual international ACM SIGIR conference on Research and development in information retrieval*, pp. 230-237. ACM, 1999. www.cs.umn.edu/Research/GroupLens/papers/pdf/algs.pdf Hill, William C., and Loren G. Terveen. "Involving remote users in continuous design of web content." In *Proceedings of the 2nd conference on Designing interactive systems: processes, practices, methods, and techniques*, pp. 137-145. ACM, 1997. www.research.att.comhterveen/dis97.ps Hird, Shane. "Technical solutions for controlling spam." proceedings of AUUG2002 (2002). Distributed security.dstc.edu.au/papers/technical_spam.ps Hoenkamp, E., L. Schomaker, P. Van Bommel, C. H. A. Koster, and Th P. Van Der Weide. "Profile-a proactive information filter." (1996). ftp.cs.kun.nl/pub/SoftwEng.InfSyst/articles/Filterinit.ps.Z Hoffmann, Marcel, Kai-Uwe Loser, Thomas Walter, and Thomas Herrmann. "A design process for embedding knowledge management in everyday work." In *Proceedings of the international ACM SIGGROUP conference on Supporting group work*, pp. 296-305. ACM, 1999. iundg.informatik.uni-dortmund.de/Daten/pubs/HoffLosWalHerr_Group99.pdf Hofmann, Thomas, and D. Hartmann. "Collaborative filtering with privacy via factor analysis." In Proceedings of the 2005 ACM symposium on applied computing, pp. 791-795. 2005. www.cs.berkeley.edu/~jfc/papers/02/SIGIR02.pdf Hofmann, Thomas. "Collaborative filtering via gaussian probabilistic latent semantic analysis." *Proc. 26th annual international ACM SIGIR conference on Research and development in informaion retrieval*, pp. 259-266. ACM, 2003. www.cs.brown.edu/people/th/papers/HofmannPuzicha-IJCAI99.pdf Höök, Kristina, Jarmo Laaksolahti, Martin Svensson, and Annika Waern. "Designing for social navigation of food recipes." *Lecture notes in computer science* (2000): 331-334. www.sics.se/~martins/publications/hook.pdf Höök, Kristina, Jarmo Laaksolahti, Martin Svensson, and Annika Waern. "Individual differences in social navigation." (2000). www.sics.se/~martins/publications/chi00_efol.pdf Huang, Lan. "A survey on web information retrieval technologies." *Computer Science Department*, State University of New York at Stony Brook, N.Y. (2000): 11794-4400. ranger.uta.edu/~alp/ix/readings/SurveyOfWebSearchEngines.pdf Hughes, Sinead, and Colm O'Riordan. *Collaborative Filtering as means to reduce information overload*. Tech. report, Dept, of IT, NUI, Galway, Ireland, http://citeseer.ist.psu.edu/494054.html.81. www.it.nuigalway.ie/TR/abstracts/./papers/sh.ps.gz Instone, Keith. "Information architecture and personalization: An information architecture-based framework for personalization systems." *Argus Centre for Information Architecture* (2000): 1-12. www.zurich.ibm.com/~mrs/chi2000/contributions/instone.pdf Iyer, Raj Dharmarajan. "An efficient boosting algorithm for combining preferences." PhD diss., Massachusetts Institute of Technology, 1999. www.Ics.mit.edu/publications/pubs/pdf/MIT-LCS-TR-811.pdf Jacobs, David W., Daphna Weinshall, and Yoram Gdalyahu. "Condensing image databases when retrieval is based on non-metric distances." In *Computer Vision, 1998. Sixth International Conference on*, pp. 596-601. IEEE, 1998. cs.nyu.edu/cs/faculty/weinshal/papers/nonmetric-ret.ps.gz Jacobs, David, Daphna Weinshall, and Yoram Gdalyahu. "Class representation and image retrieval with non-metric distances." *IEEE Trans. Pattern Anal. Mach. Intell* 22, no. 6 (2000): 583-600. www.neci.nj.nec.com/homepages/dwj/non-metric.ps Jameson A (2001). Systems that adapt to their users. Description of an IJCAI 01 tutorial on user-adaptive systems. Last update: 7 Mar. 2001. At www.dfki.de/~jameson/ijcai01-tutorial-jameson.pdf, accessed 12 Dec. 2002; www.cs.uni-sb.de/users/jameson/ijcai01-tutorial-jameson.pdf Jameson, Anthony. "Designing User-Adaptive Systems." Tutorial presented at IUI, Santa Fe, New Mexico, 2001. www.cs.uni-sb.de/users/jameson/iui01-tutorial-jameson.pdf Jeh, Glen, and Jennifer Widom. "SimRank: a measure of structural-context similarity." In *Proceedings of the eighth ACM SIGKDD international conference on Knowledge discovery and data mining*, pp. 538-543. ACM, 2002. www-cs-students.stanford.edu/~glenj/simrank.ps Joachims, Thorsten, Tom Mitchell, Dayne Freitag, and Robert Armstrong. *Webwatcher. Machine learning and hypertext*. CARNEGIE-MELLON UNIV PITTSBURGH Pa.

SCHOOL OF COMPUTER SCIENCE, 1995. mobile.c-sie.ntu.edu.tw/~yjhsu/courses/u1760/papers/webwatcher.ps.gz Joerding, Tanja. "Temporary user modeling for adaptive product presentations in the Web." In *UM99 User Modeling*, pp. 333-334. Springer, Vienna, 1999. www.cs.usask.ca/UM99/Proc/DC/joerding.pdf John, George H. "Behind-the-scenes data mining: a report on the KDD-98 panel." *ACM SIGKDD Explorations Newsletter* 1, no. 1 (1999): 6-8. diagnosis.xjtu.edu.cn/kdd/john.ps June Tha Tereen (2000) fas.sfu.ca/pub/cs/theses/2000/SonnyHanMengCheeMSc.pdf Jung, Sung Young, Jeong-Hee Hong, and Taek-Soo Kim. "A formal model for user preference." In *Data Mining, 2002. ICDM 2003.*, pp. 235-242. IEEE, 2002. mobigen.com/~chopin/research/publish/ICDM2002/syjung_IEEE_ICDM2002_A_Formal_Model_for_Preference.ps Kahabka, Thomas, Mari Korkea-aho, and Günther Specht. "GRAS: An Adaptive Personalization Scheme for Hypermedia Databases." In *HIM*, pp. 279-292. 1997. www3.informatik.tu-muenchen.de/public/mitarbeiter/specht/lit/97-HIM-gras.ps Kanawati, Rushed, and Maria Malek. "Informing the design of shared bookmark systems." In *Content-Based Multimedia Information Access-Volume* 1, pp. 170-179. Le Centre De Hautes Etudes Internationales D'informatique Documentaire, 2000. 133.23.229.11/~ysuzuki/Proceedingsall/RIAO2000/Wednesday/15AP1.pdf Karypis, George. "Evaluation of item-based top-n recommendation algorithms." In *Proceedings of the tenth international conference on Information and knowledge management*, pp. 247-254. ACM, 2001. www-users.itlabs.umn.edu/~karypis/publications/Papers/Postscript/itemrs.ps Kautz, Henry, Bart Selman, and Mehul Shah. "Referral Web: combining social networks and collaborative filtering." *Communications of the ACM* 40, no. 3 (1997): 63-65. akpublic.research.att.com/~kautz/papers-ftp/refweb-CACM.ps Kilander, Fredrik, Eva Fahraeus, and Jacob Palme. "Intelligent Information Filtering. The IntFilter Project" *Technical report* (1997)., Dept. of Computer and Systems Science, Stockholm University, Feb. 17, 1997." (1997). www.dsv.su.se/~fk/if_Doc/juni96/ifrpt.ps.Z Kilander, Fredrik, Eva Fahraeus, and Jacob Palme. "PEFNA—The Private Filtering News Agent." (1997). www.dsv.su.se/~fk/if_Doc/Pefna/pefna.ps.Z Kilander, Fredrik. "A brief comparison of news filtering software." *Unpublished paper* (1995). www.cs.kun.nl/is/research/filter/literature/Comparison.ps Kleinberg, Jon, Christos H. Papadimitriou, and Prabhakar Raghavan. "On the value of private information." In *Proceedings of the 8th conference on Theoretical aspects of rationality and knowledge*, pp. 249-257. Morgan Kaufmann Publishers Inc., 2001. www.eecs.Berkeley.edu/~christos/tark.ps Knowledge-based Recommender Systems. To appear in the Encyclopedia of Library and Information Science, www.ics.uci.eduhburke/research/papers/kb-recommender-reprint.ps.gz; /burke-elis-00.pdf.gz Koch, Michael, and Martin S. Lacher. "Integrating community services-a common infrastructure proposal." In *Knowledge-Based Intelligent Engineering Systems and Allied Technologies, 2000. Proceedings. Fourth International Conference on*, vol. 1, pp. 56-59. IEEE, 2000. www11.in.tum.de/publications/pdf/Koch2000.pdf Koch, Michael, and Petra Schubert. "Personalization and community communication for customer support." In *Proc. 6th Intl. Conf. on Work With Display Units-World Wide Work* (WWDU2002), pp. 530-532. Berchtesgaden, Germany, 2002. www11.in.tum.de/publications/pdf/Koch2002.pdf Kohrs, Arnd, and Bernard Merialdo. "Improving collaborative filtering with multimedia indexing techniques to create user-adapting web sites." In *Proceedings of the seventh ACM international conference on Multimedia (Part 1)*, pp. 27-36. ACM, 1999. www.eurecom.fr/~kohrs/publish/ACMMM99.ps.gz Kohrs, Arnd, and Bernard Merialdo. "Using category-based collaborative filtering in the Active WebMuseum." In *Multimedia and Expo, 2000. ICME 2000. 2000 IEEE International Conference on*, vol. 1, pp. 351-354. IEEE, 2000. www.eurecom.fr/~kohrs/publish/ICME2000.ps.gz Kohrs, Arnd, and Bernard Merialdo. "Using color and texture indexing to improve collaborative filtering of art paintings." In *Proc. of European Workshop on CBMI*, vol. 99. 1999. www.eurecom.fr/~kohrs/publish/CBMI99.ps.gz Konstan, Joseph A., Bradley N. Miller, David Maltz, Jonathan L. Herlocker, Lee R. Gordon, and John Riedl. "GroupLens: applying collaborative filtering to Usenet news." *Communications of the ACM* 40, no. 3 (1997): 77-87. www.ics.uci.edu/~pratt/courses/papers/p77-konstan.pdf Koychev, Ivan. "Learning about user in the presence of hidden context." *Proc. UM2001 Workshop on Machine Learning for User Modeling*, pp. 49-58. 2001. www.d-fki.de/~rafer/um01-ml4 um-ws/papers/IK.pdf Kramer, Joshua David. "Agent based personalized information retrieval." PhD diss., Massachusetts Institute of Technology, 1997. grebe.lcs.mit.edu/papers/kramer-thesis.ps.gz Kruschwitz, Udo. "A rapidly acquired domain model derived from markup structure." In *Proceedings of the ESSLLI'01 Workshop on Semantic Knowledge Acquisition and Categorisation*. 2001. cswww.essex.ac.uk/staff/udo/papers/esslli.ps.gz Kumar, Ravi, Prabhakar Raghavan, Sridhar Rajagopalan, and Andrew Tomkins. "Recommendation systems: A probabilistic analysis." In *Foundations of Computer Science, 1998. Proceedings. 39th Annual Symposium on*, pp. 664-673. IEEE, 1998. www.almaden.ibm.com/cs/k53/./algopapers/focs98rec.ps Kurapati, Kaushal, Srinivas Gutta, David Schaffer, Jacquelyn Martino, and John Zimmerman. "A multi-agent TV recommender." In *Proceedings of the UM 2001 workshop "Personalization in Future TV.* 2001. www.cs.umbc.edu/~skaush1/um_2001.pdf Kurhila, Jaakko, Miikka Miettinen, Petri Nokelainen, and Henry Tirri. "Dynamic profiling in a real-time collaborative learning environment." In *International Conference on Intelligent Tutoring Systems*, pp. 239-248. Springer, Berlin, Heidelberg, 2002. cosco.hiit.fi/edutech/publications/its2002.pdf Kushmerick, Nicholas. "Robustness analyses of instance-based collaborative recommendation." *Lecture notes in computer science* (2002): 232-244. www.cs.ucd.ie/staff/nick/home/research/download/kushmerick-ecml2002.pdf Lacher, Martin S., Michael Koch, and Wolfgang Worndl. "A framework for personalizable community Web portals." In *Proceedings of the Human-Computer Interaction International Conference*, vol. 2, pp. 785-9. 2001. www11.in.tum.de/publications/pdf/lacher2001a.pdf Lagha, S. Ben, Alexander Osterwalder, and Yves Pigneur. "Modeling e-Business with eBML." In *5th Intl Workshop on the Management of Firms' Networks* (CIMRE'01), Mandia, Tunisia. 2001. inforge.unil.ch/yp/Pub/01-cimre.pdf Lang, Ken. "NewsWeeder: Learning to Filter Netnews" *School of Computer Science Carnegie Mellon University 5000 (1995)*." In *Proceedings of the 12th international conference on machine learning*, vol. 10, pp. 331-339. 1995. www.fi.muni.cz/usr/popelinsky/newsweeder.ps.gz Langley, Pat, and Michael Fehling. "The experimental study of adaptive user interfaces." *Institute for the Study of Learning and Expertise* (1998). www.isle.org/~langley/papers/adapt.exper.ps.gz Lashkari, Yezdezard Zerxes. "Feature guided automated collaborative filtering." PhD diss., Massachusetts Institute of Technology, 1995. ftp.media.mit.edu/pub/yezdi/proposal.ps Lau, Raymond, Arthur H M ter Hofstede, and Peter D. Bruza. "A logic-based approach for adaptive information filtering agents." In *Pacific Rim International Conference on Artificial Intelligence*, pp. 269-278. Springer, Berlin, Heidelberg, 2000. www.icis.qut.edu.au/~arthur/articles/iia.ps.Z Lee, Wee Sun. "Collaborative learning for recommender systems." In *ICML*, vol. 1, pp. 314-321. 2001. www.comp.nus.edu.sg/~leews/publications/icm101.ps Lee, Wee Sun. "Online clustering for collaborative filtering." (2000). hal.comp.nus.edu.sg/recommender/Papers/online/online.ps.gz Levene, Mark, and Alexandra Poulovassilis. "Web dynamics." *Software Focus* 2, no. 2 (2001): 60-67. www.dcs.bbk.ac.uk/~mark/download/web_focus_final.pdf Levy, Alon Y., and Daniel S. Weld. "Intelligent internet systems." *Artificial Intelligence* 118, no. 1-2 (2000): 1-14. www.cs.auc.dk/research/DSS/papers/levyweld00.pdf Lifantsev, Maxim. "A System for Collaborative Web Resource Categorization and Ranking." In *Ph. D. Dissertation Proposal*, October 2001. Available at Researchindex (Citeseer): citeseer.nj.nec. com/496245.html. 2001. www.ecsl.cs.sunysb.edu/~maxim/cgi-bin/Get/SCWR-CR.ps.gz Loon, Tong Sau, and Vaduvur Bharghavan. "Alleviating the Latency and Bandwidth Problems in WWW Browsing." In *USENIX Symposium on Internet Technologies and Systems*, pp. 219-230. 1997. bbcr.uwaterloo.ca/~brecht/courses/756/readings/prefetching/alleviating-USITS97.ps Lueg, Christopher, and Christoph Landolt. "A Java-based approach to active collaborative filtering." In *CHI 98 Conference Summary on Human Factors in Computing Systems*, pp. 319-320. ACM, 1998. ftp.ifrunizh.ch/pub/institute/ailab/papers/lueg/chi98_late.ps.Z Lueg, Christopher. "An adaptive Usenet interface supporting situated actions." In *Proceedings of the 3rd ERCIM Workshop on User Interfaces for All*, pp. 165-170. 1997. ftp.ifi.unizh.ch/pub/institute/ailab/papers/lueg/ercim97.ps.gz Lueg, Christopher. "Getting to Know Each Other on the Web: Using Web Server Access Logs to Enhance Community." (2000). www-staff.it.uts.edu.au/~lueg/papers/www2001.ps.gz ftp.ifi.unizh.ch/pub/institute/ailab/papers/lueg/aus2000.ps Lueg, Christopher. "Social filtering and social reality." In *Proceedings of the 5th DELOS Workshop on Filtering and Collaborative Filtering*. 1997. ftp.ifi.unizh.ch/pub/institute/ailab/papers/lueg/delos97.ps.gz Lueg, Christopher. "Supporting situated actions in high volume conversational data situations." In *Proceedings of the SIGCHI Conference on Human Factors in Computing Systems*, pp. 472-479. ACM Press/Addison-Wesley Publishing Co., 1998. ftp.ifi.unizh.ch/pub/institute/ailab/papers/lueg/chi98.ps.gz Maes, Pattie, Robert H. Guttman, and Alexandros G. Moukas. "Agents that buy and sell." *Communications of the ACM* 42, no. 3 (1999): 81-ff. www.cis.upenn.edu/~lee/00cis640/papers/maes.pdf Malek, Maria, and Rushed Kanawati. "A cooperating hybrid Neural-CBR classifiers for building on-line communities." In *The international conference on Case-Based Reasoning* (ICCBR'01). 2009. www.aic.nrl.navy.mil/papers/2001/AIC-01-003/ws5/ws5toc8.PDF Maltz, D., Distributing Information for Collaborative Filtering on Usenet Net. MIT Master's Thesis, (1994) www.cs.cmu.edu/afs/cs.cmu.edu/user/dmaltz/Doc/mit-thesis.ps.gz; docplayer.net/22076891-Author-distributing-information-for-collaborative-filtering-on-usenet-netnews.html Manco, Giuseppe, Elio Masciari, Massimo Ruffolo, and Andrea Tagarelli. "Towards an adaptive mail classifier." In *Proc. of Italian Association for Artificial Intelligence Workshop*. 2002. www-dii.ing.unisi.it/aiia2002/paper/APAUT/manco-aiia02.pdf Maneeroj, Saranya, Hideaki Kanai, and Katsuya Hakozaki. "Combining Dynamic Agents and Collaborative Filtering without Sparsity Rating Problem for Better Recommendation Quality." In DELOS *Workshop: Personalisation and Recommender Systems in Digital Libraries*. 2001. www.ercim.org/publication/ws-proceedings/DelNoe02/Saranya.pdf Mao, Runying. "Adaptive-FP: an efficient and effective method for multi-level multi-dimensional frequent pattern mining." PhD diss., Simon Fraser University, 2001. fas.sfu.ca/pub/cs/theses/2001/RunyingMaoMSc.ps.gz Masterton, Simon. "The Virtual Participant: Lessons to be Learned from a Case-based Tutor's assistant." In *Proceedings of the 2nd international conference on Computer support for collaborative learning*, pp. 186-196. International Society of the Learning Sciences, 1997. kmi.open.ac.uk/techreports/papers/kmi-tr-47.ps.gz McDonald, David W. "Recommending expertise in an organizational setting." In *CHI'99 Extended Abstracts on Human Factors in Computing Systems*, pp. 63-64. ACM, 1999. www.ics.uci.edu/~dmcdonal/papers/chi99.final.pdf McDonald, David W., and Mark S. Ackerman. "Expertise recommender: a flexible recommendation system and architecture." In *Proceedings of the 2000 ACM conference on Computer supported cooperative work*, pp. 231-240. ACM, 2000. www.ics.uci.eduhackerman/pub/00b30/cscw00.er.pdf McDonald, David W., and Mark S. Ackerman. "Just talk to me: a field study of expertise location." In *Proceedings of the 1998 ACM conference on Computer supported cooperative work*, pp. 315-324. ACM, 1998. www.ics.uci.edu/~dmcdonal/papers/cscw98.final.pdf Melville, Prem, Raymond J. Mooney, and Ramadass Nagarajan. "Content-boosted collaborative filtering for improved recommendations." In *Aaai/iaai*, pp. 187-192. 2002. www.cs.utexas.edu/users/ml/papers/cbcf-aaai-02.ps.gz Melville, Prem, Raymond J. Mooney, and Ramadass Nagarajan. "Content-boosted collaborative filtering." (2001). www.cs.utexas.edu/users/ml/papers/cbcf-sigir-wkshp-01.ps.gz Menczer, Filippo, W. Nick Street, Narayan Vishwakarma, Alvaro E. Monge, and Markus Jakobsson. "IntelliShopper: A proactive, personal, private shopping assistant." In *Proceedings of the first international joint conference on Autonomous agents and multiagent systems: part 3*, pp. 1001-1008. ACM, 2002. dollarbiz.uiowa.edu/~fil/Papers/intellishopper.pdf Merialdo, Arnd Kohrs-Bernard. "Clustering for collaborative filtering applications." *Intelligent Image Processing, Data Analysis & Information Retrieval* 3 (1999): 199. www.eurecom.fr/~kohrs/publish/CIMCA99.ps.gz Middleton, Stuart E., David C. De Roure, and Nigel R. Shadbolt. "Capturing knowledge of user preferences: ontologies in recommender systems." In *Proceedings of the 1st international conference on Knowledge capture*, pp. 100-107. ACM, 2001. www.ecs.soton.ac.uk/~sem99r/kcap-paper.pdf Middleton, Stuart E., Harith Alani, Nigel R. Shadbolt, and David C. De Roure. "Exploiting synergy between ontologies and recommender systems." In *Proceedings of the 3rd International Conference on Semantic Web-Volume 55*, pp. 41-50. CEUR-WS. org, 2002. www.ecs.soton.ac.uk/~sem99r/www-paper.ps Miller, B., Riedl, J., and Konstan, J. Experiences with GroupLens: Making Usenet useful again. Proceedings of the 1997 Usenix Winter Technical Conference. January 1997. www.cs.umn.edu/Research/GroupLens/papers/pdf/usenix97.pdf Miyahara, Koji, and Michael J. Pazzani. "Collaborative filtering with the simple Bayesian classifier." In *Pacific Rim International conference on artificial intelligence*, pp. 679-689. Springer, Berlin, Heidelberg, 2000. www.ics.uci.edu/~pazzani/Publications/koji.pdf Mladenic, Dunja. "Machine Learning on non-homogeneous, distributed text data." *Computer Science*, University of Ljubljana, Slovenia (1998). www.cs.cmu.edu/afs/cs/project/theo-4/text-learning/wvvw/pwww/papers/PhD/PhDBib.ps.gz Mobasher, Bamshad, Honghua Dai, Tao Luo, and Miki Nakagawa. "Effective personalization based on association rule discovery from web usage data." In *Proceedings of the 3rd international workshop on Web information and data management*, pp. 9-15. ACM, 2001. maya.cs.depaul.edu/~mobasher/papers/widm01.pdf Mobasher, Bamshad, Honghua Dai, Tao Luo, and Miki Nakagawa. "Improving the effectiveness of collaborative filtering on anonymous web usage data." In *Proceedings of the IJCAI 2001 Workshop on Intelligent Techniques for Web Personalization* (ITWP01), pp. 53-61. 2001. www.mineit.com/lc/ijcai/papers/mobasher.pdf Mobasher, Bamshad, Honghua Dai, Tao Luo, Yuqing Sun, and Jiang Zhu. "Integrating web usage and content mining for more effective personalization." *Electronic commerce and web technologies* (2000): 165-176. maya.cs.depaul.edu/~mobasher/papers/ecweb2000.ps Mobasher, Bamshad, Robert Cooley, and Jaideep Srivastava. "Automatic personalization based on web usage mining." *Communications of the ACM* 43, no. 8 (2000): 142-151. maya.cs.depaul.edu/~mobasher/personalization/personalization.ps Mobasher, M. and Dai, H., 2000. Luo., T., Nakagawa, M., and Witshire, J.,"Discovery of aggregate usage profiles for Web personalization,". In *WebKDD Workshop*, Boston, USA. maya.cs.depaul.edu/~mobasher/papers/webkdd2000.pdf Mock, Kenrick J. "Hybrid hill-climbing and knowledge-based techniques for intelligent news filtering." In *Proceedings of the national conference on artificial intelligence* (AAAI'96), pp. 48-53. 1996. www.cs.pdx.edu/~kenrick/papers/infoproc.ps.gz Montaner, Miguel, Beatriz Lopez, and Josep Lluis de la Rosa. "Developing trust in recommender agents." In *Proceedings of the first international joint conference on Autonomous agents and multiagent systems*: part 1, pp. 304-305. ACM, 2002. eia.udg.es/~mmontane/montaner-aamas02.pdf Mooney, Raymond J., and Loriene Roy. "Content-based book recommending using learning for text categorization." In *Proceedings of the fifth ACM conference on Digital libraries*, pp. 195-204. ACM, 2000. ftp.cs.utexas.edu/pub/mooney/papers/libra-dl-00.ps.gz Mooney, Raymond J., Paul N. Bennett, and Loriene Roy. "Book recommending using text categorization with extracted information." In *Proc. Recommender Systems Papers from 1998 Workshop, Technical Report WS-98-08*. 1998. ftp.cs.utexas.edu/pub/mooney/papers/libra-textcat98.ps.gz Moreira, Jose, Sam Midkiff, Manish Gupta, and Rick Lawrence. "High performance computing with the array package for Java: A case study using data mining." In *Supercomputing, ACM/IEEE 1999 Conference*, pp. 10-10. IEEE, 1999. www.sc99.org/proceedings/papers/moreira1.pdf Morgan, J., and A. Kilgour. "Personalising on-line information retrieval support with a genetic algorithm." (1996). www.cee.hw.ac.uk/~jeff/files/changing.ps.Z Waern, Annika, Charlotte Averman, Mark Tierney, and Åsa Rudström. "Information services based on user profile communication." In *UM99 User Modeling*, pp. 319-321. Springer, Vienna, 1999. www.sics.se/~annika/papers/UM99.ps Mui, Lik, Mojdeh Mohtashemi, Cheewee Ang, Peter Szolovits, and Ari Halberstadt. "Ratings in distributed systems: A bayesian approach." In *Proceedings of the Workshop on Information Technologies and Systems* (WITS), pp. 1-7. 2001. www.lcs.mit.edu/publications/pubs/pdf/MIT-LCS-TM-617.pdf Mukherjee, Rajatish, P. Dutta, Sandip Sen, and Ip Sen. "MOVIES2GO—A new approach to online movie recommendation." In *Proceedings of the IJCAI Workshop on intelligent Techniques for Web Personalization*. 2001. www.mineit.com/lc/ijcai/papers/mukherjee.pdf Murthy, K. R. K., S. S. Keerthi, and M. N. Murty. "Networked Distributed Collaboration for Information Activity Infrastructure." In *Knowledge Based Computer Systems: Proceedings of the International Conference: KBCS—2000*, p. 107. Allied Publishers, 2000. bheeshma.csa.iisc.ernet.in/~krish/docs/NDC.ps.gz Nguyen, Hien, and Peter Haddawy. "The decision-theoretic interactive video advisor." In *Proceedings of the Fifteenth conference on Uncertainty in artificial intelligence*, pp. 494-501. Morgan Kaufmann Publishers Inc., 1999. www.cs.uwm.edu/faculty/haddawy/pubs/hien-aaai98wkshp.ps.Z Nichols, D. M. 1998. Implicit rating and filtering. In Proceedings of the 5th DELOS Workshop. www.ercim.org/publication/ws-proceedings/DELOS5/nichols.ps.gz Nichols, David M., and Michael B. Twidale. "Matchmaking and privacy in the digital library: striking the right balance." In *ELVIRA-Proc*, pp. 31-38. 1997. ftp.comp.lancs.ac.uk/pub/reports/1997/CSEG.4.97.pdf Nichols, David. "Usage, Rating & Filtering." In *Notes from the DELOS workshop*. 1997. www.sztaki.hu/conferences/delosbudapest/papers/DELOS-dmn.ps Nickles, Matthias. *Towards a multiagent system for competitive website ratings.* Research Report FKI-243-01, Technical University Munich, 2001. wwwbrauer.informatik.tu-muenchen.de/fki-berichte/postscript/fki-243-01.ps.gz Novak, Jasminko, Monika Fleischmann, Wolfgang Strauss, Martin Schneider, Michael Wurst, Katharina Mork, A. Ziegler, and Christoph Kunz. "Augmenting the knowledge bandwidth and connecting heterogeneous expert communities through uncovering tacit knowledge." In *Knowledge Media Networking, 2002. Proceedings. IEEE Workshop on*, pp. 87-92. IEEE, 2002. maus.gmd.de/~jas/papers/kmn02.pdf O'Connor, Mark, and Jon Herlocker. "Clustering items for collaborative filtering." In *Proceedings of the ACM SIGIR workshop on recommender systems*, vol. 128. UC Berkeley, 1999. www.cs.umbc.edu/~ian/sigir99-rec/papers/oconner_m.pdf O'Connor, M., Cosley, D., Konstan, J. A., & Riedl, J. (2001). PolyLens: A Recommender System for Groups of Users. In Proceedings of ECSCW 2001, Bonn, Germany, pp. 199-218. www.cs.umn.edu/Research/GroupLens/papers/pdf/poly-camera-final.pdf O'Riordan, Colm, and Humphrey Sorensen. "Information filtering and retrieval: An overview." citeseer.nj.nec.com/483228.html (1997). www.it.nuigalway.ie/TR/abstracts/./papers/cor.ps.gz Oard, Douglas W., Nicholas DeClaris, Bonnie J. Dorr, Christos Faloutsos, and Gary Marchionini. "Experimental investigation of high performance cognitive and interactive text filtering." In *Systems, Man and Cybernetics, 1995. Intelligent Systems for the 21st Century., IEEE International Conference on*, vol. 5, pp. 4398-4403. IEEE, 1995. www.cs.kun.nl/is/research/filter/literature/perf.ps O'Hara, Kenton, and Mark Perry. "Shopping anytime anywhere." In *CHI '01 Extended Abstracts on Human Factors in Computing Systems*, pp. 345-346. ACM, 2001. www.brunel.ac.uk/~cssrmjp/homefiles/selected-publications/oharaandperry.PDF Ohsugi, Naoki, Akito Monden, and Ken-ichi Matsumoto. "A recommendation system for software function discovery." In *Software Engineering Conference, 2002. Ninth Asia-Pacific*, pp. 248-257. IEEE, 2002. se.aist-nara.ac.jp/~akito-m/home/research/paper/ohsugi_apsec2002_recommendation.pdf Ohsugi, Naoki, Akito Monden, and Shuuji Morisaki. "Collaborative Filtering Approach for Software Function Discovery." In *Int. Symp. Empirical SE (ISESE)*, vol. 2, pp. 45-46. 2002. se.aist-nara.ac.jp/~akito-m/home/research/paper/ohsugi_collaborativeFiltering_isese2002.pdf Ohura, Yusuke, Katsumi Takahashi, Iko Pramudiono, and Masaru Kitsuregawa. "Experiments on query expansion for internet yellow page services using web log mining." In *Proceedings of the 28th international conference on Very Large Data Bases*, pp. 1008-1018. VLDB Endowment, 2002. www.tkl.iis.u-tokyo.ac.jp/Kilab/Research/Paper/2002/ohura/VLDB2002Ohura.pdf Olsson, Tomas, Andreas Rasmusson, and Sverker Janson. "Personalized Decentralized Communication." In *AAAI Spring Symposium Series 2000: Bringing Knowledge to Business Processes*. 2000. www.sics.se/~tol/publications/s3-business-processes.pdf Olsson, Tomas. "Decentralised social filtering based on trust." In *proceedings of AAAI-98 Recommender Systems Workshop*, Madison, Wis. 1998. www.sics.se/~tol/publications/socialfiltering.ps O'Mahony, Michael, Neil Hurley, Nicholas Kushmerick, and Guénolé Silvestre. "Collaborative recommendation: A robustness analysis." *ACM Transactions on Internet Technology (TOIT)* 4, no. 4 (2004): 344-377. www.cs.ucd.ie/staff/nick/home/research/download/omahony-acmtit2002.pdf Paepcke, Andreas, Hector Garcia-Molina, Gerard Rodriguez-Mula, and Junghoo Cho. "Beyond document similarity: understanding value-based search and browsing technologies." *ACM SIGMOD Record* 29, no. 1 (2000): 80-92. www-db.stanford.edu/~cho/papers/info-filter.pdf Pagonis, John, and Mark C. Sinclair. "Evolving user profiles to reduce internet information overload." In *Developments in Soft Computing*, pp. 100-107. Physica, Heidelberg, 2001. esewww.essex.ac.uk/~mcs/ps/rasc00_pag.ps.gz Paik, Woojin, Sibel Yilmazel, Eric Brown, Maryjane Poulin, Stephane Dubon, and Christophe Amice. "Applying natural language processing (nlp) based metadata extraction to automatically acquire user preferences." In *Proceedings of the 1st international conference on Knowledge capture*, pp. 116-122. ACM, 2001. ranger.uta.edu/~alp/ix/readings/p116-paik-metadata-extraction-from-communications.pdf Paliouras, Georgios, Christos Papatheodorou, Vangelis Karkaletsis, and Constantine D. Spyropoulos. "Clustering the Users of Large Web Sites into Communities." In *ICML*, pp. 719-726. 2000. gdit.iiit.net/wdkm/2.pdf Palme, Jacob, Kaers, Johan, "The SELECT Protocol for Rating and Filtering" Network Working Group, Internet Draft (2000), tools.ietf.org/html/draft-palme-select-00, www.ietf.org/internet-drafts/draft-palme-select-00.ps Palme, Jacob. "Information filtering." In *Proceedings of the 12th Biennial ITS (Int'l Telecommunications Soc.) Conf.*, Stockholm. 1998. dsv.su.se/jpalme/select/information-filtering.pdf Palme, Jacob. *Choices in the Implementation of Rating*. na, 1997. www.ercim.org/publication/ws-proceedings/DELOS5/palme.pdf Papadimitriou, Christos H., Hisao Tamaki, Prabhakar Raghavan, and Santosh Vempala. "Latent semantic indexing: A probabilistic analysis." In *Proceedings of the seventeenth ACM SIGACT-SIGMOD-SIGART symposium on Principles of database systems*, pp. 159-168. ACM, 1998. lsa.colorado.edu/papers/lsi.math.prob_analysis.ps www.cs.berkeley.edu/~christos/ir.ps Papadopoulos, Nick, and Dimitris Plexousakis. "The role of semantic relevance in dynamic user community management and the formulation of recommendations." In *International Conference on Advanced Information Systems Engineering*, pp. 200-215. Springer, Berlin, Heidelberg, 2002. www.mm.di.uoa.gr/~rouvas/ssi/caise2002/23480200.pdf Payton, David. "Discovering collaborators by analyzing trails through an information space." In *Proceedings of the AAAI Fall Symposium on Artificial Intelligence and Link Analysis*, pp. 84-87. 1998. eksl-www.cs.umass.edu/aila/payton.pdf Pejtersen, Annelise Mark, Mark Dunlop, and Raya Fidel. "A use centred framework for evaluation of the web." In *Workshop presented in conjunction with the 22th Annual international ACM SIGIR conference on information retrieval*. ACM SIGIR, 1999. www.dei.unipd.it/~ims/sigir99/papers/3-pejtersen.ps Pennock, David M., Eric Horvitz. "Analysis of the axiomatic foundations of collaborative filtering." *Ann*

Arbor 1001 (1999): 48109-2110. www.eecs.umich.edu/~dpennock/homepage/papers/imposs-CF.ps Pennock, David M., Eric Horvitz, and C. Lee Giles. "Social choice theory and recommender systems: Analysis of the axiomatic foundations of collaborative filtering." In *AAAI/IAAI*, pp. 729-734. 2000. www.neci.nj.nec.com/homepages/dpennock/papers/CF-imposs-aaai-00.ps Perkowitz, Mike, and Oren Etzioni. "Towards adaptive web sites: Conceptual framework and case study." *Artificial intelligence* 118, no. 1-2 (2000): 245-275. www.cs.washington.edu/homes/map/research/papers/www8.ps Perny, Patrice, and Jean-Daniel Zucker. "Collaborative filtering methods based on fuzzy preference relations." *Proceedings of EUROFUSE-SIC* 99 (1999): 279-285. www-poleia.lip6.fr/~zucker/Papers/PPJDZ99.pdf Piatetsky, Gregory, "The Data-Mining Industry Coming of Age", IEEE Intelligent Systems, 11 Dec. 1999, pp. 32-34, www.kdnuggets.com//gpspubs/ieee-intelligent-dec-1999-x6032.pdf Platt, John C., Christopher J C Burges, Steven Swenson, Christopher Weare, and Alice Zheng. "Learning a gaussian process prior for automatically generating music playlists." In *Advances in neural information processing systems*, pp. 1425-1432. 2002. research.microsoft.com/~jplatt/autoDJ.pdf Plua, Claudia, and Anthony Jameson. "Collaborative preference elicitation in a group travel recommender system." In *Proceedings of the AH* 2002 *Workshop on Recommendation and Personalization in eCommerce*, pp. 148-154. 2002. ectrl.itc.it/rpec/RPEC-Papers/17-plua.pdf Polcicová, Gabriela, and Pavol Návrat. "Combining content-based and collaborative filtering." (2000). www.dcs.elf.stuba.sk/emg/filter.ps Polcicova, Gabriela. "Recommending HTML-documents using Feature Guided Automated Collaborative Filtering." In *Proceedings 3rd ADBIS Conference*, p. 86ce91. 1999. www.cs.umbc.edu/~ian/sigir99-rec/papers/polcicova_g.ps.gz Popescul, Alexandrin, David M. Pennock, and Steve Lawrence. "Probabilistic models for unified collaborative and content-based recommendation in sparse-data environments." In *Proceedings of the Seventeenth conference on Uncertainty in artificial intelligence*, pp. 437-444. Morgan Kaufmann Publishers Inc., 2001. www.cis.upenn.edu/~popescul/Publications/popescul01probabilistic.ps Prassas, George, Katherine C. Pramataris, and Olga Papaemmanouil. "Dynamic recommendations in internet retailing." *ECIS* 2001 *Proceedings* (2001): 84. www.eltrun.aueb.gr/papers/ecis2001.pdf Prendinger, Helmut, and Mitsuru Ishizuka. "A Comparative Study of Approaches to Chance Discovery." www.miv.t.u-tokyo.ac.jp/papers/helmut-sigfai00.pdf Procter, Rob, and Andy McKinlay. "Social affordances and implicit ratings for social filtering on the web." In *Proceedings of the Fifth DELOS L. Kolos-Mazuryk. META: enhancing presence by means of the social affordances Workshop on Filtering and Collaborative Filtering*, pp. 89-96. 1997. www.ercim.org/publication/ws-proceedings/DELOS5/procter.ps.gz Rabelo, L., and Dan Ariely. "Electronic Commerce Software Agents: How to Increase Their Machine IQ." In *Industrial Engineering Research Conference Proceedings*. 2002. fie.engrng.pittedu/iie2002/proceedings/ierc/papers/2080.pdf Rafter, Rachael, and Barry Smyth. "Passive profiling from server logs in an online recruitment environment." In *Workshop on Intelligent Techniques for Web Personalization at the the 17th International Joint Conference on Artificial Intelligence*, Seattle, Wash., USA, August, 2001. 2001. www.mineit.com/lc/ijcai/papers/rafter.pdf Rafter, Rachael, Keith Bradley, and Barry Smyth. "Automated collaborative filtering applications for online recruitment services." In *Adaptive Hypermedia and Adaptive Web-Based Systems*, pp. 363-368. Springer Berlin/Heidelberg, 2000. kermit.ucd.ie/casper/AH2000.ps Rafter, Rachael, Keith Bradley, and Barry Smyth. "Passive profiling and collaborative recommendation." In *The 10th Irish Conference on Artificial Intelligence and Cognitive Science* (*AICS* 99), Cork, Ireland, September, 1999. 1999. www.cs.ucd.ie/pubs/1999/././staff/bsmyth/home/crc/aics99f.ps Raje, Rajeev R., Snehasis Mukhopadhyay, Michael Boyles, Artur Papiez, Nila Patel, Mathew Palakal, and Javed Mostafa. "A bidding mechanism for web-based agents involved in information classification." World Wide Web 1, no. 3 (1998): 155-165. www.avl.iu.edu/~mjboyles/papers/bidding.ps Raje, Rajeev R., Snehasis Mukhopadhyay, Michael Boyles, Nila Patel, and Javed Mostafa. "D-SIFTER: a collaborative information classifier." In *Information, Communications and Signal Processing*, 1997. ICICS., *Proceedings of 1997 International Conference* on, vol. 2, pp. 820-824. IEEE, 1997. www.avl.iu.edu/~mjboyles/papers/dsifter.ps Raje, Rajeev, Snehasis Mukhopadhyay, Michael Boyles, Artur Papiez, and Javed Mostafa. "An economic framework for a web-based collaborative information classifier." In *Proceedings of the International Association of Science and Technology for Development, SE '97 Conference*, pp. 362-366. 1997. www.avl.iu.edu/~mjboyles/papers/economic.ps Ramakrishnan, Naren, Rosson, Mary Beth, "PIPE: Web personalization by partial evaluation." *IEEE Internet Computing* 4, no. 6 (2000): 21-31. www.cs.vt.edu/TR/pipe-techreport.ps Ramakrishnan, Naren. "PIPE: Web personalization by partial evaluation." *IEEE Internet Computing* 4, no. 6 (2000): 21-31. www.cs.vt.edu/~ramakris/papers/ic2000.pdf Rashid, A. M., Albert, I., Cosley, D., Lam, S. K., McNee, S., Konstan, J. A., & Riedl, J. (2002). Getting to Know You: Learning New User Preferences in Recommender Systems. In Proceedings of the 2002 International Conference on Intelligent User Interfaces, San Francisco, Calif., pp. 127-134. www.cs.umn.edu/Research/GroupLens/papers/pdf/voi-final.pdf Resnick, P., Iacovou, N., Sushak, M., Bergstrom, P., and Riedl, J. GroupLens: An open architecture for collaborative filtering of netnews. Proceedings of the 1994 Computer Supported Collaborative Work Conference. (1994)

Resnick, Paul, Neophytos Iacovou, Mitesh Suchak, Peter Bergstrom, and John Riedl. "GroupLens: an open architecture for collaborative filtering of netnews." In *Proceedings of the* 1994 *ACM Conf. Computer supported cooperative work*, pp. 175-186. ACM, 1994www.cs.kun.nl/is/research/filter/literature/GroupLens.ps sites.google.com/site/gregridgeway/papers-and-software Rocha, Ana Paula, and Eugenio Oliveira. "Electronic Commerce: a technological perspective." *O Futuro da Internet* (1999). www.fe.up.pt/~eol/PUBLICATIONS/ec98.ps Rocha, Luis Mateus. "TalkMine: a soft computing approach to adaptive knowledge recommendation." In *Soft computing agents*, pp. 89-116. Physica-Verlag HD, 2001. wwwc3.Ianl.gov/~rocha/ps/softagents. pdf Rodas Osollo, Jorge Enrique, and Gramajo Lopez. "Classification and clustering study in incomplete data domain." (2001). www.Isi.upc.es/dept/techreps/ps/R01-11.pdf.gz Rogers, Seth, Pat Langley, Bryan Johnson, and Annabel Liu. "Personalization of the automotive information environment." In *Proceedings of the workshop on Machine Learning in the real world*, pp. 28-33. 1997. www.isle.org/~langley/papers/route.m197.ps Roscheisen, Martin, Christian Mogensen, and Terry Winograd. *Shared Web annotations as a platform for third-party value-added, information providers: architecture, protocols, and usage examples*. Stanford University, Department of Computer Science, 1997. www-diglib.stanford.edu/diglib/pub/reports/commentor.ps Sarawagi, Sunita, and Sree Hari Nagaralu. "Data mining models as services on the internet." *ACM SIGKDD Explorations Newsletter* 2, no. 1 (2000): 24-28. www.it.iitb.ernet.in/~sunita/papers/sigkdd.pdf Sarwar, B. M., Karypis, G., Konstan, J. A., and Riedl, J. "Analysis of Recommender Algorithms for E-Commerce". In proceedings of the ACM E-Commerce 2000 Conference. Oct. 17-20, 2000, pp. 158-167. www.cs.umn.edu/Research/GroupLens/papers/pdf/ec00.pdf Sarwar, B., Konstan, J., Borchers, A., Herlocker, J., Miller, B., and Riedl, J. Using Filtering Agents to Improve Prediction Quality in the GroupLens Research Collaborative Filtering System. Proceedings of the 1998 Conference on Computer Supported Cooperative Work. November 1998. www.cs.umn.edu/Research/GroupLens/papers/pdf/filterbot-CSCW98.pdf Sarwar, Badrul M., Joseph A. Konstan, Al Borchers, Jon Herlocker, Brad Miller, and John Riedl. "Using filtering agents to improve prediction quality in the grouplens research collaborative filtering system." In *Proceedings of the 1998 ACM conference on Computer supported cooperative work*, pp. 345-354. ACM, 1998. www-users.cs.umn.edu/~sarwar/ms.ps Sarwar, Badrul M., Joseph A. Konstan, and J. Riedl. "Distributed recommender systems: new opportunities for internet commerce." *Internet Commerce and Software Agents: Cases, Technologies and Opportunities* (2001): 372-393, Rahman, S., and Bignall, R. eds.

Sarwar, Badrul, George Karypis, Joseph Konstan, and John Riedl. "Item-based collaborative filtering recommendation algorithms." In *Proceedings of the 10th international conference on World Wide Web*, pp. 285-295. ACM, 2001. www.cs.umn.edu/Research/GroupLens/papers/pdf/www10_sarwar.pdf Sarwar, Badrul, George Karypis, Joseph Konstan, and John Riedl. *Application of dimensionality reduction in recommender system-a case study*. No. TR-00-043. Minnesota Univ Minneapolis Dept of Computer Science, 2000. Full length paper at ACM WebKDD 2000 Web Mining for E-Commerce Workshop. www.cs.umn.edu/Research/GroupLens/papers/pdf/webKDD00.pdf www-users.cs.umn.edu/~karypis/publications/Papers/PDF/webkdd.pdf Sarwar, M., J. A. Konstant, A. Borchers, J. Herlocker, B. Miller, and J. Riedl. "Using semiintelligent filtering agents to improve prediction quality in a collaborative filtering system." In *Proc. ACM Conf. Computer Supported Cooperative Work*, pp. 245-254. 1998. www.cs.umn.edu/Research/GroupLens/filterbot-CSCW98.pdf Schafer, J. Ben, Joseph Konstan, and John Riedl. "Recommender systems in e-commerce." In *Proceedings of the 1st ACM conference on Electronic commerce*, pp. 158-166. ACM, 1999. www.cs.umn.edu/Research/GroupLens/papers/pdf/ec-99.pdf Schafer, J. B., Konstan, J., and Riedl, J., Electronic Commerce Recommender Applications. Journal of Data Mining and Knowledge Discovery, vol. 5 nos. 1/2, pp. 115-152. www.cs.umn.edu/Research/GroupLens/papers/pdf/ECRA.pdf Schapira, Agustin. "Collaboratively searching the web-an initial study." *Collaboratively searching the web: an initial study* (1999). none.cs.umass.edu:1234/~schapira/thesis/report/report.ps.gz Schmitt, Bethina. "Impact and potential of user profiles used for distributed query processing based on literature services." In *XML-Based Data Management and Multimedia Engineering—EDBT 2002 Workshops*, pp. 549-553. Springer Berlin/Heidelberg, 2002. www.cg.cs.tu-bs.de/v3d2/pubs.collection/edbt02.pdf Schubert, Petra, and Mark Ginsburg. "Virtual communities of transaction: The role of personalization in electronic commerce." *Electronic Markets* 10, no. 1 (2000): 45-55. studnet.fhbb.ch:8081/pschubert/publications/pdf-files/ta-community_schubert_ginsburg.pdf Schubert, Petra. "The pivotal role of community building in electronic commerce." In *System Sciences, 2000. Proceedings of the 33rd Annual Hawaii International Conference on*, pp. 8-pp. IEEE, 2000. studnet.fhbb.ch:8081/pschubert/publications/pdf-files/cicsp04.pdf Schwab, Ingo, Alfred Kobsa, and Ivan Koychev. "Learning about users from observation." In *AAAI 2000 Spring Symposium: Adaptive User Interface*, pp. 241-247. 2000. fit.gmd.de/~koychev/papers/AAAI00.ps Schwab, Ingo, Alfred Kobsa, and Ivan Koychev. "Learning user interests through positive examples using content analysis and collaborative filtering." *Internal Memo, GMD*, St. Augustin, Germany (2001). fit.gmd.de/~koychev/papers/MLJ-paper.pdf Schwab, Ingo, and Alfred Kobsa. "Adaptivity through unobstrusive learning." KI 16, no. 3 (2002): 5-9. www.ics.uci.edu/%7Ekobsa/papers/2002-KI-kobsa.pdf Schwab, Ingo, and Ivan Koychev. "Adaptation to Drifting User's Interests." In proc. of ECML2000 Workshop: Machine Learning in New Information Age, 2000. fit.gmd.de/~koychev/papers/MLNIA00.ps Sen, Sandip, Hernandez, Karina, "A buyers Agent", Mathematical Computer Sciences euler.mcs.utulsa.edu/~sandip/aa00-ba.ps Shashua, Amnon, and Anat Levin. "Taxonomy of large margin principle algorithms for ordinal regression problems." *Advances in neural information processing systems* 15 (2002): 937-944. leibniz.cs.huji.acil/tr/acc/2002/HUJI-CSE-LTR-2002-43_k-planes-long.ps Sinha, Rashmi R., and Kirsten Swearingen. "Comparing Recommendations Made by Online Systems and Friends." In *DELOS workshop: personalisation and recommender systems in digital libraries*, vol. 106. 2001. www.sims.berkeley.eduhsinha/papers/Recommenders_Delos01.PDF Smyth, Barry, and Paul Cotter. "Content Personalisation for WAP-enabled Devices." memory 1 (2000): 4. www.ics.forth.gr/~potamias/mlnia/paper_8.pdf Smyth, Barry, Paul Cotter, and Greg M P O'Hare. "Let's get personal: Personalised TV listings on the web." In *9th Irish Conference on Artificial Intelligence and Cognitive Science*, 1998, Dublin, Ireland, 19-21 Aug. 1998. www.cs.ucd.ie/pubs/1998/././staff/bsmyth/home/crc/aics98a.ps Smyth, Padhraic. "Data mining at the interface of computer science and statistics." *Data mining for scientific and engineering applications* 2 (2001): 35-61. www.ics.uci.eduhdatalab/papers/dmchap.ps Soboro, Ian M. "Collaborative Filtering with LSI: Experiments with Cranfield." (1998). www.cs.umbc.edu/~ian/pubs/tr9801.ps.gz Soboroff, Ian, and Charles Nicholas. "Combining content and collaboration in text filtering." In *Proceedings of the IJCAI*, vol. 99, pp. 86-91. sn, 1999. www.cs.umbc.eduhian/pubs/mlif.ps.gz Soltysiak, S. J., and I. B. Crabtree. "Automatic learning of user profiles—towards the personalisation of agent services." *BT Technology Journal* 16, no. 3 (1998): 110-117. www.labs.bt.com/projects/agents/publish/papers/bttj98-profiling.pdf Soltysiak, Stuart, and Barry Crabtree. "Knowing me, knowing you: practical issues in the personalisation of agent technology." In *Proc. of the 3rd International Conference on the Practical Application of Agents and Multi-Agent Technology*, U K. 1998. www.labs.bt.com/projects/agents/publish/papers/ss_bc-paam98.ps Specht, Marcus, and Reinhard Oppermann. "User modeling and adaptivity in nomadic information systems." In *In Mimo Caenepeel*, David Benyon & Duncan Smith (eds.), *Proceedings of the i3 Annual Conference: Community of the Future.* 1999. fit.gmd.de/~oppi/publications/ABIS-hip.pdf Spertus, Ellen, and Lynn Andrea Stein. "A Hyperlink-Based Recommender System Written in Sqeal." In *Workshop on Web Information and Data Management*, pp. 1-4. 1998. www.mills.edu/ACAD_INFO/MCS/SPERTUS/widm98.pdf Spertus, Ellen, and Lynn Andrea Stein. "Mining the Web's Hyperlinks for Recommendations." In *AAAI-98 Recommender Systems Workshop Papers*, pp. 84-88. www.mills.edu/ACAD_INFO/MCS/SPERTUS/recommender-workshop.pdf Spertus, Ellen. "ParaSite: mining the structural information on the World-Wide Web." PhD diss., Massachusetts Institute of Technology, 1998. www.mills.edu/ACAD_INFO/MCS/SPERTUS/Thesis/thesis.pdf Staab, Steffen. "Human language technologies for knowledge management." *IEEE Intelligent Systems* 16, no. 6 (2001): 84-94. www.mitre.org/support/papers/tech_papers_01/maybury_humanlanguage/maybury_hlt.pdf Stenmark, Dick. "Collaborative aspects of information retrieval tools: Summarising three action case studies." (2000). w3.adb.gu.se/~dixi/publ/iris23ca.pdf Stephanidis, Constantine, ed. *User interfaces for all: concepts, methods, and tools*. CRC Press, 2000, www.g-md.de/publications/report/0074/Text.pdf Svensson, Martin, Jarmo Laaksolahti, Kristina Höök, and Annika Waern. "A recipe based on-line food store." In *Proceedings of the 5th international conference on Intelligent user interfaces*, pp. 260-263. ACM, 2000. www.sics. se/~martins/publications/chi99.pdf. lieber.www. media. mit.edu/people/lieber/IUI/Svensson/Svensson.pdf Svensson, Martin, Per Persson, and Kristina Höök. "Using Narratives, Humor, and Social Navigation: An Inspection of Two Systems." (1999). www.sics.se/~perp/UserModelling99.pdf Swearingen, Kirsten, and Rashmi Sinha. "Beyond algorithms: An HCl perspective on recommender systems." In *ACM SIGIR 2001 Workshop on Recommender Systems*, vol. 13, no. 5-6, pp. 1-11. 2001. www.sims.berkeley.edu/~sinha/papers/BeyondAlgorithms.pdf Swets, John A. "Measuring the accuracy of diagnostic systems." *Science* 240, no. 4857 (1988): 1285-1293.

Talwar, Varun, and M. P. S. Bhatia. "Bayesian Learning for Personlization in Information Retrieval." dcs.vein.hu/CIR/cikkek/paper_acmsig.pdf Tatemura, Junichi. "Virtual reviewers for collaborative exploration of movie reviews." In *Proceedings of the 5th international conference on Intelligent user interfaces*, pp. 272-275. ACM, 2000. lieberwww.media.mit.edu/people/lieber/IUI/Tatemura/Tatemura.pdf Terveen, Loren, and Will Hill. "Evaluating emergent collaboration on the Web." In *Proceedings of the 1998 ACM conference on Computer supported cooperative work*, pp. 355-362. ACM, 1998. www.research.att.com/~terveen/cscw98.ps Terveen, Loren, Will Hill, Brian Amento, David McDonald, and Josh Creter. "PHOAKS: A system for sharing recommendations." *Communications of the ACM* 40, no. 3 (1997): 59-62. www.pensivepuffin.net/%7Edavid/papers/Terveen.CACM97.pdf The Use Of Case-Based Reasoning (CBR) For Knowledge Enablement Of.—Hodgson (2000) www.ifcomputer.co.jp/sol2000/papers/hodgson.pdf Tomlinson, Bill, Bruce Blumberg, and Bradley Rhodes. "How is an agent like a wolf?: Dominance and submission in multi-agent systems." In *International ICSC Symposium on Multi-Agents and Mobile Agents in Virtual Organizations and E-Commerce* (MAMA'2000). 2000. badger.www.media.mit.edu/people/badger/Publications/MAMA-175.pdf Toolan, Fergus, and Nicholas Kusmerick. "Mining web logs for personalized site maps." In *Web Information Systems Engineering (Workshops)*, 2002. *Proceedings of the Third International Conference on*, pp. 232-237. IEEE, 2002. www.cs.ucd.ie/staff/nick/home/research/download/toolan-mews2002.pdf Towle, Brendon, and Clark Quinn. "Knowledge based recommender systems using explicit user models." In *Proceedings of the AAAI Workshop on Knowledge-Based Electronic Markets*, pp. 74-77. 2000. www.igec.umbc.edu/kbem/final/towle.pdf Tresp, Volker. "Mixtures of Gaussian processes." In *Advances in neural information processing systems*, pp. 654-660. 2001. dnkweb.denken.or.jp/boosting/papers/upload_7245_moe_gpr2.ps Tveit, Amund. "Finding Relevant Litterature for Agent Research." (2000). cavenan.idi.ntnu.no/amund/publications/2000/AgentLitteratureSearch.pdf Tveit, Amund. "Web Usage Mining with Inductive Logic Programming." (2000). cavenan.idi.ntnu.no/amund/publications/2000/WebMiningWithILP.pdf Twidale, Michael, and David Nichols. "A survey of applications of CSCW for digital libraries: Technical Report CSEG/4/1998." (1998). ftp.comp.lancs.ac.uk/pub/reports/1998/CSEG.4.98.pdf Twidale, Michael, and David Nichols. "Collaborative browsing and visualisation of the search process." In *Aslib Proceedings*, vol. 48, no. 7-8, pp. 177-182. 1996. ftp.comp.lancs.ac.uk/pub/reports/1996/CSEG.3.96.ps.Z Umeda, Y., Hiroyuki Tarumi, and Yahiko Kambayashi. "Design and development of a cooperative shopping system with shared discussion space." In *Parallel Processing, 1999. Proceedings. 1999 International Workshops on*, pp. 100-105. IEEE, 1999. www.isse.kuis.kyoto-u.ac.jp/~tarumi/research/papers/iwcmc.pdf Ungar, Lyle H., and Dean P. Foster. "Clustering methods for collaborative filtering." In *AAAI workshop on recommen-* dation systems, vol. 1, pp. 114-129. 1998. www.cis.upenn.edu/datamining/Publications/clust.pdf Using Color and Texture Indexing to improve Collaborative.—Arnd Kohrs And (1999) www.eurecom.fr/~kohrs/publish/CBMI99.ps.gz Van der Putten, Peter, Joost N. Kok, and Amar Gupta. "Data fusion through statistical matching." (2002). www.liacs.nl/~putten/library/2002stt_65_part_3_2_6.pdf Van Meteren, Robin, and Maarten Van Someren. "Using content-based filtering for recommendation." In *Proceedings of the Machine Learning in the New Information Age: MLnet/ECML2000 Workshop*, pp. 47-56. 2000. www.ics.forth.gr/~potamias/mlnia/paper_6.pdf Verykios, Vassilios S., Elias N. Houstis, and John R. Rice. "A knowledge discovery methodology for the performance evaluation of scientific software." (1998). www.cs.purdue.edu/homes/verykios/personal/papers/kais98.ps Viberg, Tomas, "Client-Side Proxies—A Better Way To Individualise the Internet?" Masters Thesis, Stockholm U., (May 2000) cmc.dsv.su.se/select/csp/thesis.pdf Villa, Robert, and Matthew Chalmers. "A Framework for Implicitly Tracking Data." In *DELOS Workshop: Personalisation and Recommender Systems in Digital Libraries*. 2001. www.ercim.org/publication/ws-proceedings/DelNoe02/RobertVilla.pdf Vogt, Christopher C., and Garrison W. Cottrell. "Using d' to optimize rankings." (1998). www.cs.ucsd.edu/~vogt/papers/dprime/dprime.ps Voss, Angi, and Thomas Kreifelts. "SOAP: social agents providing people with useful information." In *Proceedings of the international ACM SIGGROUP conference on Supporting group work: the integration challenge*, pp. 291-298. ACM, 1997. www.gmd.de/fit/publications/ebk-publications/SOaP.pdf Vucetic, Slobodan, and Zoran Obradovic. "A regression-based approach for scaling-up personalized recommender systems in e-commerce." *WEBKDD'00* (2000). robotics.stanford.edu/~ronnyk/WEBKDD2000/papers/vucetic.ps Waern, Annika, Mark Tierney, Åsa Rudstrom, Jarmo Laaksolahti. "ConCall: An information service for researchers based on EdInfo." (1998). ftp.sics.se/pub/SICS-reports/Reports/SICS-T-98-04-SE.ps.Z Weiss, Sholom, and Nitin Indurkhya. "Lightweight collaborative filtering method for binary-encoded data." *Principles of Data Mining and Knowledge Discovery* (2001): 484-491. www.research.ibm.com/dar/papers/pdf/weiss_pkdd01.pdf Weld, Daniel S.; Levy, Alon, "Intelligent Internet Systems", Jan. 7, 1998. (Searching The Web-Meta-Search Hybrid Approaches) www.cs.washington.edu/education/courses/cse574/98wi/toc.ps Whittaker, Steve, Loren Terveen, and Bonnie A. Nardi. "Let's stop pushing the envelope and start addressing it: a reference task agenda for HCI." *Human-Computer Interaction* 15, no. 2-3 (2000): 75-106. www.research.att.com/~stevew/reference_task_hci2000.pdf www.research.att.com/~terveen/envelope.ps www.research.att.com/~stevew/envelope-5-15-00-FINAL.pdf Widyantoro, Dwi Hendratmo. "Dynamic modeling and learning user profile in personalized news agent." Master's thesis, Texas A&M University, 1999. students.cs.tamu.edu/dhw7942/thesis.ps Winiwarter, Werner, M. Hoefferer, and B. Knaus. "Cognitive Filtering of Information by Evolutionary Algorithms." (1995). ftp.ifs.univie.ac.at/pub/wernerwiniwarter/ki94if.ps.gz Witenstein, Mike, "Adaptive Marketing: Building an intuitive enterprise", Centers for IBM e-business Innovation, www.systemicbusiness.org/pubs/2000_IBM_e-Business_Wittenstein_Adaptive_Marketing.pdf Wittig, Frank. "Some issues in the learning of accurate, interpretable user models from sparse data." In *Proceedings of the UM2001-Workshop on "Machine Learning for User Modeling*, pp. 11-21. 2001. www.dfki.dehrafer/um01-ml4um-ws/papers/FW.ps.gz Wright, Michael J. "Constituencies for users: How to develop them by interpreting logs of web site access." In *AAAI Spring Symposium on Intelligent Agents in Cyberspace*, Stanford, Calif., USA. 1999. www.cs.colorado.edu/~sumner/cs3202/kmi-tr-75.pdf Wright, Steven. "Personalisation: How a computer can know you better than yourself." In University of Southampton. 2002. Can mms.ecs.soton.ac.uk/papers/14.pdf Yamada, Seiji, Motohiro Mase, and IGSSE CISS. "Integrated information search in the WWW and a human group." *Proceedings of INFORMS/KORMS* (2000). ftp.ymd.dis.titech.ac.jp/pub/doc/references/2000/INFORMS-2000-mase.ps.gz Yimam, Dawit, and Alfred Kobsa. "Demoir: A hybrid architecture for expertise modeling and recommender systems." In *Enabling Technologies: Infrastructure for Collaborative Enterprises*, 2000. *(WET ICE 2000). Proeedings. IEEE 9th International Workshops on*, pp. 67-74. IEEE, 2000. www.ics.uci.edu/~kobsa/papers/2000-1EEE-kobsa.pdf Yu, Bin, Mahadevan Venkatraman, Munindar P. Singh. "The MARS adaptive social network for information access: architecture and experimental results." (1999): 99-10. www4.ncsu.edu/~byu/papers/mars-experiments.pdf www.csc.ncsu.edu/faculty/mpsingh/papers/mas/mars-experiments.ps Zaiane, Osmar R., and Jun Luo. "Towards evaluating learners' behaviour in a web-based distance learning environment." In *Advanced Learning Technologies, 2001. Proceedings. IEEE International Conference on*, pp. 357-360. IEEE, 2001. www.cs.ualberta.ca/~zaiane/postscript/CATE2001.pdf Zaiane, Osmar. "Web usage mining for a better web-based learning environment." (2001). www.cs.ualberta.ca/~zaiane/postscript/CATE2001.pdf Zhang, Bin, Meichun Hsu, and George Forman. "Accurate recasting of parameter estimation algorithms using sufficient statistics for efficient parallel speed-up." *Principles of Data Mining and Knowledge Discovery* (2000): 125-161. www.hpl.hp.com/org/stl/dmsd/publications/ParaPKDD.pdf Zhang, Jiajie. "A distributed representation approach to group problem solving." *Journal of the American Society for Information Science* 49, no. 9 (1998): 801-809. www.brunel.ac.uk/~cssrmjp/MP_thesis/references.pdf www.inference.phy.cam.ac.uk/mackay/Bayes_FAQ.html
www-2.cs.cmu.edu/Groups/AI/html/faqs/ai/neural/faq.html
www.cs.stir.ac.uk/~lss/NNIntro/InvSlides.html
diryahoo.com/Science/Engineering/Electrical_Engineering/Neural_Networks/
www.aist.go.jp/NIBH/~b0616/Links.html
www.creative.net.au/~adrian/mirrors/neural/
www.fi.uib.no/Fysisk/Teori/NEURO/neurons.html
aass.oru.sehtdt/ann/faq/FAQ.html
www.cis.hut.fihjari/research.html
www.eg3.com/WebID/elect/neur-net/blank/overview/a-z.htm directory.google.com/Top/Computers/Artificial_Intelligence/Neural_Networks/
directory.google.com/Top/Computers/Artificial_Intelligence/Neural_Networks/FAQs,_Help,_and_Tutorials
dmoz.org/Computers/Artificial_Intelligence/Neural_Networks/
dmoz.org/Computers/Artificial_Intelligence/Neural_Networks/FAQs,_Help,_and_Tutorials/
www.cs.qub.ac.uk/~J.Campbell/myweb/book/nn.html
www.cere.pa.cnr.it/IDAschool/lectures/neural.html
cognet.mit.edu/MITECS/Entry/jordan2
www.faqs.org/faqs/ai-faq/neural-nets/part1/preamble.html
zhanshou.hypermart.net/thesis.htm
www.links999.net/hardware/neural.html
www-ra.informatik.uni-tuebingen.de/links/neuronal/welcome_e.html
www.cogneuro.ox.ac.uk/links/ann.html
faculty.cs.tamu.edu/choe/resources/
www.galaxy.com/galaxy/Engineering-and-Technology/Electrical-Engineering/Neural-Networks/
mu.dmt.ibaraki.ac.jp/yanai/neu/faq/
bubl.ac.uk/link/n/neuralnetworks.htm
www.webopedia.com/TERM/n/neural_network.html
www.ie.ncsu.edu/fangroup/neural.dir/indexneural.html
www.geneticprogramming.com/Al/nn.html
www.cs.utk.eduhyarkhan/neural_networks.html
www.physiol.ox.ac.ukhket/nn.html
www.aaai.org/AlTopics/html/neural.html
www.inference.phy.cam.ac.uk/mackay/itprnn/book.html
www.hh.se/staff/nicholas/NN_Links.html
xpidea.com/products/neurovcl/neuroabout.htm
www.msm.ele.tue.nl/research/neural/
homepages.goldsmiths.ac.uk/nikolaev/Nnets.htm
www.triumf.ca/project_ETA/neural_network.html
personal.bgsu.edu/~suny/nn.html
www.icmc.sc.usp.brhandre/ann_links.html
www.stud.ntnu.nohhirpa/links/Al_links.htm
it.umary.edu/Library/research/www_subjects/neural_networks.html
cindy.cis.nctu.edu.tw/NN/NN5/www.html
www.public.iastate.edu/~acl/links/links.html
www.cs.cf.ac.uk/User/O.F.Rana/neural.html
www.cs.unredu/~bebis/CS791S/
www.geocities.com/fastiland/NNwww.html
cns-web.bu.edu/pub/snorrason/bookmarks/neural.html
www.open.brain.riken.go.jp/~cao/index_work.html
svr-www.eng.cam.ac.uk/research/neural/other_neural_net_sites.html
Game Theory
GEB: Games and Economic Behavior
EMA: Econometrica
JET: Journal of Economic Theory
IJGT: International Journal of Game Theory
AER: American Economic Review
QJE: Quarterly Journal of Economics
JPE: Journal of Political Economy
REStud: Review of Economic Studies
Description of Games
Roger Myerson, Nash Equilibrium and the History of Economic Theory. JEL 1999
Rationality, Dominance, Weak Dominance etc
Douglas Bernheim, Rationalizable strategic behavior. EMA 1984
David Pearce, Rationalizable strategic behavior and the problem of perfection. EMA 1984
Douglas Bernheim, Axiomatic characterization of rational choice in strategic enviroments. Scand. J. of E. 1986
Shimoji and Watson, Conditional Dominance, rationalizability and game forms. JET 1998
David Roth, Rationalizable predatory pricing. JET 1996
Basu and Weibul, strategy subsets closed under rational behavior. E. Letters 1991
Larry Samuelson, Dominated strategies and common knowledge. GEB 1992
Marx and Swinkels, Order independence for iterated weak dominance. GEB 1997
Equilibrium: Nash, Refinements, Correlated
Selten, Reexamination of the Perfectness concept for equilibrium points in extensive form games. IJGT 1975.
Myerson, Refinements of the Nash equilibrium concept. IJGT 1975.
Kalai and Samet, Persistent equilibria in strategic games. IJGT 1984.
Kohlberg and Mertens, On the strategic stability of Equilibria. Econometrica, 1986.
Aumann, Correlated equilibria as an expression of baysian rationality. Econometrica, 1987.
Aumann and Brandenberger, Espitemic conditions for equilibrium. EMA 1995
Hal Varian, A model of Sales. AER 1980
The Extensive Form Games with Perfect Information
Rubinstein, On the interpretation of game theory. Econometrica 1991
Reny, Common beleifs and the theory of games with perfect information. JET 1993.
Aumann Backward induction and common knowledge of rationality. GEB 1995
Binmore, A note on backward induction: Aumann, Reply to Binmore. GEB 1996
Selten, A Reexamination of the perfectness.
Hyperbolic Discounting
O'Donoghue and Rabin, Doing it now or doing it later. AER 1999
David Laibson, Golden Eggs and Hyperbolic Discounting. QJE 1997
The Economics of Altruism
Gary Becker, A theory of social interactions. JPE 1974
Ted Bergstrom, A fresh look at the rotten kid theorem and other household mysteries. JPE 1989
Bernheim and Stark, Altruism within the family reconsidered: do nice guys finish last. AER 1988
Lindbeck and Weibull, Altruism and time consistency: the economics of fait accompli. JPE 1988
Bruce and Waldman, Transfers in kind: why they can be efficient and non-paternalistic. AER 1991
Jack Robles, Paternal altruism or smart parent altruism? CU WP 98-10
Mathew Rabin, Incorporating fairness into economics and game theory. AER 1993
Ray and Ueda, Egalitarianism and incentives. JET 1996
Bernheim, Shleifer adn Summers, The strategic bequest motive. JPE 1985
Extensive Form Games without Perfect Information
Kreps and Wilson, Sequential Equilibrium. Econometrica, 1983.
Van Damme, Stable Equilibria and forward induction. JET 1989.
Strategic Information Transmission
Crawford and Sobel, Strategic information transmission. Econometrica 1982.
Cho and Kreps, Signalling games and stable equilibria. QJE 1987
Mailath, Okuno-Fujiwara and Postlewaite, Beleif based refinements in signalling games. JET 1993

Milgrom and Roberts, Limit pricing and entry under incomplete information: an equilibrium analysis. EMA 1982 (pages 443-459)

Cho and Sobel, Strategic Stability and uniqueness in signalling games. JET 1990.

Farrell, Meaning and credibility in cheap talk games. GEB

Milgrom and Roberts, Limit pricing and entry under incomplete information, an equilibrium analysis, EMA 1982

Milgrom, Good news and bad news, representation and applications, Rand.

Folk Theorems for Repeated Games

Dilip Abreu. On the theory of infinitely repeated games with Discounting. Econometrica 1988

Benoit and Krishna. Finitely Repeated games. Econometrica, 1985.

James Friedman. A noncooperative equilibrium for supergames. REStud 1971.

James Friedman. Cooperative equilibria in finite horizon supergames. JET 1985.

Fudenberg and Maskins. The Folk Theorem in repeated gmaes with discounting or with incomplete information. Econometrica 1986.

Roy Radner. Collusive Behavior in non-cooperative epsilon equilibria in oligopolies with long but finite lives. JET 1980.

Ariel Rubinstein. Equilibrium in supergames with the overtaking criterion. JET 1977.

Renegotiation

Benoit and Krisna, Renegotiation in finitely repeated games. EMA 1993

Bergin and MacCleod, Efficiency adn renegotiation in repeated games. JET 1993

Andreas Blume, Interplay communication in repeated games. GEB 1994

Geir Asheim, Extending renegotiation proofness to infinite horizon games. GEB 1991

Bernheim and Ray, Collective dynamic consistency in repeated games. GEB 1989

Farrel and Maskin, Renegotiation in Repeated Games. GEB 1989

Cooperative Game Theory

Freidman, Game theory with applications to economics chapter 6 and 7

Nash, The Bargaining problem. EMA 1950

Kalai and Smordinski, Other Solutions to Nash's problem. EMA 1975

Noncooperative Bargaining

Rubinstein, Perfect equiibrium in a bargaining model. EMA 1982

Joel Watson, Alternating offer bargaining with two sided incomplete information. REStud 1999

Reputation

Kreps, Milgrom, Roberts and Wilson, Reputation and imperfect information: predation, reputation and entry deterence: rational cooperation in the finitely repeated prisoner's dilemma. JET 1981

Aumann and Sorin, Cooperation and Bounded recal. GEB 1989

Klaus Schmidt, Reputation and equilibrium characterization in repeated games with conflicting interests, Econometrica 1993, 325-352

Cripps and Thomas, Reputation and Commitment in Two person games without discounting, EMA, 1995, 1401-1420

Joel Watson, A reputation refinement without equilibrium, EMA 1993, 199-206

Celentani, Fudenberg and Levine, Maintaining a reputation against a long lived opponent EMA 1996, 691-704

Evolutionary Game Theory

Vince Crawford, An Evolutionary interpretation of VHBB's experimental results on coordination. GEB 1991

Gilboa and Matsui, Social Stability and Equilibrium, EMA 1991

Kandori, Mailath and Rob, Learning, Mutation, and Long Run Equilibria in games, EMA 1993.

Peyton Young, An Evolutionary Model of Bargaining, JET 1993

Peyton Young, The Evolution of Conventions, EMA 1993

Larry Samuelson, Stochastic Stability with alternative best replies. JET

Noldeke and Samuelson, The Evolution of Backwards and Forwards Induction, GEB 1993

Jack Robles, An Evolutionary Folk Theorem For Finitely Repeated Games CU WP 99

Kim and Sobel, An Evolutionary Approach to Preplay Communication EMA 1995

General Game Theory

Bierman H. S. & Fernandez L., Game Theory with Economic Applications, Addison-Wesley, 1993.

Dixit A., & Nalebuff B., Thinking Strategically: the Competitive Edge in Business, Politics, and Everyday Life, New York: Norton, 1991.

McMillan J., Games, Strategies, and Managers, Oxford: OUP, 1992.

Baird D. G., Gertner R. H., and Picker R. C., Game Theory and the Law, Harvard U. P., 1994.

Rasmusen E., Games and Information: An Introduction to Game Theory, Oxford: B. Blackwell, 2nd edition, 1994.

Ghemawat P., Games Businesses Play: Cases and Models, New York: Wiley, 1995.

Gardner R., Games for Business and Economics, New York: Wiley, 1995.

Strategic Decision Making

Dixit & Nalebuff, Intro; Ch2 Anticipating your rival's response;

Ch3 Seeing through your rival's response.

Barnett, F. W. Making game theory work in practice, Wall Street Journal, 1995.

Bierman & Fernandez, Ch5 Nash equilibrium I, Ch11 Nash equilibrium II

O'Neill B., International escalation and the dollar auction, Journal of Conflict Resolution, 1986.

Schelling T. C., Ch7 Hockey helmets, daylight saving, and other binary choices, in his Micromotives and Macrobehavior, NY: Norton, 1978.

Marks R. E., Competition and common property, 1998.

McMillan J., Ch3 Understanding cooperation and conflict.

McAfee R. P. & J. McMillan, Competition and game theory, Journal of Marketing Research, 1996.

Baird, Gertner, & Picker, Ch1 Simultaneous decision-making and the normal form game.

Gardner, Ch1 Introduction, Ch2 Two-person games, Ch16 Voting games.

Rasmusen, Ch1 The rules of the game.

Schelling T. C., What is game theory? in his Choice and Consequence: Perspectives of an Errant Economist, Camb.: Harvard UP, 1980.

Decision Analysis—Games Against Nature

Apocalpse maybe, and An insurer's worst nightmare, The Economist, 1995/96

Bierman & Fernandez, Chs 1-3.

Ulvila J. W. & R. Brown, Decision analysis comes of age, Harvard Buisness Review 1982.

Howard R. A., Decision analysis: practice and promise, Management Science, 1988.

Clemen R. T., Making Hard Decisions: An Introduction to Decision Analysis, Belmont, Calif.: Duxbury, 1996.

Samson D., Chs 2-6, 11, Managerial Decision Analysis, Chicago: R. D. Irwin, 1988.

Strategic Moves

Dixit & Nalebuff, Ch5 Strategic moves.

Brams S. J. & J. M. Togman, Cooperation through threats: the Northern Ireland case, PS: Political Science & Politics, March 1998.

Gardner, Ch4 n-person games, Ch5 Non-cooperative games.

Colman A. M., Ch8 Multi-person games: social dilemmas, in his Game Theory and Experimental Games, Oxford: Pergamon, 1982.

Kay J., Ch3 Co-operation and Co-ordination, in his Foundations of Corporate Success: How Business Strategies Add Value, Oxford: OUP, 1993.

Brams S. J., Ch1 International relations games, in Game Theory and Politics, NY: Macmillan, 1975.

Credible Commitment

Dixit & Nalebuff, Ch6 Credible commitments.

Bierman & Fernandez, Ch23 Subgame-perfect equilibrium

Rasmusen, Ch4.1 Subgame perfection.

Gardner, Ch6 Credibility and subgame perfection.

Ghemawat, Ch3 Preemptive capacity expansion in the titanium dioxide industry.

Repetition and Reputation

Dixit & Nalebuff, Ch4 Resolving the Prisoner's Dilemma; Ch9 Cooperation and coordination.

Nowak, M., R. May, & K. Sigmund, The arithmetic of mutual help, Scientific American, 1995

Hofstadter D., Ch29 The Prisoner's Dilemma computer tournaments and the evolution of cooperation, in his Metamagical Themas, Penguin, 1985.

Marks R. E., Midgley F D. F., & Cooper L. G., Adaptive behaviour in an oligopoly, in Evolutionary Algorithms in Management Applications, ed. by J. Biethahn & V. Nissen, (Berlin: Springer-Verlag), 1995.

Baird Gertner & Picker, Ch2 Dynamic interaction and the extensive-form game, Ch5 Reputation and repeated games.

Gardner, Ch7 Repeated games, Ch8 Evolutionary stability and bounded rationality.

Rasmusen, Ch4 Dynamic games and symmetric information, Ch5 Reputation and repeated games with symmetric information.

Unpredictability

Dixit & Nalebuff, Ch7 Unpredictability; Ch8 Brinkmanship.

Bierman & Fernandez, Ch11.9

Gardner, Ch3 Mixed strategies.

Rasmusen, Ch3 Mixed and continuous strategies.

Bargaining

Dixit & Nalebuff, Ch10 The voting strategy; Ch11 Bargaining.

McMillan, Ch5 Gaining bargaining power; Ch6 Using information strategically.

Elster J., Ch14 Bargaining, in Nuts and Bolts for the Social Sciences, Camb.: CUP, 1989

Murnighan J. K., Game's End, Chapter 15 in his: Bargaining Games: A New Approach to Strategic Thinking in Negotiations, NY: William Morrow, 1992.

Bierman & Fernandez, Ch6 Bargaining.

Schelling T. C., Ch2 Essay on bargaining, in The Strategy of Conflict, Camb.: Harvard UP, 1980.

Baird Gertner & Picker, Ch7 Noncooperative bargaining

Gardner, Ch12 Two-person bargains. Ch14 n-person bargaining and the core.

Rasmusen, Ch11 Bargaining.

Brams S. J., Negotiation Games: Applying Game Theory to Bargaining and Arbitration, NY: Routledge, 1990.

Using Information Strategically

McMillan, Ch6 Using information strategically

Bierman & Fernandez, Ch17 Bayesian equilibrium, Ch19 Adverse selection and credit rationing Rasmusen, Ch2 Information P-13

Baird Gertner & Picker, Ch4 Signalling, screening, and nonverifiable information Gardner, Ch9 Signaling games.

Bidding in Competition

Revenge of the nerds, It's only a game, and Learning to play the game, The Economist, 1994

Landsburg S. E., Cursed winners and glum losers, Ch18 of his The Armchair Economist: Economics and Everyday Life, New York: The Free Press, 1993.

Norton, R., Winning the game of business, Fortune, 1995,

Koselka, R., Playing poker with Craig McCaw, Forbes, 1995,

Dixit & Nalebuff, Ch12 Incentives.

McMillan, Ch11 Bidding in competition

McAfee R. P. & J. McMillan, Analyzing the airwaves auction, Journal of Economic Perspectives, 1996

R. Marks, Closed tender vs. open bidding auctions, 22 Dec. 1994.

The Economist, Secrets and the prize, 12 Oct. 1996, p. 98.

Scientific American, Making honesty pay, January 1997, p. 13.

Gardner, Ch11 Auctions.

Brams S. J. & A. D. Taylor, Fair division by auctions, Ch9 of their Fair Division: From Cake-Cutting to Dispute Resolution, Cambridge: CUP, 1996.

Rasmusen, Ch12 Auctions.

Contracting, or the Rules of the Game

Kay, Ch4 Relationships and contracts.

Dixit & Nalebuff, Ch12 Incentives.

McMillan, Ch8 Creating incentives; Ch9 Designing contracts; Ch10 Setting executives' salaries.

Williamson O. E., Strategizing, economizing, and economic organization, Strategic Management Journal, 1991.

Bierman & Fernandez, Ch7 Involuntary unemployment.

Gardner, Ch10 Games between a principal and an agent.

Milgrom P. & Roberts J., Ch5 Bounded rationality and private information; Ch6 Moral hazard and performance incentives. Economics, Organization and Management, Englewood Cliffs: Prentice-Hall, 1992.

Choosing the Right Game: Co-Opetition

Brandenburger A. M. & B. J. Nalebuff, The right game: using Game Theory to shape strategy, Harvard Business Review, 1995 mayet.som.yale.edu/coopetition/index2.html Koselka R., Businessman's dilemma, and Evolutionary economics: nice guys don't finish last, Forbes, Oct. 11, 1993.

Brandenburger A. M. & B. J. Nalebuff, Co-opetition: 1. A revolutionary mindset that combines competition and cooperation; 2. The Game Theory Strategy that's changing the game of business. New York: Currency Doubleday, 1996.

Brandenburger A. M. & Harborne W. S. Jr., Value-based business strategy, Journal of Economics and Management Strategy, 5(1), 1996.

Baird Gertner & Picker, Ch6 Collective action, embedded games, and the limits of simple models.

Morrow J. D., Game Theory for Political Scientists, Princeton: P.U.P., 1994.
Casson M., The Economics of Business Culture: Game Theory, Transaction Costs and Economic Performance, Oxford: OUP, 1991.
Schelling T. C., Altruism, meanness, and other potentially strategic behaviors, American Economic Review, 68(2): 229-231, May 1978.
Crawford V. P., Thomas Schelling and the analysis of strategic behavior, in Strategy and Choice, ed. by R. J. Zeckhauser, MIT Press, 1991.
For a history of game theory since Old Testament times, point your browser at the following URL: www.canterbury.ac.nz/econ/hist.htm
www.pitt.eduhalroth/alroth.html
Eddie Dekel, Drew Fudenberg and David K. Levine, Learning to Play Bayesian Games (Jun. 20, 2001). www7.kellogg.northwestern.edu/research/math/papers/1322.pdf
www.gametheory.net/html/lectures.html
Drew Fudenberg and David K. Levine, The Nash Threats Folk Theorem With Communication and Approximate Common Knowledge in Two Player Games (Jun. 10, 2002).

What is claimed is:

1. A method of targeting a communication based on an expected performance, comprising:
   receiving a plurality of communications;
   determining a request for performance in conjunction with each respective communication;
   determining, for each respective communication, a set of possible targets for receiving the respective communication;
   selecting, for each respective communication, an optimum respective target from the set of possible targets, said selecting being optimized based on at least: an expected value of the determined performance of the request, a competitive alternate allocation of the respective possible target, a cost of allocation of the respective possible target to the respective communication, and an anticipated wait time for availability of the possible target; and
   producing at least one control signal for targeting the respective communication to the optimum respective target.

2. The method according to claim 1, wherein said selecting is further optimized based on a comprehensive evaluation of all competitive alternate allocations of the respective possible target.

3. The method according to claim 1, wherein the plurality of communications comprise voice communications.

4. The method according to claim 1, wherein the set of possible targets comprise call center agents.

5. The method according to claim 1, wherein the expected value comprises a revenue or profit metric.

6. The method according to claim 1, wherein the cost of allocation comprises a compensation rate of a respective target over an expected duration of the communication.

7. The method according to claim 1, wherein the performance of the request in conjunction with each respective communication is determined through interactive voice response.

8. The method according to claim 1, wherein said selecting comprises calculating a composite metric for each respective target, and selecting the target as the possible target having the best metric.

9. The method according to claim 1, wherein the control signal controls a telephone system.

10. The method according to claim 1, wherein the expected value of the determined performance of the request is based on at least a past history of a source of the respective communication.

11. A system for targeting a communication based on an expected performance, comprising:
    input ports configured to receive a plurality of communications;
    an automated communication process configured to determine a request for performance for each respective communication;
    at least one automated processor, configured to:
      determine a set of possible targets for each respective communication comprising a plurality of possible targets;
      select an optimal target based on at least a determination for each respective communication, and for each possible target, an expected value of the determined performance of the request, a competitive alternate allocation of the respective possible target, a cost of allocation of the respective possible target to the respective communication, and an anticipated wait time for availability of the possible target; and
      produce at least one control signal for controlling the respective communication with respect to allocation to the optimum respective target; and
    an output configured to produce a control signal for controlling communication routing of the communication to the optimum respective agent.

12. The system according to claim 11, wherein the at least one automated processor is further configured to select the optimum target further in dependence on an evaluation of a competitive alternate allocation of the respective possible target.

13. The system according to claim 11, wherein the plurality of communications comprise voice communications, and the input ports comprise voice communication ports.

14. The system according to claim 11, wherein the set of possible targets comprise call center agents, which are configured to handle the respective communication through a telephony routing system.

15. The system according to claim 11, wherein the expected value comprises a revenue or profit metric, and the cost of allocation comprises a compensation rate of a respective target over an expected duration of the communication.

16. The system according to claim 11, wherein the automated communication process comprises and interactive voice response system.

17. The system according to claim 11, further comprising a database of performance results, and wherein the expected value of the determined performance of the request is based on a record in the database associated with a source of the respective communication.

18. A method for pairing communication requests, comprising:
    receiving a series of requests for communication, and information identifying content or requestor-related characteristics associated with each respective requested communication;
    storing availability information and characteristics for a plurality of targets;
    generating a control signal for controlling at least establishment of the respective requested communication involving the requestor and a selected respective target, selectively optimized dependent on at least the information identifying content or requestor-related characteristics associated with the respective requested communication, a competitive alternate allocation of the selected respective target, an expected value of the respective requested communication, a cost of allocation of the respective communication to respective targets of the plurality of targets, and an anticipated wait time for availability of the respective targets of the plurality of targets; and outputting information selectively optimized dependent on the control signal.

19. The method according to claim 18, wherein the control signal is further generated in dependence on a comprehensive evaluation of competitive alternate allocations of respective targets of the plurality of targets.

20. The method according to claim 18, further comprising generating the control signal further in dependence on a history of the requestor.

\* \* \* \* \*